US011168144B2

(12) United States Patent
Humphrey et al.

(10) Patent No.: US 11,168,144 B2
(45) Date of Patent: Nov. 9, 2021

(54) ACTIVATABLE ANTI-PDL1 ANTIBODIES, AND METHODS OF USE THEREOF

(71) Applicant: CytomX Therapeutics, Inc., South San Francisco, CA (US)

(72) Inventors: Rachel Humphrey, South San Francisco, CA (US); Lori Carman, South San Francisco, CA (US); Matthias Will, South San Francisco, CA (US); Beiyao Zheng, South San Francisco, CA (US); Kathe Balinski, Hilton Head Island, SC (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 185 days.

(21) Appl. No.: 15/995,066

(22) Filed: May 31, 2018

(65) Prior Publication Data

US 2019/0016814 A1    Jan. 17, 2019

Related U.S. Application Data

(60) Provisional application No. 62/657,567, filed on Apr. 13, 2018, provisional application No. 62/555,598, filed on Sep. 7, 2017, provisional application No. 62/534,950, filed on Jul. 20, 2017, provisional application No. 62/513,937, filed on Jun. 1, 2017.

(51) Int. Cl.
| | |
|---|---|
| *C07K 16/28* | (2006.01) |
| *A61K 47/65* | (2017.01) |
| *A61P 35/00* | (2006.01) |
| *A61K 39/00* | (2006.01) |

(52) U.S. Cl.
CPC .......... *C07K 16/2896* (2013.01); *A61K 47/65* (2017.08); *A61P 35/00* (2018.01); *C07K 16/2818* (2013.01); *C07K 16/2827* (2013.01); *A61K 2039/507* (2013.01); *A61K 2039/545* (2013.01); *A61K 2300/00* (2013.01); *C07K 2317/21* (2013.01); *C07K 2317/33* (2013.01); *C07K 2317/34* (2013.01); *C07K 2317/622* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Bostwell et al. |
| 4,485,045 | A | 11/1984 | Regen |
| 4,522,811 | A | 6/1985 | Eppstein et al. |
| 4,544,545 | A | 10/1985 | Ryan et al. |
| 5,013,556 | A | 5/1991 | Woodle et al. |
| 5,030,719 | A | 7/1991 | Umemoto et al. |
| 5,151,510 | A | 9/1992 | Stec et al. |
| 6,803,192 | B1 | 10/2004 | Chen |
| 6,936,704 | B1 | 8/2005 | Freeman et al. |
| 7,038,013 | B2 | 5/2006 | Freeman et al. |
| 7,101,550 | B2 | 9/2006 | Wood et al. |
| 7,105,328 | B2 | 9/2006 | Wood et al. |
| 7,432,351 | B1 | 10/2008 | Chen |
| 7,449,300 | B2 | 11/2008 | Chen et al. |
| 7,465,790 | B2 | 12/2008 | Waldmann et al. |
| 7,635,757 | B2 | 12/2009 | Freeman et al. |
| 7,666,817 | B2 | 2/2010 | Daugherty et al. |
| 7,700,301 | B2 | 4/2010 | Wood et al. |
| 7,709,214 | B2 | 5/2010 | Freeman et al. |
| 7,722,868 | B2 | 5/2010 | Freeman et al. |
| 7,794,710 | B2 | 9/2010 | Chen et al. |
| 7,892,540 | B2 | 2/2011 | Chen et al. |
| 7,931,896 | B2 | 4/2011 | Chen |
| 7,943,743 | B2 | 5/2011 | Korman et al. |
| 8,062,852 | B2 | 11/2011 | Mozaffarian et al. |
| 8,168,179 | B2 | 5/2012 | Honjo et al. |
| 8,217,149 | B2 | 7/2012 | Irving et al. |
| 8,273,864 | B2 | 9/2012 | Chen |
| 8,383,796 | B2 | 2/2013 | Korman et al. |
| 8,460,927 | B2 | 6/2013 | Chen |
| 8,507,663 | B2 | 8/2013 | Defougerolles et al. |
| 8,513,390 | B2 | 8/2013 | Stagliano et al. |
| 8,518,404 | B2 | 8/2013 | Daugherty et al. |
| 8,529,898 | B2 | 9/2013 | Daugherty et al. |
| 8,541,203 | B2 | 9/2013 | Daugherty et al. |
| 8,552,154 | B2 | 10/2013 | Freeman et al. |
| 8,563,269 | B2 | 10/2013 | Stagliano et al. |
| 8,617,546 | B2 | 12/2013 | Kang et al. |

(Continued)

FOREIGN PATENT DOCUMENTS

| | | |
|---|---|---|
| CN | 105461808 A | 4/2016 |
| CN | 105777906 A | 7/2016 |

(Continued)

OTHER PUBLICATIONS

Chen et al. 'Selective antibody activationthrough protease-activated proantibodies that mask binding siteswith inhibitory domains.' Sci Rep 7, 11587 (2017). https://doi.org/10.1038/s41598-017-11886-7.*
Anonymous (May 18, 2017) "History of Changes for Study: NCT03013491. PROCLAIM-CX-072: A Trial to Find Safe and Active Doses of an Investigational Drug CX-072 for Patients With Solid Tumors or Lymphomas" U.S. National Library of Medicine: *Clinical Trials.gov Archive* [online]. Retrieved from: htttps://clinicaltrials.gov/ct2/histoty/NCT03013491?V 9=View#StudyPageTop, on Sep. 12, 2018, 13 pages.
Baecher-Allan, C. et al. (2001) "CD4+CD25$^{high}$ Regulatory Cells in Human Peripheral Blood" *J Immunol*, 167:1245-1253.

(Continued)

*Primary Examiner* — Nora M Rooney
(74) *Attorney, Agent, or Firm* — Fish & Richardson P.C.

(57) ABSTRACT

The invention relates generally to activatable antibodies that specifically bind to PDL1 and methods of making and using these anti-PDL1 activatable antibodies in a variety of therapeutic, diagnostic and prophylactic indications.

39 Claims, 17 Drawing Sheets
Specification includes a Sequence Listing.

(56) References Cited

U.S. PATENT DOCUMENTS

| | | |
|---|---|---|
| 8,652,465 B2 | 2/2014 | Freeman et al. |
| 8,735,553 B1 | 5/2014 | Kang et al. |
| 8,741,295 B2 | 6/2014 | Olive |
| 8,747,833 B2 | 6/2014 | Chen et al. |
| 8,779,108 B2 | 7/2014 | Queva et al. |
| 8,809,504 B2 | 8/2014 | Lauermann |
| 8,962,804 B2 | 2/2015 | Williams et al. |
| 8,981,063 B2 | 3/2015 | Chen |
| 8,992,927 B1 | 3/2015 | Clube |
| 8,993,524 B2 | 3/2015 | Bedi et al. |
| 9,045,545 B1 | 6/2015 | Clube |
| 9,062,112 B2 | 6/2015 | Chen |
| 9,067,998 B1 | 6/2015 | Clube |
| 9,095,628 B2 | 8/2015 | Govindan et al. |
| 9,102,725 B2 | 8/2015 | Korman et al. |
| 9,102,727 B2 | 8/2015 | Freeman et al. |
| 9,109,034 B1 | 8/2015 | Clube |
| 9,168,296 B2 | 10/2015 | Mozaffarian et al. |
| 9,169,321 B2 | 10/2015 | Daugherty et al. |
| 9,175,082 B2 | 11/2015 | Zhou et al. |
| 9,187,562 B1 | 11/2015 | Clube |
| 9,212,224 B2 | 12/2015 | Cogswell et al. |
| 9,221,917 B2 | 12/2015 | Baurin et al. |
| 9,273,135 B2 | 3/2016 | Korman et al. |
| 9,283,286 B2 | 3/2016 | Govindan et al. |
| 9,303,089 B2 | 4/2016 | Clube |
| 9,393,301 B2 | 7/2016 | Honjo et al. |
| 9,402,899 B2 | 8/2016 | Honjo et al. |
| 9,416,180 B1 | 8/2016 | Clube |
| 9,422,562 B2 | 8/2016 | DeFougerolles et al. |
| 9,428,578 B2 | 8/2016 | Clube |
| 9,439,962 B2 | 9/2016 | Honjo et al. |
| 9,439,963 B2 | 9/2016 | Clube |
| 9,453,078 B2 | 9/2016 | Stagliano et al. |
| 9,457,080 B2 | 10/2016 | Freeman et al. |
| 9,486,536 B2 | 11/2016 | Govindan et al. |
| 9,493,565 B2 | 11/2016 | Queva et al. |
| 9,567,399 B1 | 2/2017 | Campbell et al. |
| 9,580,505 B2 | 2/2017 | Korman et al. |
| 9,580,507 B2 | 2/2017 | Korman et al. |
| 9,617,338 B1 | 4/2017 | Campbell et al. |
| 9,624,298 B2 | 4/2017 | Nastri et al. |
| 9,650,429 B2 | 5/2017 | Ostrand-Rosenberg |
| 9,676,863 B2 | 6/2017 | Lo |
| 9,694,088 B2 | 7/2017 | Govindan et al. |
| 9,709,568 B2 | 7/2017 | Pierce et al. |
| 9,724,390 B2 | 8/2017 | Gurney |
| 9,765,147 B2 | 9/2017 | Wong et al. |
| 9,789,183 B1 | 10/2017 | Wang et al. |
| 9,828,434 B2 | 11/2017 | Marasco et al. |
| 9,845,356 B2 | 12/2017 | Freeman et al. |
| 9,856,320 B2 | 1/2018 | Cogswell et al. |
| 9,885,721 B2 | 2/2018 | Couto et al. |
| 9,907,849 B2 | 3/2018 | Petit et al. |
| 9,914,769 B2 | 3/2018 | Clube |
| 9,920,123 B2 | 3/2018 | Irving et al. |
| 9,957,323 B2 | 5/2018 | Sainson et al. |
| 9,987,258 B2 | 6/2018 | Villagra et al. |
| 9,988,452 B2 | 6/2018 | Freeman et al. |
| 10,011,656 B2 | 7/2018 | Freeman et al. |
| 10,059,762 B2 | 8/2018 | Stagliano et al. |
| 10,059,769 B2 | 8/2018 | Fang et al. |
| 10,072,082 B2 | 9/2018 | Cogswell et al. |
| 10,077,300 B2 | 9/2018 | Daugherty et al. |
| 10,077,308 B2 | 9/2018 | Wang et al. |
| 10,081,679 B2 | 9/2018 | Ben-Moshe et al. |
| 10,118,961 B2 | 11/2018 | Ben-Moshe et al. |
| 10,208,119 B2 | 2/2019 | Fang et al. |
| 10,336,824 B2 | 7/2019 | West et al. |
| 10,669,339 B2 | 6/2020 | West et al. |
| 10,875,913 B2 | 12/2020 | Stagliano et al. |
| 2004/0109855 A1 | 6/2004 | Waldmann et al. |
| 2009/0304719 A1 | 12/2009 | Daugherty et al. |
| 2009/0317368 A1 | 12/2009 | Chen |
| 2010/0189651 A1 | 7/2010 | Stagliano et al. |
| 2010/0189727 A1 | 7/2010 | Ulrich et al. |
| 2010/0203056 A1 | 8/2010 | Irving et al. |
| 2011/0280877 A1 | 11/2011 | Tamada |
| 2012/0149061 A1 | 6/2012 | Stagliano et al. |
| 2012/0207756 A1 | 8/2012 | Stagliano et al. |
| 2012/0237512 A1 | 9/2012 | Daugherty et al. |
| 2012/0237977 A1 | 9/2012 | Daugherty et al. |
| 2012/0244154 A1 | 9/2012 | Daugherty et al. |
| 2013/0045202 A1 | 2/2013 | Irving et al. |
| 2013/0071403 A1 | 3/2013 | Rolland et al. |
| 2013/0309230 A1 | 11/2013 | Stagliano et al. |
| 2013/0309250 A1 | 11/2013 | Cogswell et al. |
| 2013/0323249 A1 | 12/2013 | Zhou et al. |
| 2014/0024810 A1 | 1/2014 | Stagliano et al. |
| 2014/0045195 A1 | 2/2014 | Daugherty et al. |
| 2014/0065135 A1 | 3/2014 | Irving et al. |
| 2014/0341917 A1 | 11/2014 | Nastri et al. |
| 2014/0356363 A1 | 12/2014 | Zhou et al. |
| 2015/0044165 A1 | 2/2015 | Chen et al. |
| 2015/0071910 A1 | 3/2015 | Kowanetz et al. |
| 2015/0073129 A1 | 3/2015 | Hefting et al. |
| 2015/0125463 A1 | 5/2015 | Cogswell et al. |
| 2015/0202291 A1 | 7/2015 | Bosch et al. |
| 2015/0203580 A1 | 7/2015 | Papadopoulos et al. |
| 2015/0210772 A1 | 7/2015 | Kim |
| 2015/0232533 A1 | 8/2015 | Chen |
| 2015/0239972 A1 | 8/2015 | Ahmed et al. |
| 2015/0322153 A1 | 11/2015 | Irving et al. |
| 2015/0328311 A1 | 11/2015 | Narwal et al. |
| 2015/0344577 A1 | 12/2015 | Fu |
| 2015/0346210 A1 | 12/2015 | Nitta et al. |
| 2015/0352206 A1 | 12/2015 | Gajewski et al. |
| 2015/0355184 A1 | 12/2015 | Pierce et al. |
| 2016/0009805 A1 | 1/2016 | Kowanetz et al. |
| 2016/0031990 A1 | 2/2016 | Steele et al. |
| 2016/0045597 A1 | 2/2016 | Corse et al. |
| 2016/0060344 A1 | 3/2016 | Narwal et al. |
| 2016/0067336 A1 | 3/2016 | Fandi et al. |
| 2016/0089434 A1 | 3/2016 | Hoos |
| 2016/0096889 A1 | 4/2016 | Chen |
| 2016/0096890 A1 | 4/2016 | Chen |
| 2016/0122425 A1 | 5/2016 | Daugherty et al. |
| 2016/0122829 A1 | 5/2016 | Hammerman |
| 2016/0130348 A1 | 5/2016 | Langermarin et al. |
| 2016/0131646 A1 | 5/2016 | Mozaffarian et al. |
| 2016/0151515 A1 | 6/2016 | Joubert et al. |
| 2016/0175397 A1 | 6/2016 | Umaria et al. |
| 2016/0176962 A1 | 6/2016 | Murriel et al. |
| 2016/0193239 A1 | 7/2016 | Baylin et al. |
| 2016/0206754 A1 | 7/2016 | Chang et al. |
| 2016/0222117 A1 | 8/2016 | Irving et al. |
| 2016/0222118 A1 | 8/2016 | Chen et al. |
| 2016/0222120 A1 | 8/2016 | Narwal et al. |
| 2016/0222121 A1 | 8/2016 | Johnson et al. |
| 2016/0228546 A1 | 8/2016 | Stagliano et al. |
| 2016/0251437 A1 | 9/2016 | Dong et al. |
| 2016/0272712 A1 | 9/2016 | Freeman et al. |
| 2016/0289343 A1 | 10/2016 | Wu |
| 2016/0303231 A1 | 10/2016 | Iannone et al. |
| 2016/0305947 A1 | 10/2016 | Pierce et al. |
| 2016/0311903 A1 | 10/2016 | West et al. |
| 2016/0319017 A1 | 11/2016 | Clube |
| 2016/0319022 A1 | 11/2016 | Yang et al. |
| 2016/0333414 A1 | 11/2016 | Belousov et al. |
| 2016/0340407 A1 | 11/2016 | Hodi et al. |
| 2016/0340429 A1 | 11/2016 | Waksal et al. |
| 2016/0347848 A1 | 12/2016 | Hammond et al. |
| 2016/0362460 A1 | 12/2016 | Olwill et al. |
| 2016/0362492 A1 | 12/2016 | Freeman et al. |
| 2017/0007693 A1 | 1/2017 | Weiner et al. |
| 2017/0007715 A1 | 1/2017 | Andreev et al. |
| 2017/0015758 A1 | 1/2017 | Hammond |
| 2017/0021019 A1 | 1/2017 | Zibelman et al. |
| 2017/0029508 A1 | 2/2017 | Eisenbach-Schwartz et al. |
| 2017/0037132 A1 | 2/2017 | Manekas et al. |
| 2017/0051060 A1 | 2/2017 | Honjo et al. |
| 2017/0056391 A1 | 3/2017 | Li |
| 2017/0058033 A1 | 3/2017 | Ludwig et al. |
| 2017/0081397 A1 | 3/2017 | Stagliano et al. |

(56) References Cited

U.S. PATENT DOCUMENTS

| | | |
|---|---|---|
| 2017/0089918 A1 | 3/2017 | Dong |
| 2017/0114137 A1 | 4/2017 | Li |
| 2017/0137522 A1 | 5/2017 | Queva et al. |
| 2017/0143780 A1 | 5/2017 | Zitvogel et al. |
| 2017/0158767 A1 | 6/2017 | Korman et al. |
| 2017/0182161 A1 | 6/2017 | Zhou et al. |
| 2017/0189476 A1 | 7/2017 | Sung et al. |
| 2017/0198051 A1 | 7/2017 | Eckelman et al. |
| 2017/0202902 A1 | 7/2017 | McLaughlin et al. |
| 2017/0204184 A1 | 7/2017 | Zha et al. |
| 2017/0224791 A1 | 8/2017 | Okamura et al. |
| 2017/0253653 A1 | 9/2017 | Nastri et al. |
| 2017/0253654 A1 | 9/2017 | Nastri et al. |
| 2017/0260271 A1 | 9/2017 | Igawa et al. |
| 2017/0266310 A1 | 9/2017 | Govindan et al. |
| 2017/0267756 A1 | 9/2017 | Riddell et al. |
| 2017/0281765 A1 | 10/2017 | Zhou et al. |
| 2017/0290808 A1 | 10/2017 | Charo et al. |
| 2017/0290923 A1 | 10/2017 | Li et al. |
| 2017/0306025 A1 | 10/2017 | Du et al. |
| 2017/0306050 A1 | 10/2017 | Degenhardt et al. |
| 2017/0320954 A1 | 11/2017 | Barry et al. |
| 2017/0327583 A1 | 11/2017 | Bissonnette et al. |
| 2017/0362321 A1 | 12/2017 | Campbell et al. |
| 2017/0367997 A1 | 12/2017 | Kawakami et al. |
| 2018/0000851 A1 | 1/2018 | Krieg |
| 2018/0002423 A1 | 1/2018 | Wang et al. |
| 2018/0002424 A1 | 1/2018 | Belk et al. |
| 2018/0002436 A1 | 1/2018 | Lo |
| 2018/0015161 A1 | 1/2018 | Weiner et al. |
| 2018/0016555 A1 | 1/2018 | Borges et al. |
| 2018/0022809 A1 | 1/2018 | Kowanetz et al. |
| 2018/0031567 A1 | 2/2018 | Dennis et al. |
| 2018/0071340 A1 | 3/2018 | Avigan et al. |
| 2018/0078626 A1 | 3/2018 | Avigan et al. |
| 2018/0078650 A1 | 3/2018 | Avigan et al. |
| 2018/0085350 A1 | 3/2018 | Avigan et al. |
| 2018/0085398 A1 | 3/2018 | Avigan et al. |
| 2018/0094067 A1 | 4/2018 | Wong et al. |
| 2018/0155430 A1 | 6/2018 | Ahmed et al. |
| 2018/0155431 A1 | 6/2018 | Herting et al. |
| 2018/0161464 A1 | 6/2018 | Kelly et al. |
| 2018/0162942 A1 | 6/2018 | Simon et al. |
| 2018/0171025 A1 | 6/2018 | Kim |
| 2018/0185482 A1 | 7/2018 | Sheng et al. |
| 2018/0185483 A1 | 7/2018 | Petit et al. |
| 2018/0186882 A1 | 7/2018 | Freeman et al. |
| 2018/0196055 A1 | 7/2018 | Couto et al. |
| 2018/0200338 A1 | 7/2018 | Umana et al. |
| 2018/0201680 A1 | 7/2018 | Freeman et al. |
| 2018/0230431 A1 | 8/2018 | Bi et al. |
| 2018/0238884 A1 | 8/2018 | Bass et al. |
| 2018/0273624 A1 | 9/2018 | Cogswell et al. |
| 2018/0274038 A1 | 9/2018 | Belousov et al. |
| 2018/0282413 A1 | 10/2018 | Cogswell et al. |
| 2018/0282414 A1 | 10/2018 | Cogswell et al. |
| 2018/0296614 A1 | 10/2018 | Bigner et al. |
| 2018/0305437 A1 | 10/2018 | Wahlberg |
| 2018/0312565 A1 | 11/2018 | Wahlberg et al. |
| 2018/0312590 A1 | 11/2018 | Cogswell et al. |
| 2018/0319887 A1 | 11/2018 | Cogswell et al. |
| 2018/0346574 A1 | 12/2018 | Fang et al. |
| 2019/0016807 A1 | 1/2019 | Irving et al. |
| 2019/0106494 A1 | 4/2019 | Wang et al. |
| 2019/0119370 A1 | 4/2019 | Stagliano et al. |
| 2019/0211089 A1 | 7/2019 | Daugherty et al. |
| 2019/0382493 A1 | 12/2019 | West et al. |
| 2020/0231677 A1 | 7/2020 | West et al. |

FOREIGN PATENT DOCUMENTS

| | | |
|---|---|---|
| CN | 106243225 A | 12/2016 |
| CN | 106478819 B | 3/2017 |
| CN | 106699891 A | 5/2017 |
| CN | 106978400 A | 7/2017 |
| CN | 107459578 A | 12/2017 |
| CN | 107973854 A | 5/2018 |
| CN | 108250296 A | 7/2018 |
| CN | 108276492 A | 7/2018 |
| CN | 106977602 B | 9/2018 |
| CN | 106243223 B | 3/2019 |
| EP | 1523503 B1 | 4/2009 |
| EP | 1324771 B1 | 6/2011 |
| EP | 1907000 B1 | 10/2012 |
| EP | 2172219 B1 | 9/2013 |
| EP | 1907424 B1 | 7/2015 |
| EP | 2982379 A1 | 2/2016 |
| EP | 2079760 B1 | 4/2016 |
| EP | 3070102 A1 | 9/2016 |
| EP | 2397156 B1 | 11/2016 |
| EP | 1234031 B1 | 3/2017 |
| EP | 2376535 B1 | 4/2017 |
| EP | 2393835 B1 | 4/2017 |
| EP | 2133365 B1 | 5/2017 |
| EP | 2542590 B1 | 5/2017 |
| EP | 2397155 B1 | 12/2017 |
| EP | 1810026 B1 | 4/2018 |
| JP | 2012-511033 | 5/2012 |
| KR | 20180016321 A | 2/2018 |
| RU | 2665790 C1 | 9/2018 |
| TW | 201718657 A | 6/2017 |
| WO | WO 94/11026 A2 | 5/1994 |
| WO | WO 2001/14557 A1 | 3/2001 |
| WO | WO 2001/91798 A2 | 12/2001 |
| WO | WO 2002/030460 A2 | 4/2002 |
| WO | WO 2004/009638 A1 | 1/2004 |
| WO | WO 2006/121168 | 11/2006 |
| WO | WO 2007/005874 | 1/2007 |
| WO | WO 2007/105027 A1 | 9/2007 |
| WO | WO 2008/156712 | 12/2008 |
| WO | WO 2009/025846 A2 | 2/2009 |
| WO | WO 2010/077643 | 7/2010 |
| WO | WO 2010/081173 A2 | 7/2010 |
| WO | WO 2011/066389 A1 | 6/2011 |
| WO | WO 2012/145493 A1 | 10/2012 |
| WO | WO 2013/019906 A1 | 2/2013 |
| WO | WO 2013/079174 | 6/2013 |
| WO | WO 2013/128194 | 9/2013 |
| WO | WO 2013/163631 A2 | 10/2013 |
| WO | WO 2013/173223 A1 | 11/2013 |
| WO | WO 2013/192546 A1 | 12/2013 |
| WO | WO 2014/026136 A2 | 2/2014 |
| WO | WO 2014/055897 A2 | 4/2014 |
| WO | WO 2014/074852 A1 | 5/2014 |
| WO | WO 2014/100079 A1 | 6/2014 |
| WO | WO 2014/100439 A2 | 6/2014 |
| WO | WO 2014/100483 A1 | 6/2014 |
| WO | WO 2014/107599 A2 | 7/2014 |
| WO | WO 2014/116846 A2 | 7/2014 |
| WO | WO 2014/151006 A2 | 9/2014 |
| WO | WO 2014/165082 A2 | 10/2014 |
| WO | WO 2014/195852 A1 | 12/2014 |
| WO | WO 2014/206107 | 12/2014 |
| WO | WO 2015/013671 A1 | 1/2015 |
| WO | WO 2015/038538 A1 | 3/2015 |
| WO | WO 2015/048520 A1 | 4/2015 |
| WO | WO 2015/069697 A2 | 5/2015 |
| WO | WO 2015/069770 A1 | 5/2015 |
| WO | WO 2015/081158 A1 | 6/2015 |
| WO | WO 2015/092393 A2 | 6/2015 |
| WO | WO 2015/095404 A2 | 6/2015 |
| WO | WO 2015/109124 A2 | 7/2015 |
| WO | WO 2015/195163 A1 | 12/2015 |
| WO | WO 2016/000619 A1 | 1/2016 |
| WO | WO 2016/006241 | 1/2016 |
| WO | WO 2016/006241 A1 | 1/2016 |
| WO | WO 2016/030455 | 3/2016 |
| WO | WO 2016/030455 A1 | 3/2016 |
| WO | WO 2016/050721 | 4/2016 |
| WO | WO 2016/050721 A1 | 4/2016 |
| WO | WO 2016/059602 | 4/2016 |
| WO | WO 2016/059602 A2 | 4/2016 |
| WO | WO 2016/062722 | 4/2016 |
| WO | WO 2016/062722 A1 | 4/2016 |

(56) References Cited

FOREIGN PATENT DOCUMENTS

| | | |
|---|---|---|
| WO | WO 2016/071701 | 5/2016 |
| WO | WO 2016/071701 A1 | 5/2016 |
| WO | WO 2016/075174 | 5/2016 |
| WO | WO 2016/075174 A1 | 5/2016 |
| WO | WO 2016/115274 | 7/2016 |
| WO | WO 2016/115274 A1 | 7/2016 |
| WO | WO 2016/124558 | 8/2016 |
| WO | WO 2016/124558 A1 | 8/2016 |
| WO | WO 2016/128912 | 8/2016 |
| WO | WO 2016/128912 A1 | 8/2016 |
| WO | WO 2016/137985 | 9/2016 |
| WO | WO 2016/137985 A1 | 9/2016 |
| WO | WO 2016/146329 | 9/2016 |
| WO | WO 2016/146329 A1 | 9/2016 |
| WO | WO 2016/149201 A2 | 9/2016 |
| WO | WO 2016/154412 A2 | 9/2016 |
| WO | WO 2016/156501 A1 | 10/2016 |
| WO | WO 2016/160792 A1 | 10/2016 |
| WO | WO 2016/172249 A1 | 10/2016 |
| WO | WO 2016/175275 A1 | 11/2016 |
| WO | WO 2016/181348 A1 | 11/2016 |
| WO | WO 2016/183326 A1 | 11/2016 |
| WO | WO 2016/196381 A1 | 12/2016 |
| WO | WO 2016/197367 A1 | 12/2016 |
| WO | WO 2016/205277 A1 | 12/2016 |
| WO | WO 2017/004192 A1 | 1/2017 |
| WO | WO 2017/020802 A1 | 2/2017 |
| WO | WO 2017/020858 A1 | 2/2017 |
| WO | WO 2017/059387 A1 | 4/2017 |
| WO | WO 2017/062797 A1 | 4/2017 |
| WO | WO 2017/084495 A1 | 5/2017 |
| WO | WO 2017/087547 A1 | 5/2017 |
| WO | WO 2017/087851 A1 | 5/2017 |
| WO | WO 2017/097407 A1 | 6/2017 |
| WO | WO 2017/099034 A1 | 6/2017 |
| WO | WO 2017/120604 A1 | 7/2017 |
| WO | WO 2017/136562 A2 | 8/2017 |
| WO | WO 2017/136820 A2 | 8/2017 |
| WO | WO 2017/148424 A1 | 9/2017 |
| WO | WO 2017/161154 A2 | 9/2017 |
| WO | WO 2017/161976 A1 | 9/2017 |
| WO | WO 2017/172518 A1 | 10/2017 |
| WO | WO 2017/174331 A1 | 10/2017 |
| WO | WO 2017/181111 A2 | 10/2017 |
| WO | WO 2017/192798 A1 | 11/2017 |
| WO | WO 2017/193032 A2 | 11/2017 |
| WO | WO 2017/193094 A1 | 11/2017 |
| WO | WO 2017/196867 A1 | 11/2017 |
| WO | WO 2017/201281 A1 | 11/2017 |
| WO | WO 2017/201501 A1 | 11/2017 |
| WO | WO 2017/202744 A1 | 11/2017 |
| WO | WO 2017/205801 A1 | 11/2017 |
| WO | WO 2017/210302 A1 | 12/2017 |
| WO | WO 2017/210335 A1 | 12/2017 |
| WO | WO 2017/220988 A1 | 12/2017 |
| WO | WO 2018/009894 A1 | 1/2018 |
| WO | WO 2018/054940 A1 | 3/2018 |
| WO | WO 2018/057506 A1 | 3/2018 |
| WO | WO 2018/065938 A1 | 4/2018 |
| WO | WO 2018/080812 A1 | 5/2018 |
| WO | WO 2018/089780 A1 | 5/2018 |
| WO | WO 2018/100534 A1 | 6/2018 |
| WO | WO 2018/106529 A1 | 6/2018 |
| WO | WO 2018/110515 A1 | 6/2018 |
| WO | WO 2018/111890 A1 | 6/2018 |
| WO | WO 2018/115051 A1 | 6/2018 |
| WO | WO 2018/115859 A1 | 6/2018 |
| WO | WO 2018/119475 A1 | 6/2018 |
| WO | WO 2018/133873 A1 | 7/2018 |
| WO | WO 2018/150224 A1 | 8/2018 |
| WO | WO 2018/152415 A1 | 8/2018 |
| WO | WO 2018/153320 A1 | 8/2018 |
| WO | WO 2018/162749 A1 | 9/2018 |
| WO | WO 2018/170021 A1 | 9/2018 |
| WO | WO 2018/175279 A2 | 9/2018 |
| WO | WO 2018/178040 A1 | 10/2018 |
| WO | WO 2018/178122 A1 | 10/2018 |
| WO | WO 2018/178123 A1 | 10/2018 |

OTHER PUBLICATIONS

Boni, V. et al. (2017) "The First-in-Human, Dose-Finding PROCLAIM-CX-072 Trial to Assess the Antitumor Activity and Tolerability of the Probody™ Therapeutic CX-072 as Monotherapy and in Combination With Ipilimumab or Vemurafenib in Solid Advanced Tumors and Lymphomas" CytomX Therapeutics, Inc. Poster presented at the ESMO (European Societty of Medical Oncology) 2017 Congress; Sep. 8-12, 2017, Madrid, Spain.

Boulware, K.T. et al. (Jun. 15, 2010) "Evolutionary Optimization of Peptide Substrates for Proteases That Exhibit Rapid Hydrolysis Kinetics" *Biotechnology & Bioengineering*, 106(3):339-346.

Brown, J.A. et al. (2003) "Blockade of Programmed Death-1 Ligands on Dendritic Cells Enhances T Cell Activation and Cytokine Production" *J Immunol*, 170:1257-1266.

Carreno, B.M. and M. Collins (2002) "The B7 Family of Ligands and Its Receptors: New Pathways for Costimulation and Inhibition of Immune Responses" *Annu Rev Immunol*, 20:29-53.

Chen, D.S. et al., "Molecular Pathways: Next-Generation Immunotherapy—Inhibiting Programmed Death-Ligand 1 and Programmed Death-1" *Clin Can Res*, 18:6580-6587 (2012).

Cytomx Therapeutics, *Company Overview*. Presented Mar. 2, 2015 at Cowen and Company Annual Healthcare Conference, Boston Massachusetts; 27 pages.

Cytomx Therapeutics, *Company Overview*. Mar. 13, 2015; 27 pages.

Deng, R. et al. (2016) "Preclinical pharmacokinetics, pharmacodynamics, tissue distribution, and tumor penetration of anti-PD-L1 monoclonal antibody, an immune checkpoint inhibitor" *MABS*, 8(3):593-603.

Desnoyers, L.R. et al. (Oct. 16, 2013) "Tumor-Specific Activation of an EGFR-Targeting Probody Enhances Therapeutic Index" *Sci Transl Med*, 5:207ra144 [online]. Retrieved from: http://stm.sciencemag.org/ on Dec. 21, 2018, 11 pages.

Dong, H. et al. (1999) "B7-H1, a third member of the B7 family, co-stimulates T-cell proliferation and interleukin-10 secretion" *Nat Med*, 5(12):1365-1369.

Dong, H. et al. (Aug. 2002) "Tumor-associated B7-H1 promotes T-cell apoptosis: A potential mechanism of immune evasion" *Nat Med*, 8(8):793-800.

Freeman, G.J. et al. (Oct. 2, 2000) "Engagement of the PD-1 Immunoinhibitory Receptor by a Novel B7 Family Member Leads to Negative Regulation of Lymphocyte Activation" *J Exp Med*, 192(7):1027-1034.

Herbst, R.S. et al. (Nov. 27, 2014) "Predictive correlates of response to the anti-PD-L1 antibody MPDL3280A in cancer patients" *Nature*, 515:563-567; including Methods and additional Extended Data display items and Source Data, 18 total pages.

Hwu, P. et al. (2016) "Preliminary safety and clinical activity of atezolizumab combined with cobimetinib and vemurafenib in BRAF V600-mutant metastatic melanoma" *Ann Oncol*, 27(Suppl 6):vi379-vi400; Abstract 1109PD, 1 page.

Irving, B.A. (Feb. 2015) "Probodies Empower a New Generation of Antibody Immunotherapies," CytomX Therapeutics Inc. presentation at Keystone Symposia™ on Molecular and Cellular Biology, Feb. 8-13, 2015; 25 pages.

Iwai, Y. et al. (Sep. 17, 2002) "Involvement of PD-L1 on tumor cells in the escape from host immune system and tumor immunotherapy by PD-L1 blockade" *PNAS*, 99(19):12293-12297.

Iwai, Y. et al. (2017) "Cancer immunotherapies targeting the PD-1 signaling pathway" *J Biomed Sci*, 24(1):26, 11 pages.

Kanai, T. et al. (2003) "Blockade of B7-H1 Suppresses the Development of Chronic Intestinal Inflammation" *J Immunol*, 171:4156-4163.

Larkin, J. et al. (2015) "Combined Nivolumab and Ipilimumab or Monotherapy in Untreated Melanoma" *N Engl J Med*, 373(1):23-34.

Latchman, Y. et al. (Mar. 2001) "PD-L2 is a second ligand for PD-1 and inhibits T cell activation" *Nat Immunol*, 2(3):261-268.

(56) References Cited

OTHER PUBLICATIONS

Lebeau, A.M. et al. (Jan. 2, 2013) "Imaging a functional tumorigenic biomarker in the transformed epithelium" *Proc Natl Acad Sci USA*, 110 (1): 93-98.

Overall, C.M. and O. Kleifeld (Mar. 2006) "Validating Matrix Metalloproteinases as Drug Targets and Anti-Targets for Cancer Therapy" *Nature Rev Cancer*, 6:227-239.

Sharpe, A.H. and G.J. Freeman (Feb. 2002) "The B7-CD28 Superfamily" *Nat Rev Immunol*, 2:116-126.

Spira, A.I. et al. (2017) "PROCLAIM-CX-072: A First-in-Human Trial to Assess Tolerability of the Protease-Activatable Anti-PD-L1 Probody™ CX-072 in Solid Tumors and Lymphomas" CytomX Therapeutics, Inc. Poster TPS3107, Presented at the ASCO Annual Meeting; Jun. 2-6, 2017; Chicago, Illinois.

Wolchok, J.D. et al. (Jul. 11, 2013) "Nivolumab plus Ipilimumab in Advanced Melanoma" *N Engl J Med*, 369(2):122-133.

Wong, C. et al. (2015) "A PD-L1-targeted Probody™ Therapeutic Provides Anti-Tumor Efficacy While Minimizing Induction of Systemic Autoimmunity in Preclinical Studies" CytomX Therapeutics. Poster presented at *The CRI-CIMT-EATI-AACR—The Inaugural International Cancer Immunotherapy Conference: Translating Science into Survival*. New York, NY, Sep. 16-19, 2015.

PCT International Search Report and Written Opinion in International Appln. No. PCT/US2018/035508, dated Sep. 27, 2018, 15 pages.

PCT International Preliminary Report on Patentability in International Appln. No. PCT/US2018/035508, dated Dec. 12, 2019, 8 pages.

Brahmer et al., "Safety and activity of anti-PD-L1 antibody in patients with advanced cancer", N. Engl. J. Med., 2012, 366(26):2455-2465.

* cited by examiner

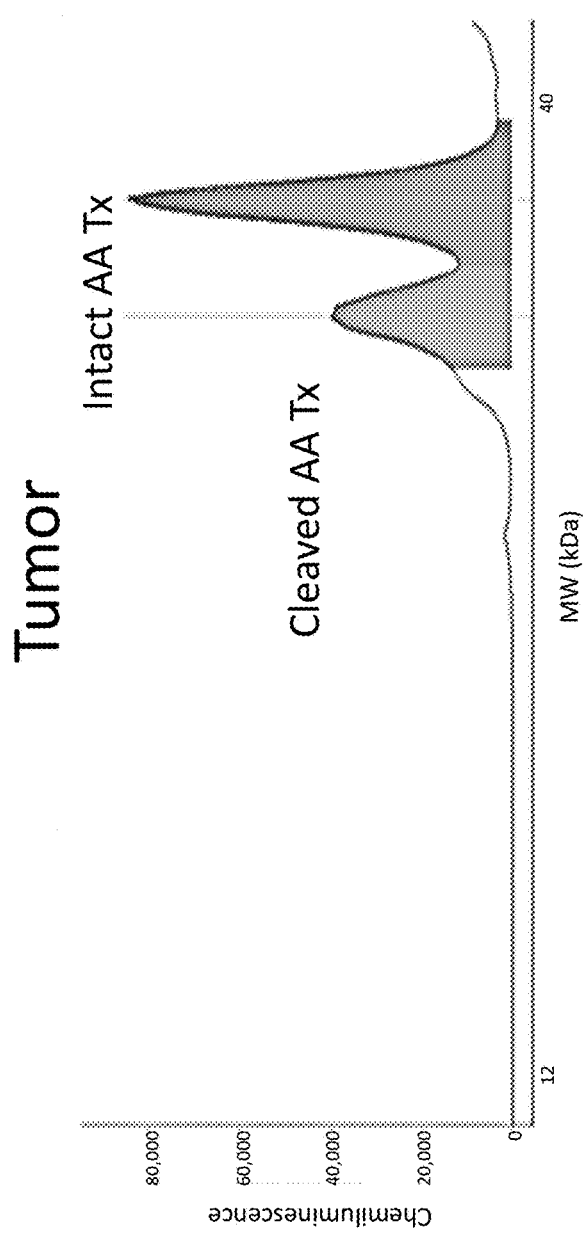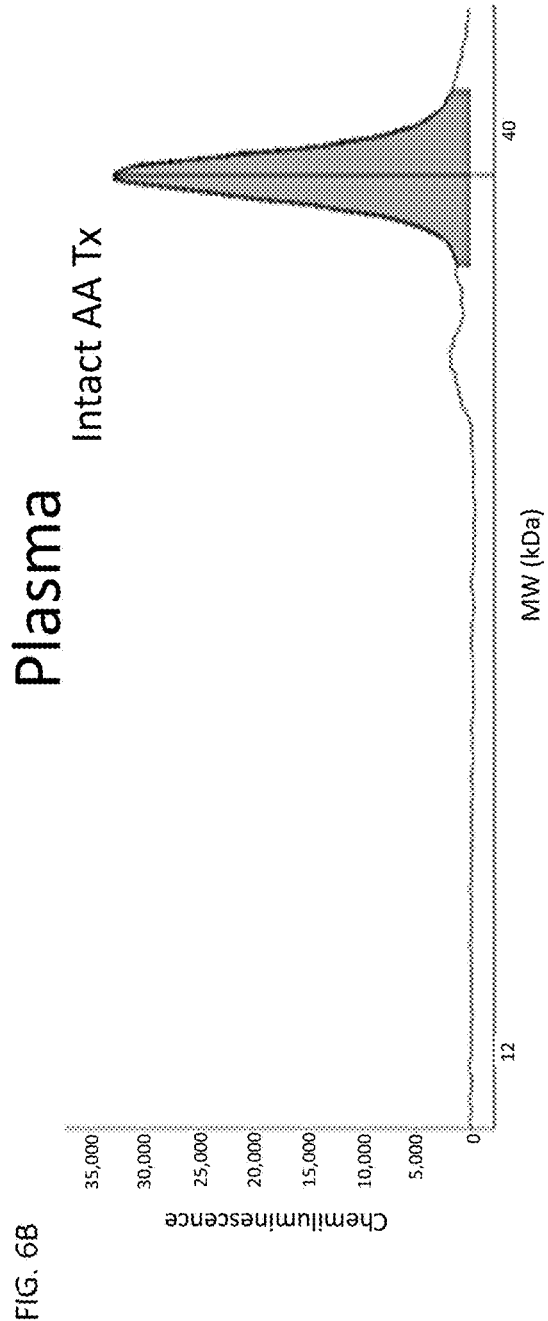
FIG. 6A
FIG. 6B

CR, complete response; ER+ BC, estrogen receptor–positive breast cancer; HNSCC, head and neck squamous cell carcinoma; PD, progressive disease; PR, partial response; RECIST, Response Evaluation Criteria in Solid Tumors; SCC, squamous cell carcinoma; SCLC, small cell lung cancer; SD, stable disease; TNBC, triple-negative breast cancer.

SEQUENCE LISTING

<160> NUMBER OF SEQ ID NOS: 1203

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

```
<400> SEQUENCE: 9

000

<210> SEQ ID NO 10

<400> SEQUENCE: 10

000

<210> SEQ ID NO 11

<400> SEQUENCE: 11

000

<210> SEQ ID NO 12
<211> LENGTH: 108
<212> TYPE: PRT
<213> ORGANISM: Artificial Sequence
<220> FEATURE:
<223> OTHER INFORMATION: Anti-PDL1 Light Chain Variable Sequence of
      C5H9,C5B10,C5E10 and G12H9

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Asn Gly Tyr Pro Ser
                85                  90                  95

Thr Phe Gly Gln Gly Thr Lys Val Glu Ile Lys Arg
            100                 105

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000
```

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

```
<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000

<210> SEQ ID NO 46
<211> LENGTH: 116
<212> TYPE: PRT
<213> ORGANISM: Artificial Sequence
<220> FEATURE:
<223> OTHER INFORMATION: Anti-PDL1 Heavy Chain Variable Sequence of C5H9
      and C5H9v2

<400> SEQUENCE: 46
```

| | | | | | | | | | | | | | | | |
|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Ser | Ile | Trp | Arg | Asn | Gly | Ile | Val | Thr | Val | Tyr | Ala | Asp | Ser | Val |
| 50 | | | | | 55 | | | | | 60 | | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Trp | Ser | Ala | Ala | Phe | Asp | Tyr | Trp | Gly | Gln | Gly | Thr | Leu | Val |
| | | | 100 | | | | | 105 | | | | | 110 | | |
| Thr | Val | Ser | Ser | | | | | | | | | | | | |
| | | | 115 | | | | | | | | | | | | |

<210> SEQ ID NO 47

<400> SEQUENCE: 47

000

<210> SEQ ID NO 48
<211> LENGTH: 116
<212> TYPE: PRT
<213> ORGANISM: Artificial Sequence
<220> FEATURE:
<223> OTHER INFORMATION: Anti-PDL1 Heavy Chain Variable Sequence C5B10

<400> SEQUENCE: 48

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Trp Arg Asn Gly Ile Val Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ala Gly Tyr Asp Tyr Trp Gly Gln Gly Thr Leu Val
            100                 105                 110

Thr Val Ser Ser
        115
```

<210> SEQ ID NO 49

<400> SEQUENCE: 49

000

<210> SEQ ID NO 50
<211> LENGTH: 116
<212> TYPE: PRT
<213> ORGANISM: Artificial Sequence
<220> FEATURE:
<223> OTHER INFORMATION: Anti-PDL1 Heavy Chain Variable Sequence C5E10

<400> SEQUENCE: 50

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Trp Arg Asn Gly Ile Val Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Lys Gly Phe Asp Tyr Trp Gly Gln Gly Thr Leu Val
            100                 105                 110
```

Thr Val Ser Ser
        115

<210> SEQ ID NO 51

<400> SEQUENCE: 51

000

<210> SEQ ID NO 52
<211> LENGTH: 120
<212> TYPE: PRT
<213> ORGANISM: Artificial Sequence
<220> FEATURE:
<223> OTHER INFORMATION: Anti-PDL1 Heavy Chain Variable Sequence G12H9

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Glu Thr Ser Trp Val Arg Gln Ala Pro Gly Lys Gly Leu Glu
        35                  40                  45

Trp Val Ser Ser Ile Trp Tyr Gln Gly Leu Val Thr Val Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Trp Ser Ala Ala Phe Asp Tyr Trp Gly Gln
            100                 105                 110

Gly Thr Leu Val Thr Val Ser Ser
        115                 120

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58
<211> LENGTH: 108
<212> TYPE: PRT
<213> ORGANISM: Artificial Sequence
<220> FEATURE:
<223> OTHER INFORMATION: Anti-PDL1 Light Chain Variable Sequence of C5H9v2

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Asn Gly Tyr Pro Ser
                85                  90                  95

Thr Phe Gly Gly Gly Thr Lys Val Glu Ile Lys Arg
            100                 105

<210> SEQ ID NO 59
<211> LENGTH: 15
<212> TYPE: PRT
<213> ORGANISM: Artificial Sequence
<220> FEATURE:
<223> OTHER INFORMATION: masking moiety

<400> SEQUENCE: 59

Leu Cys Glu Val Leu Met Leu Leu Gln His Pro Trp Cys Met Gly
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: masking moiety

<400> SEQUENCE: 60

Ile Ala Cys Arg His Phe Met Glu Gln Leu Pro Phe Cys His His
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: masking moiety

<400> SEQUENCE: 61

Phe Gly Pro Arg Cys Gly Glu Ala Ser Thr Cys Val Pro Tyr Glu
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: masking moiety

```
<400> SEQUENCE: 62

Ile Leu Tyr Cys Asp Ser Trp Gly Ala Gly Cys Leu Thr Arg Pro
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: masking moiety

<400> SEQUENCE: 63

Gly Ile Ala Leu Cys Pro Ser His Phe Cys Gln Leu Pro Gln Thr
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: masking moiety

<400> SEQUENCE: 64

Asp Gly Pro Arg Cys Phe Val Ser Gly Glu Cys Ser Pro Ile Gly
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: masking moiety

<400> SEQUENCE: 65

Leu Cys Tyr Lys Leu Asp Tyr Asp Asp Arg Ser Tyr Cys His Ile
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: masking moiety

<400> SEQUENCE: 66

Pro Cys His Pro His Pro Tyr Asp Ala Arg Pro Tyr Cys Asn Val
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: masking moiety

<400> SEQUENCE: 67

Pro Cys Tyr Trp His Pro Phe Phe Ala Tyr Arg Tyr Cys Asn Thr
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: masking moiety

<400> SEQUENCE: 68
```

-continued

```
Val Cys Tyr Tyr Met Asp Trp Leu Gly Arg Asn Trp Cys Ser Ser
1               5                   10                  15
```

<210> SEQ ID NO 69
<211> LENGTH: 15
<212> TYPE: PRT
<213> ORGANISM: Artificial Sequence
<220> FEATURE:
<223> OTHER INFORMATION: masking moiety

<400> SEQUENCE: 69

```
Leu Cys Asp Leu Phe Lys Leu Arg Glu Phe Pro Tyr Cys Met Gly
1               5                   10                  15
```

<210> SEQ ID NO 70
<211> LENGTH: 15
<212> TYPE: PRT
<213> ORGANISM: Artificial Sequence
<220> FEATURE:
<223> OTHER INFORMATION: masking moiety

<400> SEQUENCE: 70

```
Tyr Leu Pro Cys His Phe Val Pro Ile Gly Ala Cys Asn Asn Lys
1               5                   10                  15
```

<210> SEQ ID NO 71
<211> LENGTH: 15
<212> TYPE: PRT
<213> ORGANISM: Artificial Sequence
<220> FEATURE:
<223> OTHER INFORMATION: masking moiety

<400> SEQUENCE: 71

```
Ile Phe Cys His Met Gly Val Val Pro Gln Cys Ala Asn Tyr
1               5                   10                  15
```

<210> SEQ ID NO 72
<211> LENGTH: 15
<212> TYPE: PRT
<213> ORGANISM: Artificial Sequence
<220> FEATURE:
<223> OTHER INFORMATION: masking moiety

<400> SEQUENCE: 72

```
Ala Cys His Pro His Pro Tyr Asp Ala Arg Pro Tyr Cys Asn Val
1               5                   10                  15
```

<210> SEQ ID NO 73
<211> LENGTH: 15
<212> TYPE: PRT
<213> ORGANISM: Artificial Sequence
<220> FEATURE:
<223> OTHER INFORMATION: masking moiety

<400> SEQUENCE: 73

```
Pro Cys His Pro Ala Pro Tyr Asp Ala Arg Pro Tyr Cys Asn Val
1               5                   10                  15
```

<210> SEQ ID NO 74
<211> LENGTH: 15
<212> TYPE: PRT
<213> ORGANISM: Artificial Sequence
<220> FEATURE:
<223> OTHER INFORMATION: masking moiety

<400> SEQUENCE: 74

```
Pro Cys His Pro His Ala Tyr Asp Ala Arg Pro Tyr Cys Asn Val
1               5                   10                  15
```

<210> SEQ ID NO 75
<211> LENGTH: 15
<212> TYPE: PRT
<213> ORGANISM: Artificial Sequence
<220> FEATURE:
<223> OTHER INFORMATION: masking moiety

<400> SEQUENCE: 75

```
Pro Cys His Pro His Pro Ala Asp Ala Arg Pro Tyr Cys Asn Val
1               5                   10                  15
```

<210> SEQ ID NO 76
<211> LENGTH: 15
<212> TYPE: PRT
<213> ORGANISM: Artificial Sequence
<220> FEATURE:
<223> OTHER INFORMATION: masking moiety

<400> SEQUENCE: 76

```
Pro Cys His Pro His Pro Tyr Ala Ala Arg Pro Tyr Cys Asn Val
1               5                   10                  15
```

<210> SEQ ID NO 77
<211> LENGTH: 15
<212> TYPE: PRT
<213> ORGANISM: Artificial Sequence
<220> FEATURE:
<223> OTHER INFORMATION: masking moiety

<400> SEQUENCE: 77

```
Pro Cys His Pro His Pro Tyr Asp Ala Ala Pro Tyr Cys Asn Val
1               5                   10                  15
```

<210> SEQ ID NO 78
<211> LENGTH: 15
<212> TYPE: PRT
<213> ORGANISM: Artificial Sequence
<220> FEATURE:
<223> OTHER INFORMATION: masking moiety

<400> SEQUENCE: 78

```
Pro Cys His Pro His Pro Tyr Asp Ala Arg Pro Ala Cys Asn Val
1               5                   10                  15
```

<210> SEQ ID NO 79
<211> LENGTH: 15
<212> TYPE: PRT
<213> ORGANISM: Artificial Sequence
<220> FEATURE:
<223> OTHER INFORMATION: masking moiety

<400> SEQUENCE: 79

```
Pro Cys His Pro His Pro Tyr Asp Ala Arg Pro Tyr Cys Ala Val
1               5                   10                  15
```

<210> SEQ ID NO 80
<211> LENGTH: 15
<212> TYPE: PRT
<213> ORGANISM: Artificial Sequence
<220> FEATURE:
<223> OTHER INFORMATION: masking moiety

<400> SEQUENCE: 80

Pro Cys His Ala His Pro Tyr Asp Ala Arg Pro Tyr Cys Asn Val

```
                1               5                  10                 15

<210> SEQ ID NO 81
<211> LENGTH: 15
<212> TYPE: PRT
<213> ORGANISM: Artificial Sequence
<220> FEATURE:
<223> OTHER INFORMATION: masking moiety

<400> SEQUENCE: 81

Pro Cys His Pro His Pro Tyr Asp Ala Arg Ala Tyr Cys Asn Val
1               5                  10                 15

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000
```

```
<210> SEQ ID NO 91
<400> SEQUENCE: 91
000

<210> SEQ ID NO 92
<400> SEQUENCE: 92
000

<210> SEQ ID NO 93
<400> SEQUENCE: 93
000

<210> SEQ ID NO 94
<400> SEQUENCE: 94
000

<210> SEQ ID NO 95
<400> SEQUENCE: 95
000

<210> SEQ ID NO 96
<400> SEQUENCE: 96
000

<210> SEQ ID NO 97
<400> SEQUENCE: 97
000

<210> SEQ ID NO 98
<400> SEQUENCE: 98
000

<210> SEQ ID NO 99
<400> SEQUENCE: 99
000

<210> SEQ ID NO 100
<400> SEQUENCE: 100
000

<210> SEQ ID NO 101
<400> SEQUENCE: 101
000

<210> SEQ ID NO 102
```

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125
<400> SEQUENCE: 125
000

<210> SEQ ID NO 126
<400> SEQUENCE: 126
000

<210> SEQ ID NO 127
<400> SEQUENCE: 127
000

<210> SEQ ID NO 128
<400> SEQUENCE: 128
000

<210> SEQ ID NO 129
<400> SEQUENCE: 129
000

<210> SEQ ID NO 130
<400> SEQUENCE: 130
000

<210> SEQ ID NO 131
<400> SEQUENCE: 131
000

<210> SEQ ID NO 132
<400> SEQUENCE: 132
000

<210> SEQ ID NO 133
<400> SEQUENCE: 133
000

<210> SEQ ID NO 134
<400> SEQUENCE: 134
000

<210> SEQ ID NO 135
<400> SEQUENCE: 135
000

<210> SEQ ID NO 136

<400> SEQUENCE: 136

000

<210> SEQ ID NO 137
<211> LENGTH: 158
<212> TYPE: PRT
<213> ORGANISM: Artificial Sequence
<220> FEATURE:
<223> OTHER INFORMATION: PL07-2001-C5H9v2 Light Chain Variable Sequence

<400> SEQUENCE: 137

```
Gln Gly Gln Ser Gly Ser Gly Ile Ala Leu Cys Pro Ser His Phe Cys
1               5                   10                  15

Gln Leu Pro Gln Thr Gly Gly Ser Ser Gly Gly Ser Gly Gly Ser
            20                  25                  30

Gly Gly Ile Ser Ser Gly Leu Leu Ser Gly Arg Ser Asp Asn His Gly
            35                  40                  45

Gly Ser Asp Ile Gln Met Thr Gln Ser Pro Ser Ser Leu Ser Ala Ser
50                  55                  60

Val Gly Asp Arg Val Thr Ile Thr Cys Arg Ala Ser Gln Ser Ile Ser
65                  70                  75                  80

Ser Tyr Leu Asn Trp Tyr Gln Gln Lys Pro Gly Lys Ala Pro Lys Leu
                85                  90                  95

Leu Ile Tyr Ala Ala Ser Ser Leu Gln Ser Gly Val Pro Ser Arg Phe
            100                 105                 110

Ser Gly Ser Gly Ser Gly Thr Asp Phe Thr Leu Thr Ile Ser Ser Leu
            115                 120                 125

Gln Pro Glu Asp Phe Ala Thr Tyr Tyr Cys Gln Gln Asp Asn Gly Tyr
        130                 135                 140

Pro Ser Thr Phe Gly Gly Gly Thr Lys Val Glu Ile Lys Arg
145                 150                 155
```

<210> SEQ ID NO 138
<211> LENGTH: 152
<212> TYPE: PRT
<213> ORGANISM: Artificial Sequence
<220> FEATURE:
<223> OTHER INFORMATION: PL07-2001-C5H9v2-W0 Light Chain Variable
      Sequence

<400> SEQUENCE: 138

```
Gly Ile Ala Leu Cys Pro Ser His Phe Cys Gln Leu Pro Gln Thr Gly
1               5                   10                  15

Gly Gly Ser Ser Gly Gly Ser Gly Gly Ser Gly Gly Ile Ser Ser Gly
            20                  25                  30

Leu Leu Ser Gly Arg Ser Asp Asn His Gly Gly Ser Asp Ile Gln Met
            35                  40                  45

Thr Gln Ser Pro Ser Ser Leu Ser Ala Ser Val Gly Asp Arg Val Thr
50                  55                  60

Ile Thr Cys Arg Ala Ser Gln Ser Ile Ser Ser Tyr Leu Asn Trp Tyr
65                  70                  75                  80

Gln Gln Lys Pro Gly Lys Ala Pro Lys Leu Leu Ile Tyr Ala Ala Ser
                85                  90                  95

Ser Leu Gln Ser Gly Val Pro Ser Arg Phe Ser Gly Ser Gly Ser Gly
            100                 105                 110

Thr Asp Phe Thr Leu Thr Ile Ser Ser Leu Gln Pro Glu Asp Phe Ala
            115                 120                 125
```

```
Thr Tyr Tyr Cys Gln Gln Asp Asn Gly Tyr Pro Ser Thr Phe Gly Gly
    130                 135                 140

Gly Thr Lys Val Glu Ile Lys Arg
145                 150
```

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191
<211> LENGTH: 5
<212> TYPE: PRT
<213> ORGANISM: Artificial Sequence
<220> FEATURE:
<223> OTHER INFORMATION: linker peptide

<400> SEQUENCE: 191

Gly Ser Gly Gly Ser
1               5

<210> SEQ ID NO 192
<211> LENGTH: 4
<212> TYPE: PRT
<213> ORGANISM: Artificial Sequence
<220> FEATURE:
<223> OTHER INFORMATION: linker peptide

<400> SEQUENCE: 192

Gly Gly Gly Ser

```
<210> SEQ ID NO 193
<211> LENGTH: 4
<212> TYPE: PRT
<213> ORGANISM: Artificial Sequence
<220> FEATURE:
<223> OTHER INFORMATION: linker peptide

<400> SEQUENCE: 193

Gly Gly Ser Gly
1

<210> SEQ ID NO 194
<211> LENGTH: 5
<212> TYPE: PRT
<213> ORGANISM: Artificial Sequence
<220> FEATURE:
<223> OTHER INFORMATION: linker peptide

<400> SEQUENCE: 194

Gly Gly Ser Gly Gly
1               5

<210> SEQ ID NO 195
<211> LENGTH: 5
<212> TYPE: PRT
<213> ORGANISM: Artificial Sequence
<220> FEATURE:
<223> OTHER INFORMATION: linker peptide

<400> SEQUENCE: 195

Gly Ser Gly Ser Gly
1               5

<210> SEQ ID NO 196
<211> LENGTH: 5
<212> TYPE: PRT
<213> ORGANISM: Artificial Sequence
<220> FEATURE:
<223> OTHER INFORMATION: linker peptide

<400> SEQUENCE: 196

Gly Ser Gly Gly Gly
1               5

<210> SEQ ID NO 197
<211> LENGTH: 5
<212> TYPE: PRT
<213> ORGANISM: Artificial Sequence
<220> FEATURE:
<223> OTHER INFORMATION: linker peptide

<400> SEQUENCE: 197

Gly Gly Gly Ser Gly
1               5

<210> SEQ ID NO 198
<211> LENGTH: 5
<212> TYPE: PRT
<213> ORGANISM: Artificial Sequence
<220> FEATURE:
<223> OTHER INFORMATION: linker peptide

<400> SEQUENCE: 198

Gly Ser Ser Ser Gly
1               5
```

<210> SEQ ID NO 199
<211> LENGTH: 13
<212> TYPE: PRT
<213> ORGANISM: Artificial Sequence
<220> FEATURE:
<223> OTHER INFORMATION: linker peptide

<400> SEQUENCE: 199

Gly Ser Ser Gly Gly Ser Gly Gly Ser Gly Gly Ser Gly
1               5                   10

<210> SEQ ID NO 200
<211> LENGTH: 11
<212> TYPE: PRT
<213> ORGANISM: Artificial Sequence
<220> FEATURE:
<223> OTHER INFORMATION: linker peptide

<400> SEQUENCE: 200

Gly Ser Ser Gly Gly Ser Gly Gly Ser Gly Gly
1               5                   10

<210> SEQ ID NO 201
<211> LENGTH: 12
<212> TYPE: PRT
<213> ORGANISM: Artificial Sequence
<220> FEATURE:
<223> OTHER INFORMATION: linker peptide

<400> SEQUENCE: 201

Gly Ser Ser Gly Gly Ser Gly Gly Ser Gly Gly Ser
1               5                   10

<210> SEQ ID NO 202
<211> LENGTH: 16
<212> TYPE: PRT
<213> ORGANISM: Artificial Sequence
<220> FEATURE:
<223> OTHER INFORMATION: linker peptide

<400> SEQUENCE: 202

Gly Ser Ser Gly Gly Ser Gly Gly Ser Gly Gly Ser Gly Gly Gly Ser
1               5                   10                  15

<210> SEQ ID NO 203
<211> LENGTH: 10
<212> TYPE: PRT
<213> ORGANISM: Artificial Sequence
<220> FEATURE:
<223> OTHER INFORMATION: linker peptide

<400> SEQUENCE: 203

Gly Ser Ser Gly Gly Ser Gly Gly Ser Gly
1               5                   10

<210> SEQ ID NO 204
<211> LENGTH: 11
<212> TYPE: PRT
<213> ORGANISM: Artificial Sequence
<220> FEATURE:
<223> OTHER INFORMATION: linker peptide

<400> SEQUENCE: 204

Gly Ser Ser Gly Gly Ser Gly Gly Ser Gly Ser
1               5                   10

```
<210> SEQ ID NO 205
<211> LENGTH: 4
<212> TYPE: PRT
<213> ORGANISM: Artificial Sequence
<220> FEATURE:
<223> OTHER INFORMATION: linker peptide

<400> SEQUENCE: 205

Gly Gly Gly Ser
1

<210> SEQ ID NO 206
<211> LENGTH: 5
<212> TYPE: PRT
<213> ORGANISM: Artificial Sequence
<220> FEATURE:
<223> OTHER INFORMATION: linker peptide

<400> SEQUENCE: 206

Gly Ser Ser Gly Thr
1               5

<210> SEQ ID NO 207
<211> LENGTH: 4
<212> TYPE: PRT
<213> ORGANISM: Artificial Sequence
<220> FEATURE:
<223> OTHER INFORMATION: linker peptide

<400> SEQUENCE: 207

Gly Ser Ser Gly
1

<210> SEQ ID NO 208
<211> LENGTH: 15
<212> TYPE: PRT
<213> ORGANISM: Artificial Sequence
<220> FEATURE:
<223> OTHER INFORMATION: masking moiety

<400> SEQUENCE: 208

Tyr Cys Glu Val Ser Glu Leu Phe Val Leu Pro Trp Cys Met Gly
1               5                   10                  15

<210> SEQ ID NO 209
<211> LENGTH: 11
<212> TYPE: PRT
<213> ORGANISM: Artificial Sequence
<220> FEATURE:
<223> OTHER INFORMATION: C5H9, C5B10, C5E10, G12H9, C5H9 v2 VL CDR1

<400> SEQUENCE: 209

Arg Ala Ser Gln Ser Ile Ser Ser Tyr Leu Asn
1               5                   10

<210> SEQ ID NO 210

<400> SEQUENCE: 210

000

<210> SEQ ID NO 211

<400> SEQUENCE: 211

000
```

```
<210> SEQ ID NO 212
<211> LENGTH: 5
<212> TYPE: PRT
<213> ORGANISM: Artificial Sequence
<220> FEATURE:
<223> OTHER INFORMATION: C5H9, C5B10, C5E10, G12H9, C5H9 v2 VH CDR1

<400> SEQUENCE: 212

Ser Tyr Ala Met Ser
1               5

<210> SEQ ID NO 213

<400> SEQUENCE: 213

000

<210> SEQ ID NO 214

<400> SEQUENCE: 214

000

<210> SEQ ID NO 215
<211> LENGTH: 7
<212> TYPE: PRT
<213> ORGANISM: Artificial Sequence
<220> FEATURE:
<223> OTHER INFORMATION: C5H9 v2 VL CDR2

<400> SEQUENCE: 215

Ala Ala Ser Ser Leu Gln Ser
1               5

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221
```

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227
<211> LENGTH: 7
<212> TYPE: PRT
<213> ORGANISM: Artificial Sequence
<220> FEATURE:
<223> OTHER INFORMATION: C5H9, C5B10, C5E10, G12H9 VL CDR2

<400> SEQUENCE: 227

Tyr Ala Ser Thr Leu Gln Ser
1               5

<210> SEQ ID NO 228
<211> LENGTH: 7
<212> TYPE: PRT
<213> ORGANISM: Artificial Sequence
<220> FEATURE:
<223> OTHER INFORMATION: C5H9, C5B10, C5E10, G12H9, C5H9 v2 VL CDR3

<400> SEQUENCE: 228

Asp Asn Gly Tyr Pro Ser Thr
1               5

<210> SEQ ID NO 229

<400> SEQUENCE: 229

000

<210> SEQ ID NO 230

<400> SEQUENCE: 230

000

```
<210> SEQ ID NO 231
<400> SEQUENCE: 231

000

<210> SEQ ID NO 232
<400> SEQUENCE: 232

000

<210> SEQ ID NO 233
<400> SEQUENCE: 233

000

<210> SEQ ID NO 234
<400> SEQUENCE: 234

000

<210> SEQ ID NO 235
<211> LENGTH: 7
<212> TYPE: PRT
<213> ORGANISM: Artificial Sequence
<220> FEATURE:
<223> OTHER INFORMATION: C5H9, G12H9, C5H9 v2 VH CDR3

<400> SEQUENCE: 235

Trp Ser Ala Ala Phe Asp Tyr
1               5

<210> SEQ ID NO 236
<211> LENGTH: 7
<212> TYPE: PRT
<213> ORGANISM: Artificial Sequence
<220> FEATURE:
<223> OTHER INFORMATION: C5B10 VH CDR3

<400> SEQUENCE: 236

Trp Ser Ala Gly Tyr Asp Tyr
1               5

<210> SEQ ID NO 237
<211> LENGTH: 7
<212> TYPE: PRT
<213> ORGANISM: Artificial Sequence
<220> FEATURE:
<223> OTHER INFORMATION: C5E10 VH CDR3

<400> SEQUENCE: 237

Trp Ser Lys Gly Phe Asp Tyr
1               5

<210> SEQ ID NO 238
<400> SEQUENCE: 238

000

<210> SEQ ID NO 239
<400> SEQUENCE: 239

000
```

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246
<211> LENGTH: 15
<212> TYPE: PRT
<213> ORGANISM: Artificial Sequence
<220> FEATURE:
<223> OTHER INFORMATION: C5H9, C5B10, C5E10, C5H9 v2 VH CDR2

<400> SEQUENCE: 246

Ser Ser Ile Trp Arg Asn Gly Ile Val Thr Val Tyr Ala Asp Ser
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: G12H9 VH CDR2

<400> SEQUENCE: 247

Ser Ser Ile Trp Tyr Gln Gly Leu Val Thr Val Tyr Ala Asp Ser
1               5                   10                  15

<210> SEQ ID NO 248

<400> SEQUENCE: 248

000

<210> SEQ ID NO 249

```
<400> SEQUENCE: 249
000

<210> SEQ ID NO 250
<400> SEQUENCE: 250
000

<210> SEQ ID NO 251
<400> SEQUENCE: 251
000

<210> SEQ ID NO 252
<400> SEQUENCE: 252
000

<210> SEQ ID NO 253
<400> SEQUENCE: 253
000

<210> SEQ ID NO 254
<400> SEQUENCE: 254
000

<210> SEQ ID NO 255
<400> SEQUENCE: 255
000

<210> SEQ ID NO 256
<400> SEQUENCE: 256
000

<210> SEQ ID NO 257
<400> SEQUENCE: 257
000

<210> SEQ ID NO 258
<400> SEQUENCE: 258
000

<210> SEQ ID NO 259
<400> SEQUENCE: 259
000

<210> SEQ ID NO 260
<400> SEQUENCE: 260
```

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

```
<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294
```

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

```
<210> SEQ ID NO 317
<400> SEQUENCE: 317
000

<210> SEQ ID NO 318
<400> SEQUENCE: 318
000

<210> SEQ ID NO 319
<400> SEQUENCE: 319
000

<210> SEQ ID NO 320
<400> SEQUENCE: 320
000

<210> SEQ ID NO 321
<400> SEQUENCE: 321
000

<210> SEQ ID NO 322
<400> SEQUENCE: 322
000

<210> SEQ ID NO 323
<400> SEQUENCE: 323
000

<210> SEQ ID NO 324
<400> SEQUENCE: 324
000

<210> SEQ ID NO 325
<400> SEQUENCE: 325
000

<210> SEQ ID NO 326
<400> SEQUENCE: 326
000

<210> SEQ ID NO 327
<400> SEQUENCE: 327
000

<210> SEQ ID NO 328
```

```
<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338
<211> LENGTH: 8
<212> TYPE: PRT
<213> ORGANISM: Artificial Sequence
<220> FEATURE:
<223> OTHER INFORMATION: cleavable moiety

<400> SEQUENCE: 338

Thr Gly Arg Gly Pro Ser Trp Val
1               5
```

<210> SEQ ID NO 339

<400> SEQUENCE: 339

000

<210> SEQ ID NO 340
<211> LENGTH: 8
<212> TYPE: PRT
<213> ORGANISM: Artificial Sequence
<220> FEATURE:
<223> OTHER INFORMATION: cleavable moiety

<400> SEQUENCE: 340

Thr Ala Arg Gly Pro Ser Phe Lys
1               5

<210> SEQ ID NO 341
<211> LENGTH: 8
<212> TYPE: PRT
<213> ORGANISM: Artificial Sequence
<220> FEATURE:
<223> OTHER INFORMATION: cleavable moiety

<400> SEQUENCE: 341

Leu Ser Gly Arg Ser Asp Asn His
1               5

<210> SEQ ID NO 342

<400> SEQUENCE: 342

000

<210> SEQ ID NO 343

<400> SEQUENCE: 343

000

<210> SEQ ID NO 344
<211> LENGTH: 8
<212> TYPE: PRT
<213> ORGANISM: Artificial Sequence
<220> FEATURE:
<223> OTHER INFORMATION: cleavable moiety

<400> SEQUENCE: 344

Pro Leu Thr Gly Arg Ser Gly Gly
1               5

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352
<211> LENGTH: 10
<212> TYPE: PRT
<213> ORGANISM: Artificial Sequence
<220> FEATURE:
<223> OTHER INFORMATION: cleavable moiety

<400> SEQUENCE: 352

Val His Met Pro Leu Gly Phe Leu Gly Pro
1               5                   10

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

```
<210> SEQ ID NO 358

<400> SEQUENCE: 358

000

<210> SEQ ID NO 359
<211> LENGTH: 8
<212> TYPE: PRT
<213> ORGANISM: Artificial Sequence
<220> FEATURE:
<223> OTHER INFORMATION: cleavable moiety

<400> SEQUENCE: 359

Gln Asn Gln Ala Leu Arg Met Ala
1               5

<210> SEQ ID NO 360
<211> LENGTH: 8
<212> TYPE: PRT
<213> ORGANISM: Artificial Sequence
<220> FEATURE:
<223> OTHER INFORMATION: cleavable moiety

<400> SEQUENCE: 360

Ala Gln Asn Leu Leu Gly Met Val
1               5

<210> SEQ ID NO 361
<211> LENGTH: 8
<212> TYPE: PRT
<213> ORGANISM: Artificial Sequence
<220> FEATURE:
<223> OTHER INFORMATION: cleavable moiety

<400> SEQUENCE: 361

Ser Thr Phe Pro Phe Gly Met Phe
1               5

<210> SEQ ID NO 362

<400> SEQUENCE: 362

000

<210> SEQ ID NO 363

<400> SEQUENCE: 363

000

<210> SEQ ID NO 364
<211> LENGTH: 8
<212> TYPE: PRT
<213> ORGANISM: Artificial Sequence
<220> FEATURE:
<223> OTHER INFORMATION: cleavable moiety

<400> SEQUENCE: 364

Ile Ser Ser Gly Leu Leu Ser Ser
1               5

<210> SEQ ID NO 365

<400> SEQUENCE: 365

000
```

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371
<211> LENGTH: 8
<212> TYPE: PRT
<213> ORGANISM: Artificial Sequence
<220> FEATURE:
<223> OTHER INFORMATION: cleavable moiety

<400> SEQUENCE: 371

Leu Ala Ala Pro Leu Gly Leu Leu
1               5

<210> SEQ ID NO 372
<211> LENGTH: 8
<212> TYPE: PRT
<213> ORGANISM: Artificial Sequence
<220> FEATURE:
<223> OTHER INFORMATION: cleavable moiety

<400> SEQUENCE: 372

Ala Val Gly Leu Leu Ala Pro Pro
1               5

<210> SEQ ID NO 373

<400> SEQUENCE: 373

000

<210> SEQ ID NO 374
<211> LENGTH: 8
<212> TYPE: PRT
<213> ORGANISM: Artificial Sequence
<220> FEATURE:
<223> OTHER INFORMATION: cleavable moiety

<400> SEQUENCE: 374

Pro Ala Gly Leu Trp Leu Asp Pro
1               5

<210> SEQ ID NO 375

<400> SEQUENCE: 375

000

<210> SEQ ID NO 376

<400> SEQUENCE: 376

000

<210> SEQ ID NO 377
<211> LENGTH: 13
<212> TYPE: PRT
<213> ORGANISM: Artificial Sequence
<220> FEATURE:
<223> OTHER INFORMATION: cleavable moiety

<400> SEQUENCE: 377

Ile Ser Ser Gly Leu Leu Ser Gly Arg Ser Asp Asn His
1               5                   10

<210> SEQ ID NO 378
<211> LENGTH: 22
<212> TYPE: PRT
<213> ORGANISM: Artificial Sequence
<220> FEATURE:
<223> OTHER INFORMATION: cleavable moiety

<400> SEQUENCE: 378

Ile Ser Ser Gly Leu Leu Ser Ser Gly Gly Ser Gly Gly Ser Leu Ser
1               5                   10                  15

Gly Arg Ser Asp Asn His
            20

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383
<211> LENGTH: 18
<212> TYPE: PRT
<213> ORGANISM: Artificial Sequence

```
<220> FEATURE:
<223> OTHER INFORMATION: cleavable moiety

<400> SEQUENCE: 383

Ala Val Gly Leu Leu Ala Pro Pro Gly Gly Leu Ser Gly Arg Ser Asp
1               5                   10                  15
Asn His

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000
```

```
<210> SEQ ID NO 394

<400> SEQUENCE: 394

000

<210> SEQ ID NO 395
<211> LENGTH: 6
<212> TYPE: PRT
<213> ORGANISM: Artificial Sequence
<220> FEATURE:
<223> OTHER INFORMATION: spacer peptide

<400> SEQUENCE: 395

Gly Gln Ser Gly Gln Gly
1               5

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404
```

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416
<400> SEQUENCE: 416
000

<210> SEQ ID NO 417
<400> SEQUENCE: 417
000

<210> SEQ ID NO 418
<400> SEQUENCE: 418
000

<210> SEQ ID NO 419
<400> SEQUENCE: 419
000

<210> SEQ ID NO 420
<400> SEQUENCE: 420
000

<210> SEQ ID NO 421
<400> SEQUENCE: 421
000

<210> SEQ ID NO 422
<400> SEQUENCE: 422
000

<210> SEQ ID NO 423
<400> SEQUENCE: 423
000

<210> SEQ ID NO 424
<400> SEQUENCE: 424
000

<210> SEQ ID NO 425
<400> SEQUENCE: 425
000

<210> SEQ ID NO 426
<211> LENGTH: 15
<212> TYPE: PRT
<213> ORGANISM: Artificial Sequence
<220> FEATURE:

```
-continued
```

<223> OTHER INFORMATION: masking moiety

<400> SEQUENCE: 426

Ser Cys Leu Met His Pro His Tyr Ala His Asp Tyr Cys Tyr Val
1               5                   10                  15

<210> SEQ ID NO 427

<400> SEQUENCE: 427

000

<210> SEQ ID NO 428
<211> LENGTH: 264
<212> TYPE: PRT
<213> ORGANISM: Artificial Sequence
<220> FEATURE:
<223> OTHER INFORMATION: PL07-2001-C5H9v2 Light Chain Sequence

<400> SEQUENCE: 428

Gln Gly Gln Ser Gly Ser Gly Ile Ala Leu Cys Pro Ser His Phe Cys
1               5                   10                  15

Gln Leu Pro Gln Thr Gly Gly Gly Ser Ser Gly Gly Ser Gly Gly Ser
                20                  25                  30

Gly Gly Ile Ser Ser Gly Leu Leu Ser Gly Arg Ser Asp Asn His Gly
            35                  40                  45

Gly Ser Asp Ile Gln Met Thr Gln Ser Pro Ser Ser Leu Ser Ala Ser
        50                  55                  60

Val Gly Asp Arg Val Thr Ile Thr Cys Arg Ala Ser Gln Ser Ile Ser
65                  70                  75                  80

Ser Tyr Leu Asn Trp Tyr Gln Gln Lys Pro Gly Lys Ala Pro Lys Leu
                85                  90                  95

Leu Ile Tyr Ala Ala Ser Ser Leu Gln Ser Gly Val Pro Ser Arg Phe
                100                 105                 110

Ser Gly Ser Gly Ser Gly Thr Asp Phe Thr Leu Thr Ile Ser Ser Leu
            115                 120                 125

Gln Pro Glu Asp Phe Ala Thr Tyr Tyr Cys Gln Gln Asp Asn Gly Tyr
        130                 135                 140

Pro Ser Thr Phe Gly Gly Gly Thr Lys Val Glu Ile Lys Arg Thr Val
145                 150                 155                 160

Ala Ala Pro Ser Val Phe Ile Phe Pro Pro Ser Asp Glu Gln Leu Lys
                165                 170                 175

Ser Gly Thr Ala Ser Val Val Cys Leu Leu Asn Asn Phe Tyr Pro Arg
            180                 185                 190

Glu Ala Lys Val Gln Trp Lys Val Asp Asn Ala Leu Gln Ser Gly Asn
        195                 200                 205

Ser Gln Glu Ser Val Thr Glu Gln Asp Ser Lys Asp Ser Thr Tyr Ser
    210                 215                 220

Leu Ser Ser Thr Leu Thr Leu Ser Lys Ala Asp Tyr Glu Lys His Lys
225                 230                 235                 240

Val Tyr Ala Cys Glu Val Thr His Gln Gly Leu Ser Ser Pro Val Thr
                245                 250                 255

Lys Ser Phe Asn Arg Gly Glu Cys
            260

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432
<211> LENGTH: 442
<212> TYPE: PRT
<213> ORGANISM: Artificial Sequence
<220> FEATURE:
<223> OTHER INFORMATION: PL07-2001-C5H9v2 Heavy Chain Sequence

<400> SEQUENCE: 432

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Trp Arg Asn Gly Ile Val Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ala Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
```

```
                    275                 280                 285
    Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
    305                 310                 315                 320

Asn Lys Gly Leu Pro Ser Ser Ile Glu Lys Thr Ile Ser Lys Ala Lys
                        325                 330                 335

Gly Gln Pro Arg Glu Pro Gln Val Tyr Thr Leu Pro Pro Ser Gln Glu
                    340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
    385                 390                 395                 400

Phe Leu Tyr Ser Arg Leu Thr Val Asp Lys Ser Arg Trp Gln Glu Gly
                    405                 410                 415

Asn Val Phe Ser Cys Ser Val Met His Glu Ala Leu His Asn His Tyr
                420                 425                 430

Thr Gln Lys Ser Leu Ser Leu Ser Leu Gly
                435                 440

<210> SEQ ID NO 433

<400> SEQUENCE: 433

000

<210> SEQ ID NO 434

<400> SEQUENCE: 434

000

<210> SEQ ID NO 435
<211> LENGTH: 12
<212> TYPE: PRT
<213> ORGANISM: Artificial Sequence
<220> FEATURE:
<223> OTHER INFORMATION: cleavable moiety

<400> SEQUENCE: 435

Asn Thr Leu Ser Gly Arg Ser Glu Asn His Ser Gly
1               5                   10

<210> SEQ ID NO 436
<211> LENGTH: 12
<212> TYPE: PRT
<213> ORGANISM: Artificial Sequence
<220> FEATURE:
<223> OTHER INFORMATION: cleavable moiety

<400> SEQUENCE: 436

Asn Thr Leu Ser Gly Arg Ser Gly Asn His Gly Ser
1               5                   10

<210> SEQ ID NO 437
<211> LENGTH: 12
<212> TYPE: PRT
<213> ORGANISM: Artificial Sequence
<220> FEATURE:
<223> OTHER INFORMATION: cleavable moiety
```

<400> SEQUENCE: 437

Thr Ser Thr Ser Gly Arg Ser Ala Asn Pro Arg Gly
1               5                   10

<210> SEQ ID NO 438
<211> LENGTH: 8
<212> TYPE: PRT
<213> ORGANISM: Artificial Sequence
<220> FEATURE:
<223> OTHER INFORMATION: cleavable moiety

<400> SEQUENCE: 438

Thr Ser Gly Arg Ser Ala Asn Pro
1               5

<210> SEQ ID NO 439
<211> LENGTH: 8
<212> TYPE: PRT
<213> ORGANISM: Artificial Sequence
<220> FEATURE:
<223> OTHER INFORMATION: cleavable moiety

<400> SEQUENCE: 439

Val Ala Gly Arg Ser Met Arg Pro
1               5

<210> SEQ ID NO 440
<211> LENGTH: 8
<212> TYPE: PRT
<213> ORGANISM: Artificial Sequence
<220> FEATURE:
<223> OTHER INFORMATION: cleavable moiety

<400> SEQUENCE: 440

Val Val Pro Glu Gly Arg Arg Ser
1               5

<210> SEQ ID NO 441
<211> LENGTH: 8
<212> TYPE: PRT
<213> ORGANISM: Artificial Sequence
<220> FEATURE:
<223> OTHER INFORMATION: cleavable moiety

<400> SEQUENCE: 441

Ile Leu Pro Arg Ser Pro Ala Phe
1               5

<210> SEQ ID NO 442
<211> LENGTH: 8
<212> TYPE: PRT
<213> ORGANISM: Artificial Sequence
<220> FEATURE:
<223> OTHER INFORMATION: cleavable moiety

<400> SEQUENCE: 442

Met Val Leu Gly Arg Ser Leu Leu
1               5

<210> SEQ ID NO 443
<211> LENGTH: 8
<212> TYPE: PRT
<213> ORGANISM: Artificial Sequence
<220> FEATURE:
<223> OTHER INFORMATION: cleavable moiety

```
<400> SEQUENCE: 443

Gln Gly Arg Ala Ile Thr Phe Ile
1               5

<210> SEQ ID NO 444
<211> LENGTH: 8
<212> TYPE: PRT
<213> ORGANISM: Artificial Sequence
<220> FEATURE:
<223> OTHER INFORMATION: cleavable moiety

<400> SEQUENCE: 444

Ser Pro Arg Ser Ile Met Leu Ala
1               5

<210> SEQ ID NO 445
<211> LENGTH: 8
<212> TYPE: PRT
<213> ORGANISM: Artificial Sequence
<220> FEATURE:
<223> OTHER INFORMATION: cleavable moiety

<400> SEQUENCE: 445

Ser Met Leu Arg Ser Met Pro Leu
1               5

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000
```

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

```
<210> SEQ ID NO 464
<400> SEQUENCE: 464
000

<210> SEQ ID NO 465
<400> SEQUENCE: 465
000

<210> SEQ ID NO 466
<400> SEQUENCE: 466
000

<210> SEQ ID NO 467
<400> SEQUENCE: 467
000

<210> SEQ ID NO 468
<400> SEQUENCE: 468
000

<210> SEQ ID NO 469
<400> SEQUENCE: 469
000

<210> SEQ ID NO 470
<400> SEQUENCE: 470
000

<210> SEQ ID NO 471
<400> SEQUENCE: 471
000

<210> SEQ ID NO 472
<400> SEQUENCE: 472
000

<210> SEQ ID NO 473
<400> SEQUENCE: 473
000

<210> SEQ ID NO 474
<400> SEQUENCE: 474
000

<210> SEQ ID NO 475
```

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487
<400> SEQUENCE: 487
000

<210> SEQ ID NO 488
<400> SEQUENCE: 488
000

<210> SEQ ID NO 489
<400> SEQUENCE: 489
000

<210> SEQ ID NO 490
<400> SEQUENCE: 490
000

<210> SEQ ID NO 491
<400> SEQUENCE: 491
000

<210> SEQ ID NO 492
<400> SEQUENCE: 492
000

<210> SEQ ID NO 493
<400> SEQUENCE: 493
000

<210> SEQ ID NO 494
<400> SEQUENCE: 494
000

<210> SEQ ID NO 495
<400> SEQUENCE: 495
000

<210> SEQ ID NO 496
<400> SEQUENCE: 496
000

<210> SEQ ID NO 497
<400> SEQUENCE: 497
000

```
<210> SEQ ID NO 498
<400> SEQUENCE: 498
000

<210> SEQ ID NO 499
<400> SEQUENCE: 499
000

<210> SEQ ID NO 500
<400> SEQUENCE: 500
000

<210> SEQ ID NO 501
<400> SEQUENCE: 501
000

<210> SEQ ID NO 502
<400> SEQUENCE: 502
000

<210> SEQ ID NO 503
<400> SEQUENCE: 503
000

<210> SEQ ID NO 504
<400> SEQUENCE: 504
000

<210> SEQ ID NO 505
<400> SEQUENCE: 505
000

<210> SEQ ID NO 506
<400> SEQUENCE: 506
000

<210> SEQ ID NO 507
<400> SEQUENCE: 507
000

<210> SEQ ID NO 508
<400> SEQUENCE: 508
000

<210> SEQ ID NO 509
```

```
<400> SEQUENCE: 509
000

<210> SEQ ID NO 510
<400> SEQUENCE: 510
000

<210> SEQ ID NO 511
<400> SEQUENCE: 511
000

<210> SEQ ID NO 512
<400> SEQUENCE: 512
000

<210> SEQ ID NO 513
<400> SEQUENCE: 513
000

<210> SEQ ID NO 514
<400> SEQUENCE: 514
000

<210> SEQ ID NO 515
<400> SEQUENCE: 515
000

<210> SEQ ID NO 516
<400> SEQUENCE: 516
000

<210> SEQ ID NO 517
<400> SEQUENCE: 517
000

<210> SEQ ID NO 518
<400> SEQUENCE: 518
000

<210> SEQ ID NO 519
<400> SEQUENCE: 519
000

<210> SEQ ID NO 520
<400> SEQUENCE: 520
```

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

```
<210> SEQ ID NO 532
<400> SEQUENCE: 532
000

<210> SEQ ID NO 533
<400> SEQUENCE: 533
000

<210> SEQ ID NO 534
<400> SEQUENCE: 534
000

<210> SEQ ID NO 535
<400> SEQUENCE: 535
000

<210> SEQ ID NO 536
<400> SEQUENCE: 536
000

<210> SEQ ID NO 537
<400> SEQUENCE: 537
000

<210> SEQ ID NO 538
<400> SEQUENCE: 538
000

<210> SEQ ID NO 539
<400> SEQUENCE: 539
000

<210> SEQ ID NO 540
<400> SEQUENCE: 540
000

<210> SEQ ID NO 541
<400> SEQUENCE: 541
000

<210> SEQ ID NO 542
<400> SEQUENCE: 542
000
```

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

```
<210> SEQ ID NO 577
<400> SEQUENCE: 577
000

<210> SEQ ID NO 578
<400> SEQUENCE: 578
000

<210> SEQ ID NO 579
<400> SEQUENCE: 579
000

<210> SEQ ID NO 580
<400> SEQUENCE: 580
000

<210> SEQ ID NO 581
<400> SEQUENCE: 581
000

<210> SEQ ID NO 582
<400> SEQUENCE: 582
000

<210> SEQ ID NO 583
<400> SEQUENCE: 583
000

<210> SEQ ID NO 584
<400> SEQUENCE: 584
000

<210> SEQ ID NO 585
<400> SEQUENCE: 585
000

<210> SEQ ID NO 586
<400> SEQUENCE: 586
000

<210> SEQ ID NO 587
<400> SEQUENCE: 587
000

<210> SEQ ID NO 588
```

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

-continued

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

```
<210> SEQ ID NO 622
<400> SEQUENCE: 622
000

<210> SEQ ID NO 623
<400> SEQUENCE: 623
000

<210> SEQ ID NO 624
<400> SEQUENCE: 624
000

<210> SEQ ID NO 625
<400> SEQUENCE: 625
000

<210> SEQ ID NO 626
<400> SEQUENCE: 626
000

<210> SEQ ID NO 627
<400> SEQUENCE: 627
000

<210> SEQ ID NO 628
<400> SEQUENCE: 628
000

<210> SEQ ID NO 629
<400> SEQUENCE: 629
000

<210> SEQ ID NO 630
<400> SEQUENCE: 630
000

<210> SEQ ID NO 631
<400> SEQUENCE: 631
000

<210> SEQ ID NO 632
<400> SEQUENCE: 632
000

<210> SEQ ID NO 633
```

```
<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644
```

000

<210> SEQ ID NO 645
<400> SEQUENCE: 645
000

<210> SEQ ID NO 646
<400> SEQUENCE: 646
000

<210> SEQ ID NO 647
<400> SEQUENCE: 647
000

<210> SEQ ID NO 648
<400> SEQUENCE: 648
000

<210> SEQ ID NO 649
<400> SEQUENCE: 649
000

<210> SEQ ID NO 650
<400> SEQUENCE: 650
000

<210> SEQ ID NO 651
<400> SEQUENCE: 651
000

<210> SEQ ID NO 652
<400> SEQUENCE: 652
000

<210> SEQ ID NO 653
<400> SEQUENCE: 653
000

<210> SEQ ID NO 654
<400> SEQUENCE: 654
000

<210> SEQ ID NO 655
<400> SEQUENCE: 655
000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

```
<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678
```

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700

<400> SEQUENCE: 700

000

<210> SEQ ID NO 701

<400> SEQUENCE: 701

000

<210> SEQ ID NO 702

<400> SEQUENCE: 702

000

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

<210> SEQ ID NO 711

<400> SEQUENCE: 711

000

<210> SEQ ID NO 712

<400> SEQUENCE: 712

000

<210> SEQ ID NO 713

<400> SEQUENCE: 713

000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724
<400> SEQUENCE: 724
000

<210> SEQ ID NO 725
<400> SEQUENCE: 725
000

<210> SEQ ID NO 726
<400> SEQUENCE: 726
000

<210> SEQ ID NO 727
<400> SEQUENCE: 727
000

<210> SEQ ID NO 728
<400> SEQUENCE: 728
000

<210> SEQ ID NO 729
<400> SEQUENCE: 729
000

<210> SEQ ID NO 730
<400> SEQUENCE: 730
000

<210> SEQ ID NO 731
<400> SEQUENCE: 731
000

<210> SEQ ID NO 732
<400> SEQUENCE: 732
000

<210> SEQ ID NO 733
<400> SEQUENCE: 733
000

<210> SEQ ID NO 734
<400> SEQUENCE: 734
000

<210> SEQ ID NO 735
<400> SEQUENCE: 735
000

<210> SEQ ID NO 736
<400> SEQUENCE: 736
000

<210> SEQ ID NO 737
<400> SEQUENCE: 737
000

<210> SEQ ID NO 738
<400> SEQUENCE: 738
000

<210> SEQ ID NO 739
<400> SEQUENCE: 739
000

<210> SEQ ID NO 740
<400> SEQUENCE: 740
000

<210> SEQ ID NO 741
<400> SEQUENCE: 741
000

<210> SEQ ID NO 742
<400> SEQUENCE: 742
000

<210> SEQ ID NO 743
<400> SEQUENCE: 743
000

<210> SEQ ID NO 744
<400> SEQUENCE: 744
000

<210> SEQ ID NO 745
<400> SEQUENCE: 745
000

<210> SEQ ID NO 746

<400> SEQUENCE: 746

000

<210> SEQ ID NO 747

<400> SEQUENCE: 747

000

<210> SEQ ID NO 748

<400> SEQUENCE: 748

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

<400> SEQUENCE: 754

000

<210> SEQ ID NO 755

<400> SEQUENCE: 755

000

<210> SEQ ID NO 756

<400> SEQUENCE: 756

000

<210> SEQ ID NO 757

<400> SEQUENCE: 757

000

<210> SEQ ID NO 758
<400> SEQUENCE: 758
000

<210> SEQ ID NO 759
<400> SEQUENCE: 759
000

<210> SEQ ID NO 760
<400> SEQUENCE: 760
000

<210> SEQ ID NO 761
<400> SEQUENCE: 761
000

<210> SEQ ID NO 762
<400> SEQUENCE: 762
000

<210> SEQ ID NO 763
<400> SEQUENCE: 763
000

<210> SEQ ID NO 764
<400> SEQUENCE: 764
000

<210> SEQ ID NO 765
<400> SEQUENCE: 765
000

<210> SEQ ID NO 766
<400> SEQUENCE: 766
000

<210> SEQ ID NO 767
<400> SEQUENCE: 767
000

<210> SEQ ID NO 768
<400> SEQUENCE: 768
000

<210> SEQ ID NO 769

<400> SEQUENCE: 769

000

<210> SEQ ID NO 770

<400> SEQUENCE: 770

000

<210> SEQ ID NO 771

<400> SEQUENCE: 771

000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

<210> SEQ ID NO 779

<400> SEQUENCE: 779

000

```
<210> SEQ ID NO 780
<400> SEQUENCE: 780
000

<210> SEQ ID NO 781
<400> SEQUENCE: 781
000

<210> SEQ ID NO 782
<400> SEQUENCE: 782
000

<210> SEQ ID NO 783
<400> SEQUENCE: 783
000

<210> SEQ ID NO 784
<400> SEQUENCE: 784
000

<210> SEQ ID NO 785
<400> SEQUENCE: 785
000

<210> SEQ ID NO 786
<400> SEQUENCE: 786
000

<210> SEQ ID NO 787
<400> SEQUENCE: 787
000

<210> SEQ ID NO 788
<400> SEQUENCE: 788
000

<210> SEQ ID NO 789
<400> SEQUENCE: 789
000

<210> SEQ ID NO 790
<400> SEQUENCE: 790
000

<210> SEQ ID NO 791
```

```
<400> SEQUENCE: 791
000

<210> SEQ ID NO 792
<400> SEQUENCE: 792
000

<210> SEQ ID NO 793
<400> SEQUENCE: 793
000

<210> SEQ ID NO 794
<400> SEQUENCE: 794
000

<210> SEQ ID NO 795
<400> SEQUENCE: 795
000

<210> SEQ ID NO 796
<400> SEQUENCE: 796
000

<210> SEQ ID NO 797
<400> SEQUENCE: 797
000

<210> SEQ ID NO 798
<400> SEQUENCE: 798
000

<210> SEQ ID NO 799
<400> SEQUENCE: 799
000

<210> SEQ ID NO 800
<400> SEQUENCE: 800
000

<210> SEQ ID NO 801
<400> SEQUENCE: 801
000

<210> SEQ ID NO 802
<400> SEQUENCE: 802
```

000

<210> SEQ ID NO 803
<400> SEQUENCE: 803
000

<210> SEQ ID NO 804
<400> SEQUENCE: 804
000

<210> SEQ ID NO 805
<400> SEQUENCE: 805
000

<210> SEQ ID NO 806
<400> SEQUENCE: 806
000

<210> SEQ ID NO 807
<400> SEQUENCE: 807
000

<210> SEQ ID NO 808
<400> SEQUENCE: 808
000

<210> SEQ ID NO 809
<400> SEQUENCE: 809
000

<210> SEQ ID NO 810
<400> SEQUENCE: 810
000

<210> SEQ ID NO 811
<400> SEQUENCE: 811
000

<210> SEQ ID NO 812
<400> SEQUENCE: 812
000

<210> SEQ ID NO 813
<400> SEQUENCE: 813
000

-continued

```
<210> SEQ ID NO 814
<400> SEQUENCE: 814
000

<210> SEQ ID NO 815
<400> SEQUENCE: 815
000

<210> SEQ ID NO 816
<400> SEQUENCE: 816
000

<210> SEQ ID NO 817
<400> SEQUENCE: 817
000

<210> SEQ ID NO 818
<400> SEQUENCE: 818
000

<210> SEQ ID NO 819
<400> SEQUENCE: 819
000

<210> SEQ ID NO 820
<400> SEQUENCE: 820
000

<210> SEQ ID NO 821
<400> SEQUENCE: 821
000

<210> SEQ ID NO 822
<400> SEQUENCE: 822
000

<210> SEQ ID NO 823
<400> SEQUENCE: 823
000

<210> SEQ ID NO 824
<400> SEQUENCE: 824
000

<210> SEQ ID NO 825
```

<400> SEQUENCE: 825

000

<210> SEQ ID NO 826

<400> SEQUENCE: 826

000

<210> SEQ ID NO 827

<400> SEQUENCE: 827

000

<210> SEQ ID NO 828

<400> SEQUENCE: 828

000

<210> SEQ ID NO 829

<400> SEQUENCE: 829

000

<210> SEQ ID NO 830

<400> SEQUENCE: 830

000

<210> SEQ ID NO 831

<400> SEQUENCE: 831

000

<210> SEQ ID NO 832

<400> SEQUENCE: 832

000

<210> SEQ ID NO 833

<400> SEQUENCE: 833

000

<210> SEQ ID NO 834

<400> SEQUENCE: 834

000

<210> SEQ ID NO 835

<400> SEQUENCE: 835

000

<210> SEQ ID NO 836

<400> SEQUENCE: 836

000

<210> SEQ ID NO 837

<400> SEQUENCE: 837

000

<210> SEQ ID NO 838

<400> SEQUENCE: 838

000

<210> SEQ ID NO 839

<400> SEQUENCE: 839

000

<210> SEQ ID NO 840

<400> SEQUENCE: 840

000

<210> SEQ ID NO 841

<400> SEQUENCE: 841

000

<210> SEQ ID NO 842

<400> SEQUENCE: 842

000

<210> SEQ ID NO 843

<400> SEQUENCE: 843

000

<210> SEQ ID NO 844

<400> SEQUENCE: 844

000

<210> SEQ ID NO 845

<400> SEQUENCE: 845

000

<210> SEQ ID NO 846

<400> SEQUENCE: 846

000

<210> SEQ ID NO 847

<400> SEQUENCE: 847

000

<210> SEQ ID NO 848

<400> SEQUENCE: 848

000

<210> SEQ ID NO 849

<400> SEQUENCE: 849

000

<210> SEQ ID NO 850

<400> SEQUENCE: 850

000

<210> SEQ ID NO 851

<400> SEQUENCE: 851

000

<210> SEQ ID NO 852

<400> SEQUENCE: 852

000

<210> SEQ ID NO 853

<400> SEQUENCE: 853

000

<210> SEQ ID NO 854

<400> SEQUENCE: 854

000

<210> SEQ ID NO 855

<400> SEQUENCE: 855

000

<210> SEQ ID NO 856

<400> SEQUENCE: 856

000

<210> SEQ ID NO 857

<400> SEQUENCE: 857

000

<210> SEQ ID NO 858

<400> SEQUENCE: 858

000

-continued

<210> SEQ ID NO 859
<400> SEQUENCE: 859
000

<210> SEQ ID NO 860
<400> SEQUENCE: 860
000

<210> SEQ ID NO 861
<400> SEQUENCE: 861
000

<210> SEQ ID NO 862
<400> SEQUENCE: 862
000

<210> SEQ ID NO 863
<400> SEQUENCE: 863
000

<210> SEQ ID NO 864
<400> SEQUENCE: 864
000

<210> SEQ ID NO 865
<400> SEQUENCE: 865
000

<210> SEQ ID NO 866
<400> SEQUENCE: 866
000

<210> SEQ ID NO 867
<400> SEQUENCE: 867
000

<210> SEQ ID NO 868
<400> SEQUENCE: 868
000

<210> SEQ ID NO 869
<400> SEQUENCE: 869
000

<210> SEQ ID NO 870

```
<400> SEQUENCE: 870

000

<210> SEQ ID NO 871

<400> SEQUENCE: 871

000

<210> SEQ ID NO 872

<400> SEQUENCE: 872

000

<210> SEQ ID NO 873

<400> SEQUENCE: 873

000

<210> SEQ ID NO 874

<400> SEQUENCE: 874

000

<210> SEQ ID NO 875

<400> SEQUENCE: 875

000

<210> SEQ ID NO 876

<400> SEQUENCE: 876

000

<210> SEQ ID NO 877

<400> SEQUENCE: 877

000

<210> SEQ ID NO 878

<400> SEQUENCE: 878

000

<210> SEQ ID NO 879

<400> SEQUENCE: 879

000

<210> SEQ ID NO 880

<400> SEQUENCE: 880

000

<210> SEQ ID NO 881

<400> SEQUENCE: 881
```

000

<210> SEQ ID NO 882

<400> SEQUENCE: 882

000

<210> SEQ ID NO 883
<211> LENGTH: 8
<212> TYPE: PRT
<213> ORGANISM: Artificial Sequence
<220> FEATURE:
<223> OTHER INFORMATION: cleavable moiety

<400> SEQUENCE: 883

Leu Ser Gly Arg Ser Gly Asn His
1               5

<210> SEQ ID NO 884
<211> LENGTH: 9
<212> TYPE: PRT
<213> ORGANISM: Artificial Sequence
<220> FEATURE:
<223> OTHER INFORMATION: cleavable moiety

<400> SEQUENCE: 884

Ser Gly Arg Ser Ala Asn Pro Arg Gly
1               5

<210> SEQ ID NO 885
<211> LENGTH: 8
<212> TYPE: PRT
<213> ORGANISM: Artificial Sequence
<220> FEATURE:
<223> OTHER INFORMATION: cleavable moiety

<400> SEQUENCE: 885

Leu Ser Gly Arg Ser Asp Asp His
1               5

<210> SEQ ID NO 886
<211> LENGTH: 8
<212> TYPE: PRT
<213> ORGANISM: Artificial Sequence
<220> FEATURE:
<223> OTHER INFORMATION: cleavable moiety

<400> SEQUENCE: 886

Leu Ser Gly Arg Ser Asp Ile His
1               5

<210> SEQ ID NO 887
<211> LENGTH: 8
<212> TYPE: PRT
<213> ORGANISM: Artificial Sequence
<220> FEATURE:
<223> OTHER INFORMATION: cleavable moiety

<400> SEQUENCE: 887

Leu Ser Gly Arg Ser Asp Gln His
1               5

<210> SEQ ID NO 888
<211> LENGTH: 8
<212> TYPE: PRT
<213> ORGANISM: Artificial Sequence

```
<220> FEATURE:
<223> OTHER INFORMATION: cleavable moiety

<400> SEQUENCE: 888

Leu Ser Gly Arg Ser Asp Thr His
1               5

<210> SEQ ID NO 889
<211> LENGTH: 8
<212> TYPE: PRT
<213> ORGANISM: Artificial Sequence
<220> FEATURE:
<223> OTHER INFORMATION: cleavable moiety

<400> SEQUENCE: 889

Leu Ser Gly Arg Ser Asp Tyr His
1               5

<210> SEQ ID NO 890
<211> LENGTH: 8
<212> TYPE: PRT
<213> ORGANISM: Artificial Sequence
<220> FEATURE:
<223> OTHER INFORMATION: cleavable moiety

<400> SEQUENCE: 890

Leu Ser Gly Arg Ser Asp Asn Pro
1               5

<210> SEQ ID NO 891
<211> LENGTH: 8
<212> TYPE: PRT
<213> ORGANISM: Artificial Sequence
<220> FEATURE:
<223> OTHER INFORMATION: cleavable moiety

<400> SEQUENCE: 891

Leu Ser Gly Arg Ser Ala Asn Pro
1               5

<210> SEQ ID NO 892
<211> LENGTH: 8
<212> TYPE: PRT
<213> ORGANISM: Artificial Sequence
<220> FEATURE:
<223> OTHER INFORMATION: cleavable moiety

<400> SEQUENCE: 892

Leu Ser Gly Arg Ser Ala Asn Ile
1               5

<210> SEQ ID NO 893
<211> LENGTH: 8
<212> TYPE: PRT
<213> ORGANISM: Artificial Sequence
<220> FEATURE:
<223> OTHER INFORMATION: cleavable moiety

<400> SEQUENCE: 893

Leu Ser Gly Arg Ser Asp Asn Ile
1               5

<210> SEQ ID NO 894
<211> LENGTH: 8
<212> TYPE: PRT
<213> ORGANISM: Artificial Sequence
<220> FEATURE:
```

```
<223> OTHER INFORMATION: cleavable moiety

<400> SEQUENCE: 894

Met Ile Ala Pro Val Ala Tyr Arg
1               5

<210> SEQ ID NO 895
<211> LENGTH: 8
<212> TYPE: PRT
<213> ORGANISM: Artificial Sequence
<220> FEATURE:
<223> OTHER INFORMATION: cleavable moiety

<400> SEQUENCE: 895

Arg Pro Ser Pro Met Trp Ala Tyr
1               5

<210> SEQ ID NO 896
<211> LENGTH: 8
<212> TYPE: PRT
<213> ORGANISM: Artificial Sequence
<220> FEATURE:
<223> OTHER INFORMATION: cleavable moiety

<400> SEQUENCE: 896

Trp Ala Thr Pro Arg Pro Met Arg
1               5

<210> SEQ ID NO 897
<211> LENGTH: 8
<212> TYPE: PRT
<213> ORGANISM: Artificial Sequence
<220> FEATURE:
<223> OTHER INFORMATION: cleavable moiety

<400> SEQUENCE: 897

Phe Arg Leu Leu Asp Trp Gln Trp
1               5

<210> SEQ ID NO 898
<211> LENGTH: 5
<212> TYPE: PRT
<213> ORGANISM: Artificial Sequence
<220> FEATURE:
<223> OTHER INFORMATION: cleavable moiety

<400> SEQUENCE: 898

Ile Ser Ser Gly Leu
1               5

<210> SEQ ID NO 899
<211> LENGTH: 7
<212> TYPE: PRT
<213> ORGANISM: Artificial Sequence
<220> FEATURE:
<223> OTHER INFORMATION: cleavable moiety

<400> SEQUENCE: 899

Ile Ser Ser Gly Leu Leu Ser
1               5

<210> SEQ ID NO 900
<211> LENGTH: 6
<212> TYPE: PRT
<213> ORGANISM: Artificial Sequence
<220> FEATURE:
<223> OTHER INFORMATION: cleavable moiety
```

```
<400> SEQUENCE: 900

Ile Ser Ser Gly Leu Leu
1               5

<210> SEQ ID NO 901
<211> LENGTH: 15
<212> TYPE: PRT
<213> ORGANISM: Artificial Sequence
<220> FEATURE:
<223> OTHER INFORMATION: cleavable moiety

<400> SEQUENCE: 901

Ile Ser Ser Gly Leu Leu Ser Gly Arg Ser Ala Asn Pro Arg Gly
1               5                   10                  15

<210> SEQ ID NO 902
<211> LENGTH: 18
<212> TYPE: PRT
<213> ORGANISM: Artificial Sequence
<220> FEATURE:
<223> OTHER INFORMATION: cleavable moiety

<400> SEQUENCE: 902

Ala Val Gly Leu Leu Ala Pro Pro Thr Ser Gly Arg Ser Ala Asn Pro
1               5                   10                  15

Arg Gly

<210> SEQ ID NO 903
<211> LENGTH: 17
<212> TYPE: PRT
<213> ORGANISM: Artificial Sequence
<220> FEATURE:
<223> OTHER INFORMATION: cleavable moiety

<400> SEQUENCE: 903

Ala Val Gly Leu Leu Ala Pro Pro Ser Gly Arg Ser Ala Asn Pro Arg
1               5                   10                  15

Gly

<210> SEQ ID NO 904
<211> LENGTH: 13
<212> TYPE: PRT
<213> ORGANISM: Artificial Sequence
<220> FEATURE:
<223> OTHER INFORMATION: cleavable moiety

<400> SEQUENCE: 904

Ile Ser Ser Gly Leu Leu Ser Gly Arg Ser Asp Asp His
1               5                   10

<210> SEQ ID NO 905
<211> LENGTH: 13
<212> TYPE: PRT
<213> ORGANISM: Artificial Sequence
<220> FEATURE:
<223> OTHER INFORMATION: cleavable moiety

<400> SEQUENCE: 905

Ile Ser Ser Gly Leu Leu Ser Gly Arg Ser Asp Ile His
1               5                   10

<210> SEQ ID NO 906
<211> LENGTH: 13
<212> TYPE: PRT
```

<213> ORGANISM: Artificial Sequence
<220> FEATURE:
<223> OTHER INFORMATION: cleavable moiety

<400> SEQUENCE: 906

Ile Ser Ser Gly Leu Leu Ser Gly Arg Ser Asp Gln His
1               5                   10

<210> SEQ ID NO 907
<211> LENGTH: 13
<212> TYPE: PRT
<213> ORGANISM: Artificial Sequence
<220> FEATURE:
<223> OTHER INFORMATION: cleavable moiety

<400> SEQUENCE: 907

Ile Ser Ser Gly Leu Leu Ser Gly Arg Ser Asp Thr His
1               5                   10

<210> SEQ ID NO 908
<211> LENGTH: 13
<212> TYPE: PRT
<213> ORGANISM: Artificial Sequence
<220> FEATURE:
<223> OTHER INFORMATION: cleavable moiety

<400> SEQUENCE: 908

Ile Ser Ser Gly Leu Leu Ser Gly Arg Ser Asp Tyr His
1               5                   10

<210> SEQ ID NO 909
<211> LENGTH: 13
<212> TYPE: PRT
<213> ORGANISM: Artificial Sequence
<220> FEATURE:
<223> OTHER INFORMATION: cleavable moiety

<400> SEQUENCE: 909

Ile Ser Ser Gly Leu Leu Ser Gly Arg Ser Asp Asn Pro
1               5                   10

<210> SEQ ID NO 910
<211> LENGTH: 13
<212> TYPE: PRT
<213> ORGANISM: Artificial Sequence
<220> FEATURE:
<223> OTHER INFORMATION: cleavable moiety

<400> SEQUENCE: 910

Ile Ser Ser Gly Leu Leu Ser Gly Arg Ser Ala Asn Pro
1               5                   10

<210> SEQ ID NO 911
<211> LENGTH: 13
<212> TYPE: PRT
<213> ORGANISM: Artificial Sequence
<220> FEATURE:
<223> OTHER INFORMATION: cleavable moiety

<400> SEQUENCE: 911

Ile Ser Ser Gly Leu Leu Ser Gly Arg Ser Ala Asn Ile
1               5                   10

<210> SEQ ID NO 912
<211> LENGTH: 18
<212> TYPE: PRT
<213> ORGANISM: Artificial Sequence

```
<220> FEATURE:
<223> OTHER INFORMATION: cleavable moiety

<400> SEQUENCE: 912

Ala Val Gly Leu Leu Ala Pro Pro Gly Gly Leu Ser Gly Arg Ser Asp
1               5                   10                  15

Asp His

<210> SEQ ID NO 913
<211> LENGTH: 18
<212> TYPE: PRT
<213> ORGANISM: Artificial Sequence
<220> FEATURE:
<223> OTHER INFORMATION: cleavable moiety

<400> SEQUENCE: 913

Ala Val Gly Leu Leu Ala Pro Pro Gly Gly Leu Ser Gly Arg Ser Asp
1               5                   10                  15

Ile His

<210> SEQ ID NO 914
<211> LENGTH: 18
<212> TYPE: PRT
<213> ORGANISM: Artificial Sequence
<220> FEATURE:
<223> OTHER INFORMATION: cleavable moiety

<400> SEQUENCE: 914

Ala Val Gly Leu Leu Ala Pro Pro Gly Gly Leu Ser Gly Arg Ser Asp
1               5                   10                  15

Gln His

<210> SEQ ID NO 915
<211> LENGTH: 18
<212> TYPE: PRT
<213> ORGANISM: Artificial Sequence
<220> FEATURE:
<223> OTHER INFORMATION: cleavable moiety

<400> SEQUENCE: 915

Ala Val Gly Leu Leu Ala Pro Pro Gly Gly Leu Ser Gly Arg Ser Asp
1               5                   10                  15

Thr His

<210> SEQ ID NO 916
<211> LENGTH: 18
<212> TYPE: PRT
<213> ORGANISM: Artificial Sequence
<220> FEATURE:
<223> OTHER INFORMATION: cleavable moiety

<400> SEQUENCE: 916

Ala Val Gly Leu Leu Ala Pro Pro Gly Gly Leu Ser Gly Arg Ser Asp
1               5                   10                  15

Tyr His

<210> SEQ ID NO 917
<211> LENGTH: 18
<212> TYPE: PRT
<213> ORGANISM: Artificial Sequence
<220> FEATURE:
<223> OTHER INFORMATION: cleavable moiety

<400> SEQUENCE: 917
```

```
Ala Val Gly Leu Leu Ala Pro Pro Gly Gly Leu Ser Gly Arg Ser Asp
1               5                   10                  15

Asn Pro

<210> SEQ ID NO 918
<211> LENGTH: 18
<212> TYPE: PRT
<213> ORGANISM: Artificial Sequence
<220> FEATURE:
<223> OTHER INFORMATION: cleavable moiety

<400> SEQUENCE: 918

Ala Val Gly Leu Leu Ala Pro Pro Gly Gly Leu Ser Gly Arg Ser Ala
1               5                   10                  15

Asn Pro

<210> SEQ ID NO 919
<211> LENGTH: 18
<212> TYPE: PRT
<213> ORGANISM: Artificial Sequence
<220> FEATURE:
<223> OTHER INFORMATION: cleavable moiety

<400> SEQUENCE: 919

Ala Val Gly Leu Leu Ala Pro Pro Gly Gly Leu Ser Gly Arg Ser Ala
1               5                   10                  15

Asn Ile

<210> SEQ ID NO 920
<211> LENGTH: 13
<212> TYPE: PRT
<213> ORGANISM: Artificial Sequence
<220> FEATURE:
<223> OTHER INFORMATION: cleavable moiety

<400> SEQUENCE: 920

Ile Ser Ser Gly Leu Leu Ser Gly Arg Ser Asp Asn Ile
1               5                   10

<210> SEQ ID NO 921
<211> LENGTH: 18
<212> TYPE: PRT
<213> ORGANISM: Artificial Sequence
<220> FEATURE:
<223> OTHER INFORMATION: cleavable moiety

<400> SEQUENCE: 921

Ala Val Gly Leu Leu Ala Pro Pro Gly Gly Leu Ser Gly Arg Ser Asp
1               5                   10                  15

Asn Ile

<210> SEQ ID NO 922

<400> SEQUENCE: 922

000

<210> SEQ ID NO 923
<211> LENGTH: 6
<212> TYPE: PRT
<213> ORGANISM: Artificial Sequence
<220> FEATURE:
<223> OTHER INFORMATION: spacer peptide
```

```
<400> SEQUENCE: 923

Gln Gly Gln Ser Gly Ser
1               5

<210> SEQ ID NO 924
<211> LENGTH: 7
<212> TYPE: PRT
<213> ORGANISM: Artificial Sequence
<220> FEATURE:
<223> OTHER INFORMATION: spacer peptide

<400> SEQUENCE: 924

Gln Gly Gln Ser Gly Gln Gly
1               5

<210> SEQ ID NO 925
<211> LENGTH: 5
<212> TYPE: PRT
<213> ORGANISM: Artificial Sequence
<220> FEATURE:
<223> OTHER INFORMATION: spacer peptide

<400> SEQUENCE: 925

Gln Ser Gly Gln Gly
1               5

<210> SEQ ID NO 926
<211> LENGTH: 4
<212> TYPE: PRT
<213> ORGANISM: Artificial Sequence
<220> FEATURE:
<223> OTHER INFORMATION: spacer peptide

<400> SEQUENCE: 926

Ser Gly Gln Gly
1

<210> SEQ ID NO 927
<211> LENGTH: 3
<212> TYPE: PRT
<213> ORGANISM: Artificial Sequence
<220> FEATURE:
<223> OTHER INFORMATION: spacer peptide

<400> SEQUENCE: 927

Gly Gln Gly
1

<210> SEQ ID NO 928
<211> LENGTH: 2
<212> TYPE: PRT
<213> ORGANISM: Artificial Sequence
<220> FEATURE:
<223> OTHER INFORMATION: spacer peptide

<400> SEQUENCE: 928

Gln Gly
1

<210> SEQ ID NO 929

<400> SEQUENCE: 929

000

<210> SEQ ID NO 930
```

-continued

<400> SEQUENCE: 930

000

<210> SEQ ID NO 931

<400> SEQUENCE: 931

000

<210> SEQ ID NO 932

<400> SEQUENCE: 932

000

<210> SEQ ID NO 933

<400> SEQUENCE: 933

000

<210> SEQ ID NO 934

<400> SEQUENCE: 934

000

<210> SEQ ID NO 935

<400> SEQUENCE: 935

000

<210> SEQ ID NO 936

<400> SEQUENCE: 936

000

<210> SEQ ID NO 937

<400> SEQUENCE: 937

000

<210> SEQ ID NO 938

<400> SEQUENCE: 938

000

<210> SEQ ID NO 939

<400> SEQUENCE: 939

000

<210> SEQ ID NO 940

<400> SEQUENCE: 940

000

<210> SEQ ID NO 941

<400> SEQUENCE: 941

000

<210> SEQ ID NO 942

<400> SEQUENCE: 942

000

<210> SEQ ID NO 943

<400> SEQUENCE: 943

000

<210> SEQ ID NO 944

<400> SEQUENCE: 944

000

<210> SEQ ID NO 945

<400> SEQUENCE: 945

000

<210> SEQ ID NO 946

<400> SEQUENCE: 946

000

<210> SEQ ID NO 947

<400> SEQUENCE: 947

000

<210> SEQ ID NO 948

<400> SEQUENCE: 948

000

<210> SEQ ID NO 949

<400> SEQUENCE: 949

000

<210> SEQ ID NO 950

<400> SEQUENCE: 950

000

<210> SEQ ID NO 951

<400> SEQUENCE: 951

000

<210> SEQ ID NO 952

<400> SEQUENCE: 952

000

<210> SEQ ID NO 953

<400> SEQUENCE: 953

000

<210> SEQ ID NO 954

<400> SEQUENCE: 954

000

<210> SEQ ID NO 955

<400> SEQUENCE: 955

000

<210> SEQ ID NO 956

<400> SEQUENCE: 956

000

<210> SEQ ID NO 957

<400> SEQUENCE: 957

000

<210> SEQ ID NO 958

<400> SEQUENCE: 958

000

<210> SEQ ID NO 959

<400> SEQUENCE: 959

000

<210> SEQ ID NO 960

<400> SEQUENCE: 960

000

<210> SEQ ID NO 961

<400> SEQUENCE: 961

000

<210> SEQ ID NO 962

<400> SEQUENCE: 962

000

<210> SEQ ID NO 963

<400> SEQUENCE: 963

000

<210> SEQ ID NO 964

<400> SEQUENCE: 964

000

<210> SEQ ID NO 965

<400> SEQUENCE: 965

000

<210> SEQ ID NO 966

<400> SEQUENCE: 966

000

<210> SEQ ID NO 967

<400> SEQUENCE: 967

000

<210> SEQ ID NO 968

<400> SEQUENCE: 968

000

<210> SEQ ID NO 969

<400> SEQUENCE: 969

000

<210> SEQ ID NO 970

<400> SEQUENCE: 970

000

<210> SEQ ID NO 971

<400> SEQUENCE: 971

000

<210> SEQ ID NO 972

<400> SEQUENCE: 972

000

<210> SEQ ID NO 973

<400> SEQUENCE: 973

000

<210> SEQ ID NO 974

<400> SEQUENCE: 974

000

<210> SEQ ID NO 975

<400> SEQUENCE: 975

000

<210> SEQ ID NO 976

<400> SEQUENCE: 976

000

<210> SEQ ID NO 977

<400> SEQUENCE: 977

000

<210> SEQ ID NO 978

<400> SEQUENCE: 978

000

<210> SEQ ID NO 979

<400> SEQUENCE: 979

000

<210> SEQ ID NO 980

<400> SEQUENCE: 980

000

<210> SEQ ID NO 981

<400> SEQUENCE: 981

000

<210> SEQ ID NO 982

<400> SEQUENCE: 982

000

<210> SEQ ID NO 983

<400> SEQUENCE: 983

000

<210> SEQ ID NO 984

<400> SEQUENCE: 984

000

<210> SEQ ID NO 985

<400> SEQUENCE: 985

000

<210> SEQ ID NO 986

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

<400> SEQUENCE: 993

000

<210> SEQ ID NO 994

<400> SEQUENCE: 994

000

<210> SEQ ID NO 995

<400> SEQUENCE: 995

000

<210> SEQ ID NO 996

<400> SEQUENCE: 996

000

<210> SEQ ID NO 997

<400> SEQUENCE: 997

000

<210> SEQ ID NO 998
<400> SEQUENCE: 998
000

<210> SEQ ID NO 999
<400> SEQUENCE: 999
000

<210> SEQ ID NO 1000
<400> SEQUENCE: 1000
000

<210> SEQ ID NO 1001
<400> SEQUENCE: 1001
000

<210> SEQ ID NO 1002
<400> SEQUENCE: 1002
000

<210> SEQ ID NO 1003
<400> SEQUENCE: 1003
000

<210> SEQ ID NO 1004
<400> SEQUENCE: 1004
000

<210> SEQ ID NO 1005
<400> SEQUENCE: 1005
000

<210> SEQ ID NO 1006
<400> SEQUENCE: 1006
000

<210> SEQ ID NO 1007
<400> SEQUENCE: 1007
000

<210> SEQ ID NO 1008
<211> LENGTH: 258
<212> TYPE: PRT
<213> ORGANISM: Artificial Sequence
<220> FEATURE:
<223> OTHER INFORMATION: PL07-2001-C5H9v2-WO Light Chain Sequence
      (without linker)

-continued

```
<400> SEQUENCE: 1008

Gly Ile Ala Leu Cys Pro Ser His Phe Cys Gln Leu Pro Gln Thr Gly
1               5                   10                  15

Gly Gly Ser Ser Gly Gly Ser Gly Gly Ser Gly Gly Ile Ser Ser Gly
            20                  25                  30

Leu Leu Ser Gly Arg Ser Asp Asn His Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Ser Ile Ser Ser Tyr Leu Asn Trp Tyr
65                  70                  75                  80

Gln Gln Lys Pro Gly Lys Ala Pro Lys Leu Leu Ile Tyr Ala Ala Ser
                85                  90                  95

Ser Leu Gln Ser Gly Val Pro Ser Arg Phe Ser Gly Ser Gly Ser Gly
            100                 105                 110

Thr Asp Phe Thr Leu Thr Ile Ser Ser Leu Gln Pro Glu Asp Phe Ala
        115                 120                 125

Thr Tyr Tyr Cys Gln Gln Asp Asn Gly Tyr Pro Ser Thr Phe Gly Gly
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 1009
<211> LENGTH: 19
<212> TYPE: PRT
<213> ORGANISM: Artificial Sequence
<220> FEATURE:
<223> OTHER INFORMATION: cleavable moiety

<400> SEQUENCE: 1009

Gly Leu Ser Gly Arg Ser Asp Asn His Gly Gly Ala Val Gly Leu Leu
1               5                   10                  15

Ala Pro Pro

<210> SEQ ID NO 1010
<211> LENGTH: 21
<212> TYPE: PRT
<213> ORGANISM: Artificial Sequence
<220> FEATURE:
<223> OTHER INFORMATION: cleavable moiety

<400> SEQUENCE: 1010

Gly Leu Ser Gly Arg Ser Asp Asn His Gly Gly Val His Met Pro Leu
1               5                   10                  15
```

Gly Phe Leu Gly Pro
            20

<210> SEQ ID NO 1011

<400> SEQUENCE: 1011

000

<210> SEQ ID NO 1012

<400> SEQUENCE: 1012

000

<210> SEQ ID NO 1013

<400> SEQUENCE: 1013

000

<210> SEQ ID NO 1014

<400> SEQUENCE: 1014

000

<210> SEQ ID NO 1015

<400> SEQUENCE: 1015

000

<210> SEQ ID NO 1016

<400> SEQUENCE: 1016

000

<210> SEQ ID NO 1017

<400> SEQUENCE: 1017

000

<210> SEQ ID NO 1018

<400> SEQUENCE: 1018

000

<210> SEQ ID NO 1019

<400> SEQUENCE: 1019

000

<210> SEQ ID NO 1020

<400> SEQUENCE: 1020

000

<210> SEQ ID NO 1021

<400> SEQUENCE: 1021

000

<210> SEQ ID NO 1022

<400> SEQUENCE: 1022

000

<210> SEQ ID NO 1023

<400> SEQUENCE: 1023

000

<210> SEQ ID NO 1024

<400> SEQUENCE: 1024

000

<210> SEQ ID NO 1025

<400> SEQUENCE: 1025

000

<210> SEQ ID NO 1026

<400> SEQUENCE: 1026

000

<210> SEQ ID NO 1027

<400> SEQUENCE: 1027

000

<210> SEQ ID NO 1028

<400> SEQUENCE: 1028

000

<210> SEQ ID NO 1029

<400> SEQUENCE: 1029

000

<210> SEQ ID NO 1030

<400> SEQUENCE: 1030

000

<210> SEQ ID NO 1031

<400> SEQUENCE: 1031

000

<210> SEQ ID NO 1032

<400> SEQUENCE: 1032

000

<210> SEQ ID NO 1033

<400> SEQUENCE: 1033

000

<210> SEQ ID NO 1034

<400> SEQUENCE: 1034

000

<210> SEQ ID NO 1035

<400> SEQUENCE: 1035

000

<210> SEQ ID NO 1036

<400> SEQUENCE: 1036

000

<210> SEQ ID NO 1037

<400> SEQUENCE: 1037

000

<210> SEQ ID NO 1038

<400> SEQUENCE: 1038

000

<210> SEQ ID NO 1039

<400> SEQUENCE: 1039

000

<210> SEQ ID NO 1040

<400> SEQUENCE: 1040

000

<210> SEQ ID NO 1041

<400> SEQUENCE: 1041

000

<210> SEQ ID NO 1042

<400> SEQUENCE: 1042

000

<210> SEQ ID NO 1043

<400> SEQUENCE: 1043

000

<210> SEQ ID NO 1044

<400> SEQUENCE: 1044

000

<210> SEQ ID NO 1045

<400> SEQUENCE: 1045

000

<210> SEQ ID NO 1046

<400> SEQUENCE: 1046

000

<210> SEQ ID NO 1047

<400> SEQUENCE: 1047

000

<210> SEQ ID NO 1048

<400> SEQUENCE: 1048

000

<210> SEQ ID NO 1049

<400> SEQUENCE: 1049

000

<210> SEQ ID NO 1050

<400> SEQUENCE: 1050

000

<210> SEQ ID NO 1051

<400> SEQUENCE: 1051

000

<210> SEQ ID NO 1052

<400> SEQUENCE: 1052

000

<210> SEQ ID NO 1053

<400> SEQUENCE: 1053

000

<210> SEQ ID NO 1054

<400> SEQUENCE: 1054

000

<210> SEQ ID NO 1055

<400> SEQUENCE: 1055

000

<210> SEQ ID NO 1056

<400> SEQUENCE: 1056

000

<210> SEQ ID NO 1057

<400> SEQUENCE: 1057

000

<210> SEQ ID NO 1058

<400> SEQUENCE: 1058

000

<210> SEQ ID NO 1059

<400> SEQUENCE: 1059

000

<210> SEQ ID NO 1060

<400> SEQUENCE: 1060

000

<210> SEQ ID NO 1061

<400> SEQUENCE: 1061

000

<210> SEQ ID NO 1062

<400> SEQUENCE: 1062

000

<210> SEQ ID NO 1063

<400> SEQUENCE: 1063

000

<210> SEQ ID NO 1064

<400> SEQUENCE: 1064

000

<210> SEQ ID NO 1065

<400> SEQUENCE: 1065

000

<210> SEQ ID NO 1066

<400> SEQUENCE: 1066

000

<210> SEQ ID NO 1067

<400> SEQUENCE: 1067

000

<210> SEQ ID NO 1068

<400> SEQUENCE: 1068

000

<210> SEQ ID NO 1069

<400> SEQUENCE: 1069

000

<210> SEQ ID NO 1070

<400> SEQUENCE: 1070

000

<210> SEQ ID NO 1071

<400> SEQUENCE: 1071

000

<210> SEQ ID NO 1072

<400> SEQUENCE: 1072

000

<210> SEQ ID NO 1073

<400> SEQUENCE: 1073

000

<210> SEQ ID NO 1074

<400> SEQUENCE: 1074

000

<210> SEQ ID NO 1075

<400> SEQUENCE: 1075

000

<210> SEQ ID NO 1076

<400> SEQUENCE: 1076

000

<210> SEQ ID NO 1077

<400> SEQUENCE: 1077

000

-continued

<210> SEQ ID NO 1078

<400> SEQUENCE: 1078

000

<210> SEQ ID NO 1079

<400> SEQUENCE: 1079

000

<210> SEQ ID NO 1080

<400> SEQUENCE: 1080

000

<210> SEQ ID NO 1081

<400> SEQUENCE: 1081

000

<210> SEQ ID NO 1082

<400> SEQUENCE: 1082

000

<210> SEQ ID NO 1083

<400> SEQUENCE: 1083

000

<210> SEQ ID NO 1084

<400> SEQUENCE: 1084

000

<210> SEQ ID NO 1085

<400> SEQUENCE: 1085

000

<210> SEQ ID NO 1086

<400> SEQUENCE: 1086

000

<210> SEQ ID NO 1087

<400> SEQUENCE: 1087

000

<210> SEQ ID NO 1088

<400> SEQUENCE: 1088

000

<210> SEQ ID NO 1089

<400> SEQUENCE: 1089

000

<210> SEQ ID NO 1090

<400> SEQUENCE: 1090

000

<210> SEQ ID NO 1091

<400> SEQUENCE: 1091

000

<210> SEQ ID NO 1092

<400> SEQUENCE: 1092

000

<210> SEQ ID NO 1093

<400> SEQUENCE: 1093

000

<210> SEQ ID NO 1094

<400> SEQUENCE: 1094

000

<210> SEQ ID NO 1095

<400> SEQUENCE: 1095

000

<210> SEQ ID NO 1096

<400> SEQUENCE: 1096

000

<210> SEQ ID NO 1097

<400> SEQUENCE: 1097

000

<210> SEQ ID NO 1098

<400> SEQUENCE: 1098

000

<210> SEQ ID NO 1099

<400> SEQUENCE: 1099

000

<210> SEQ ID NO 1100

<400> SEQUENCE: 1100

000

<210> SEQ ID NO 1101
<400> SEQUENCE: 1101
000

<210> SEQ ID NO 1102
<400> SEQUENCE: 1102
000

<210> SEQ ID NO 1103
<400> SEQUENCE: 1103
000

<210> SEQ ID NO 1104
<400> SEQUENCE: 1104
000

<210> SEQ ID NO 1105
<400> SEQUENCE: 1105
000

<210> SEQ ID NO 1106
<400> SEQUENCE: 1106
000

<210> SEQ ID NO 1107
<400> SEQUENCE: 1107
000

<210> SEQ ID NO 1108
<400> SEQUENCE: 1108
000

<210> SEQ ID NO 1109
<400> SEQUENCE: 1109
000

<210> SEQ ID NO 1110
<400> SEQUENCE: 1110
000

<210> SEQ ID NO 1111
<400> SEQUENCE: 1111
000

<210> SEQ ID NO 1112
<400> SEQUENCE: 1112
000

<210> SEQ ID NO 1113
<400> SEQUENCE: 1113
000

<210> SEQ ID NO 1114
<400> SEQUENCE: 1114
000

<210> SEQ ID NO 1115
<400> SEQUENCE: 1115
000

<210> SEQ ID NO 1116
<400> SEQUENCE: 1116
000

<210> SEQ ID NO 1117
<400> SEQUENCE: 1117
000

<210> SEQ ID NO 1118
<400> SEQUENCE: 1118
000

<210> SEQ ID NO 1119
<400> SEQUENCE: 1119
000

<210> SEQ ID NO 1120
<400> SEQUENCE: 1120
000

<210> SEQ ID NO 1121
<400> SEQUENCE: 1121
000

<210> SEQ ID NO 1122
<400> SEQUENCE: 1122
000

<210> SEQ ID NO 1123

```
<400> SEQUENCE: 1123
000

<210> SEQ ID NO 1124
<400> SEQUENCE: 1124
000

<210> SEQ ID NO 1125
<400> SEQUENCE: 1125
000

<210> SEQ ID NO 1126
<400> SEQUENCE: 1126
000

<210> SEQ ID NO 1127
<400> SEQUENCE: 1127
000

<210> SEQ ID NO 1128
<400> SEQUENCE: 1128
000

<210> SEQ ID NO 1129
<400> SEQUENCE: 1129
000

<210> SEQ ID NO 1130
<400> SEQUENCE: 1130
000

<210> SEQ ID NO 1131
<400> SEQUENCE: 1131
000

<210> SEQ ID NO 1132
<400> SEQUENCE: 1132
000

<210> SEQ ID NO 1133
<400> SEQUENCE: 1133
000

<210> SEQ ID NO 1134
<400> SEQUENCE: 1134
```

000

<210> SEQ ID NO 1135

<400> SEQUENCE: 1135

000

<210> SEQ ID NO 1136

<400> SEQUENCE: 1136

000

<210> SEQ ID NO 1137

<400> SEQUENCE: 1137

000

<210> SEQ ID NO 1138

<400> SEQUENCE: 1138

000

<210> SEQ ID NO 1139

<400> SEQUENCE: 1139

000

<210> SEQ ID NO 1140

<400> SEQUENCE: 1140

000

<210> SEQ ID NO 1141

<400> SEQUENCE: 1141

000

<210> SEQ ID NO 1142

<400> SEQUENCE: 1142

000

<210> SEQ ID NO 1143

<400> SEQUENCE: 1143

000

<210> SEQ ID NO 1144

<400> SEQUENCE: 1144

000

<210> SEQ ID NO 1145

<400> SEQUENCE: 1145

000

<210> SEQ ID NO 1146

<400> SEQUENCE: 1146

000

<210> SEQ ID NO 1147

<400> SEQUENCE: 1147

000

<210> SEQ ID NO 1148

<400> SEQUENCE: 1148

000

<210> SEQ ID NO 1149

<400> SEQUENCE: 1149

000

<210> SEQ ID NO 1150

<400> SEQUENCE: 1150

000

<210> SEQ ID NO 1151

<400> SEQUENCE: 1151

000

<210> SEQ ID NO 1152

<400> SEQUENCE: 1152

000

<210> SEQ ID NO 1153

<400> SEQUENCE: 1153

000

<210> SEQ ID NO 1154

<400> SEQUENCE: 1154

000

<210> SEQ ID NO 1155

<400> SEQUENCE: 1155

000

<210> SEQ ID NO 1156

<400> SEQUENCE: 1156

000

<210> SEQ ID NO 1157

<400> SEQUENCE: 1157

000

<210> SEQ ID NO 1158

<400> SEQUENCE: 1158

000

<210> SEQ ID NO 1159

<400> SEQUENCE: 1159

000

<210> SEQ ID NO 1160

<400> SEQUENCE: 1160

000

<210> SEQ ID NO 1161

<400> SEQUENCE: 1161

000

<210> SEQ ID NO 1162

<400> SEQUENCE: 1162

000

<210> SEQ ID NO 1163

<400> SEQUENCE: 1163

000

<210> SEQ ID NO 1164

<400> SEQUENCE: 1164

000

<210> SEQ ID NO 1165

<400> SEQUENCE: 1165

000

<210> SEQ ID NO 1166

<400> SEQUENCE: 1166

000

<210> SEQ ID NO 1167

<400> SEQUENCE: 1167

000

<210> SEQ ID NO 1168

<400> SEQUENCE: 1168

000

<210> SEQ ID NO 1169

<400> SEQUENCE: 1169

000

<210> SEQ ID NO 1170

<400> SEQUENCE: 1170

000

<210> SEQ ID NO 1171

<400> SEQUENCE: 1171

000

<210> SEQ ID NO 1172

<400> SEQUENCE: 1172

000

<210> SEQ ID NO 1173

<400> SEQUENCE: 1173

000

<210> SEQ ID NO 1174

<400> SEQUENCE: 1174

000

<210> SEQ ID NO 1175

<400> SEQUENCE: 1175

000

<210> SEQ ID NO 1176

<400> SEQUENCE: 1176

000

<210> SEQ ID NO 1177

<400> SEQUENCE: 1177

000

<210> SEQ ID NO 1178

<400> SEQUENCE: 1178

000

<210> SEQ ID NO 1179

<400> SEQUENCE: 1179

000

<210> SEQ ID NO 1180

<400> SEQUENCE: 1180

000

<210> SEQ ID NO 1181

<400> SEQUENCE: 1181

000

<210> SEQ ID NO 1182

<400> SEQUENCE: 1182

000

<210> SEQ ID NO 1183

<400> SEQUENCE: 1183

000

<210> SEQ ID NO 1184

<400> SEQUENCE: 1184

000

<210> SEQ ID NO 1185

<400> SEQUENCE: 1185

000

<210> SEQ ID NO 1186

<400> SEQUENCE: 1186

000

<210> SEQ ID NO 1187

<400> SEQUENCE: 1187

000

<210> SEQ ID NO 1188

<400> SEQUENCE: 1188

000

<210> SEQ ID NO 1189

<400> SEQUENCE: 1189

000

<210> SEQ ID NO 1190

<400> SEQUENCE: 1190

000

<210> SEQ ID NO 1191

<400> SEQUENCE: 1191

000

<210> SEQ ID NO 1192
<211> LENGTH: 5
<212> TYPE: PRT
<213> ORGANISM: Artificial Sequence
<220> FEATURE:
<223> OTHER INFORMATION: spacer peptide

<400> SEQUENCE: 1192

Gly Gln Ser Gly Ser
1               5

<210> SEQ ID NO 1193
<211> LENGTH: 4
<212> TYPE: PRT
<213> ORGANISM: Artificial Sequence
<220> FEATURE:
<223> OTHER INFORMATION: spacer peptide

<400> SEQUENCE: 1193

Gln Ser Gly Ser
1

<210> SEQ ID NO 1194
<211> LENGTH: 3
<212> TYPE: PRT
<213> ORGANISM: Artificial Sequence
<220> FEATURE:
<223> OTHER INFORMATION: spacer peptide

<400> SEQUENCE: 1194

Ser Gly Ser
1

<210> SEQ ID NO 1195
<211> LENGTH: 2
<212> TYPE: PRT
<213> ORGANISM: Artificial Sequence
<220> FEATURE:
<223> OTHER INFORMATION: spacer peptide

<400> SEQUENCE: 1195

Gly Ser
1

<210> SEQ ID NO 1196
<211> LENGTH: 6
<212> TYPE: PRT
<213> ORGANISM: Artificial Sequence
<220> FEATURE:
<223> OTHER INFORMATION: spacer peptide

<400> SEQUENCE: 1196

Gln Gly Gln Ser Gly Gln
1               5

<210> SEQ ID NO 1197
<211> LENGTH: 5
<212> TYPE: PRT
<213> ORGANISM: Artificial Sequence
<220> FEATURE:
<223> OTHER INFORMATION: spacer peptide

```
<400> SEQUENCE: 1197

Gly Gln Ser Gly Gln
1               5

<210> SEQ ID NO 1198
<211> LENGTH: 4
<212> TYPE: PRT
<213> ORGANISM: Artificial Sequence
<220> FEATURE:
<223> OTHER INFORMATION: spacer peptide

<400> SEQUENCE: 1198

Gln Ser Gly Gln
1

<210> SEQ ID NO 1199
<211> LENGTH: 2
<212> TYPE: PRT
<213> ORGANISM: Artificial Sequence
<220> FEATURE:
<223> OTHER INFORMATION: spacer peptide

<400> SEQUENCE: 1199

Gly Gln
1

<210> SEQ ID NO 1200

<400> SEQUENCE: 1200

000

<210> SEQ ID NO 1201

<400> SEQUENCE: 1201

000

<210> SEQ ID NO 1202

<400> SEQUENCE: 1202

000

<210> SEQ ID NO 1203
<211> LENGTH: 15
<212> TYPE: PRT
<213> ORGANISM: Artificial Sequence
<220> FEATURE:
<223> OTHER INFORMATION: anti-PDL1 activatable antibody PL07-2001-C5H9v2
      VL CDR3 peptide antigen

<400> SEQUENCE: 1203

Cys Gln Gln Asp Asn Gly Tyr Pro Ser Thr Phe Gly Gly Gly Thr
1               5                   10                  15
```

ACTIVATABLE ANTI-PDL1 ANTIBODIES, AND METHODS OF USE THEREOF

RELATED APPLICATIONS

This application claims the benefit of U.S. Provisional Application No. 62/513,937, filed Jun. 1, 2017, U.S. Provisional Application No. 62/534,950, filed Jul. 20, 2017, U.S. Provisional Application No. 62/555,598, filed Sep. 7, 2017, and U.S. Provisional Application No. 62/657,567, filed Apr. 13, 2018, the contents of each of which are incorporated herein by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: CYTM_052_001US_SeqList_ST25, date recorded: Jul. 24, 2018, file size 80 kilobytes).

FIELD OF THE INVENTION

This invention generally relates to specific dosing regimens for administering anti-PDL1 activatable antibodies for the treatment of cancer.

BACKGROUND OF THE INVENTION

Antibody-based therapies have proven effective treatments for several diseases but in some cases, toxicities due to broad target expression have limited their therapeutic effectiveness. In addition, antibody-based therapeutics have exhibited other limitations such as rapid clearance from the circulation following administration.

In the realm of small molecule therapeutics, strategies have been developed to provide prodrugs of an active chemical entity. Such prodrugs are administered in a relatively inactive (or significantly less active) form. Once administered, the prodrug is metabolized in vivo into the active compound. Such prodrug strategies can provide for increased selectivity of the drug for its intended target and for a reduction of adverse effects.

Accordingly, there is a continued need in the field of antibody-based therapeutics for antibodies that mimic the desirable characteristics of the small molecule prodrug.

SUMMARY OF THE INVENTION

In various aspect the invention provides methods of treating, alleviating a symptom of, or delaying the progression of a cancer in a subject, by administering intravenously at a dose of about between 0.3 mg/kg to 30 mg/kg of an activatable anti-PDL1 antibody to the subject. The activatable antibody has an antibody (AB) that specifically binds to human PDL1, The AB has a heavy chain variable region having a complementarity determining region 1 (CDRH1) having the amino acid sequence of SEQ ID NO:212, a complementarity determining region 2 (CDRH2) having the amino acid sequence of SEQ ID NO:246, and a complementarity determining region 3 (CDRH3) having the amino acid sequence or SEQ ID NO:235; and a light chain variable region having a light chain complementarity determining region 1 (CDRL1) having the amino acid sequence of SEQ ID NO:209, a light chain complementarity determining region 2, (CDRL2) having the amino acid sequence of SEQ ID NO:215, a light chain complementarity determining region 3 (CDRL3) having the amino acid sequence of SEQ ID NO:228; a cleavable moiety (CM) linked to the AB, wherein the CM is a polypeptide that functions as a substrate for a protease; and a masking moiety (MM) linked to the CM.

Also included in the invention are methods of treating, alleviating a symptom of, or delaying the progression of a cancer in a subject, by administering intravenously at a fixed dose of about between 24 and 2400 mg of an activatable anti-PDL1 antibody to the subject, wherein the activatable antibody has an antibody (AB) that specifically binds to human PDL1, wherein the AB comprises a heavy chain variable region having a complementarity determining region 1 (CDRH1) having the amino acid sequence of SEQ ID NO:212, a complementarity determining region 2 (CDRH2) having the amino acid sequence of SEQ ID NO:246, and a complementarity determining region 3 (CDRH3) having the amino acid sequence or SEQ ID NO:235; and a light chain variable region having a light chain complementarity determining region 1 (CDRL1) having the amino acid sequence of SEQ ID NO:209, a light chain complementarity determining region 2, (CDRL2) having the amino acid sequence of SEQ ID NO:215, a light chain complementarity determining region 3 (CDRL3) having the amino acid sequence of SEQ ID NO:228; a cleavable moiety (CM) linked to the AB, wherein the CM is a polypeptide that functions as a substrate for a protease; and a masking moiety (MM) linked to the AB.

In another aspect the invention provides an activatable anti-PDL1 antibody having an antibody (AB) that specifically binds to human PDL1. The AB has a heavy chain variable region having a complementarity determining region 1 (CDRH1) having the amino acid sequence of SEQ ID NO:212, a complementarity determining region 2 (CDRH2) having the amino acid sequence of SEQ ID NO:246, and a complementarity determining region 3 (CDRH3) having the amino acid sequence or SEQ ID NO:235; and a light chain variable region having a light chain complementarity determining region 1 (CDRL1) having the amino acid sequence of SEQ ID NO:209, a light chain complementarity determining region 2, (CDRL2) having the amino acid sequence of SEQ ID NO:215, a light chain complementarity determining region 3 (CDRL3) having the amino acid sequence of SEQ ID NO:228; a cleavable moiety (CM) linked to the AB, wherein the CM is a polypeptide that functions as a substrate for a protease; and a masking moiety (MM) linked to the CM, for use in treating, alleviating a symptom of, or delaying the progression of a cancer in a subject, and wherein the activatable antibody is administered intravenously at a dose of about between 0.3 mg/kg to 30 mg/kg In a further aspect the invention provides an activatable anti-PDL1 antibody having an antibody (AB) that specifically binds to human PDL1. The AB has a heavy chain variable region having a complementarity determining region 1 (CDRH1) having the amino acid sequence of SEQ ID NO:212, a complementarity determining region 2 (CDRH2) having the amino acid sequence of SEQ ID NO:246, and a complementarity determining region 3 (CDRH3) having the amino acid sequence or SEQ ID NO:235; and a light chain variable region having a light chain complementarity determining region 1 (CDRL1) having the amino acid sequence of SEQ ID NO:209, a light chain complementarity determining region 2, (CDRL2) having the amino acid sequence of SEQ ID NO:215, a light chain complementarity determining region 3 (CDRL3) having the amino acid sequence of SEQ ID NO:228, a cleavable moiety (CM) linked to the AB, wherein the CM is a polypeptide that functions as a substrate for a protease; and a masking moiety (MM) linked to the CM, for use in treating, alleviating a symptom of, or delaying the progression of a cancer in a subject, and wherein the activatable antibody is administered intravenously at a fixed dose of about between 24 and 2400 mg.

The MM inhibits the binding of the AB to human PDL1 when the activatable antibody is in an uncleaved state. In some aspects the MM had the amino acid sequence of SEQ ID NO: 63.

In some aspects the CM has the amino acid sequence of SEQ ID NO: 377.

The AB has a heavy chain variable region (VH) having the amino acid sequence of SEQ ID NO: 46 and a light chain variable (VL) having the amino acid sequence of SEQ ID NO: 58 or SEQ ID NO: 137.

In further aspects the activatable antibody has a light chain having the amino acid sequence of SEQ ID NO: 1008 and a heavy chain having the amino acid sequence of SEQ ID NO: 432.

Alternatively, the activatable antibody having a light chain having the amino acid sequence of SEQ ID NO: 428 and a heavy chain having the amino acid sequence of SEQ ID NO: 432.

The dose is about between 3 mg/kg to 10 mg/kg. The dose is about between 3 mg/kg to 15 mg/kg. The dose is 0.3 mg/kg, 1 mg/kg, 3 mg/kg, 6 mg/kg, 10 mg/kg, 15 mg/kg, or 30 mg/kg.

The fixed dose is 240 mg, 480 mg, 800 mg, 1200 mg, 2400 mg.

The activatable antibody is administered on a schedule of one dose every 7-28 days, For example activatable antibody is administered on a schedule the one dose every 14 days or 21 days.

The activatable antibody is administrated as a monotherapy. Alternatively, activatable antibody is administrated as a component of a combination therapy. The combination therapy includes administering a dose of an anti-CTLA-4 antibody or a B-RAF inhibitor The anti-CTLA-4 antibody is for example, ipilimumab. The anti-CTLA-4 antibody is administered intravenously. The anti-CTLA-4 antibody is administered at a dose of 3 mg/kg, 6 mg/kg or 10 mg/kg. Alternatively, the anti-CTLA-4 antibody is administered at a fixed dose 240 mg, 480 mg or 800 mg.

The B-RAF inhibitor is vemurafenib. The B-RAF inhibitor is administered orally. The B-RAF inhibitor is administered at a dose of 960 mg or at a dose of 875 mg. The activatable antibody and the B-RAF inhibitor are administered over a same period of time.

In some aspects the dose of the B-RAF inhibitor is administered twice daily. In other aspects at least 4 doses each of the activatable antibody and the B-RAF inhibitor are administered.

In some aspects multiple doses of the activatable antibody and the anti-CTLA-4 antibody are administered over a first period of time, followed by administration of multiple doses of the activatable antibody as a monotherapy over a second period of time.

In further aspects, the activatable antibody and a dose of the anti-CTLA-4 antibody are administered concomitantly as a combination therapy every 21 days for 4 doses, followed by administration of a dose of the activatable antibody as a monotherapy every 14 days.

In yet another aspect multiple doses of the activatable antibody as a monotherapy are administered over a first period of time, followed by concomitant administration of multiple doses of the activatable antibody and the anti-CTLA-4 antibody as a combination therapy are administered over a second period of time.

In a yet a further aspect multiple doses of the activatable antibody are administered as a monotherapy over a first period of time, multiple doses of the activatable antibody and the anti-CTLA-4 antibody are subsequently administered as a combination therapy over a second period of time, and multiple doses of the activatable antibody as a monotherapy are administered over a third period of time.

In other aspects, the activatable antibody is administered as a monotherapy every 14 days for 4 doses, followed by administration of a dose of activatable antibody and a dose of anti-CTLA-4 antibody as a combination therapy every 21 days, for 4 doses, followed by administration of a dose an activatable antibody as a monotherapy every 14 days.

The cancer is an advanced, unresectable solid tumor or lymphoma. For example, the advanced unresectable tumor is a PDL1-responsive tumor type.

The cancer is a carcinoma such as carcinoma squamous cell carcinoma.

The cancer is for example, an anal squamous cell carcinoma, basal cell carcinoma, bladder cancer, bone cancer, bowel carcinoma, breast cancer, carcinoid, castration-resistant prostate cancer (CRPC), cervical carcinoma, colorectal cancer (CRC), colon cancer cutaneous squamous cell carcinoma, endometrial cancer, esophageal cancer, gastric carcinoma, gastroesophageal junction cancer, glioblastoma/mixed glioma, glioma, head and neck cancer, hepatocellular carcinoma, hematologic malignancy. liver cancer, lung cancer, melanoma, Merkel cell carcinoma, multiple myeloma, nasopharyngeal cancer, osteosarcoma, ovarian cancer, pancreatic cancer, peritoneal carcinoma, undifferentiated pleomorphic sarcoma, prostate cancer, rectal carcinoma, renal cancer, sarcoma, salivary gland carcinoma, squamous cell carcinoma, stomach cancer, testicular cancer, thymic carcinoma, thymic epithelial tumor, thymoma, thyroid cancer, urogenital cancer, urothelial cancer, uterine carcinoma, or uterine sarcoma.

The cancer is a High Tumor Mutational Burden (hTMB) cancer.

The breast cancer is triple negative breast cancer or estrogen receptor positive breast cancer.

The hematologic malignancy is a lymphoma or a leukemia. The lymphoma is for example, a B-cell lymphoma, a T-cell lymphoma, Hodgkin's lymphoma, or an EBV lymphoma, primary mediastinal B-cell lymphoma.

The cancer is melanoma.

The bowel carcinoma is for example small bowel carcinoma or small bowel adenocarcinoma. The colon cancer is colon adenocarcinoma, The lung cancer is for example non-small cell lung cancer (NSCLC) or small cell lung cancer. The NSCLC is non-squamous NSCLC or squamous NSCLC.

The prostate cancer is small cell neuroendocrine prostate cancer.

The renal cancer is renal cell carcinoma or renal sarcoma.

Preferably, the cancer is undifferentiated pleomorphic sarcoma, small bowel adenocarcinoma, Merkel cell carcinoma, thymic carcinoma, anal squamous cell carcinoma, cutaneous squamous cell carcinoma or triple negative breast cancer.

The subject exhibits one or more of the following characteristics PD-1/PDL1 inhibitor-naïve, CTLA-4 inhibitor-naïve, BRAF$^{V600E}$ mutation positive, BRAF inhibitor-naïve, PDL1 positive, PDL1 unknown, been previously treated with a PD1/PDL1 inhibitor has no further standard of care available the PD1/PDL1 inhibitor therapy is not approved for the subject's cancer, t has been previously treated with a PD-1/PDL1 inhibitor, wherein treatment with the PD-1/PDL1 inhibitor was discontinued for reasons other than toxicity, and wherein the subject is CTLA-4 inhibitor-naïve, is immunotherapy naïve.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE DRAWINGS

FIG. 3A is an electropherogram showing 17G1 detection of decreasing concentration of one arm activated PL07-2001-C5H9v2 (1, 0.33, and 0.11 ug/ml, referred to in the FIG. as AA MIX). FIG. 3B demonstrates relative activation percent for the top 6 clones of one arm activated activatable antibody. The relative activation rate is preserved at different concentrations. 21H10 and 27C1 clones have lower affinity resulting in no data for the 0.11 ug/ml concentration.

FIG. 5A demonstrates detection of the anti-PDL1 activatable antibody referred to herein as PL07-2001-05H9v2 in plasma of mice treated with 10 mg/kg of PL07-2001-C5H9v2 using A110UK (Goat Anti-Human IgG (H&L) adsorbed against monkey unlabeled) from American Qualex (available on the web at aqsp.com/). FIG. 5B demonstrates detection of PL07-2001-C5H9v2 in plasma of mice treated with 0.1 mg/kg of PL07-2001-C5H9v2 using an anti-idiotypic 17G1 antibody.

FIG. 6A and FIG. 6B are a series of graphs depicting preferential activation of activatable antibody (AA) therapeutics in tumor versus plasma detected in xenograft tumor model. MDA-MB-231 xenograft mice were treated with 1 mg/ml of the anti-PDL1 activatable antibody referred to herein as PL07-2001-C5H9v2. Tumor and plasma samples were collected on day 4. FIGS. 6A and 6B demonstrate the analysis of tumor homogenate and plasma samples by a Wes (ProteinSimple) based capillary electrophoresis immunoassay method of the disclosure.

FIGS. 7A and 7B demonstrate the analysis of tumor homogenate and plasma samples by a Wes (ProteinSimple) based capillary electrophoresis immunoassay method of the disclosure.

DETAILED DESCRIPTION OF THE INVENTION

Figure 1A:
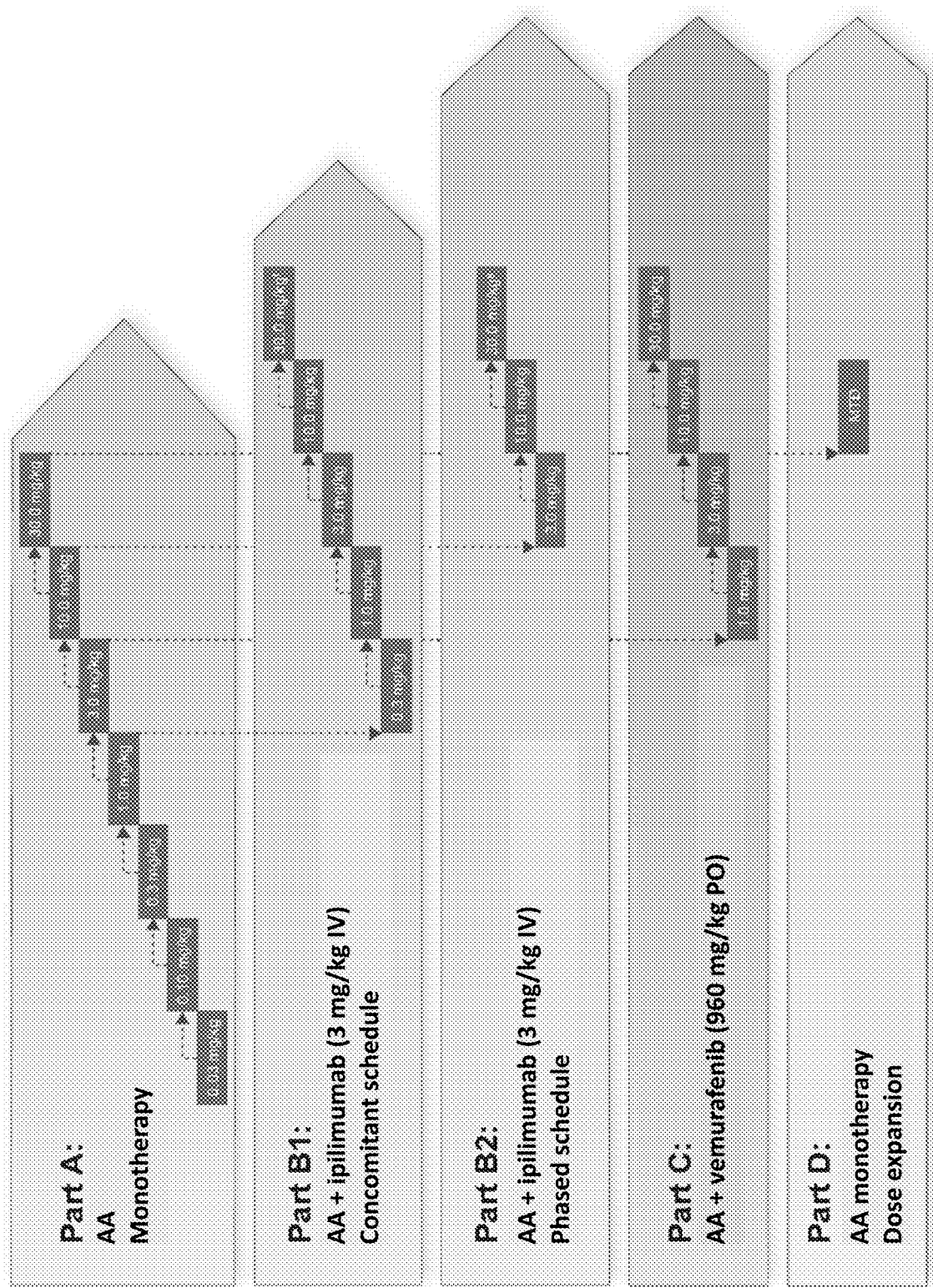
FIG. 1A is a schematic representation of the study design for a study in Example 2, where "AA" represents the anti-PDL1 activatable antibody referred to herein as PL07-2001-C5H9v2, which comprises the heavy chain sequence of SEQ ID NO: 432 and the light chain sequence of SEQ ID NO: 428.

The present disclosure provides methods of treating cancer by administering an activatable anti-PDL1 antibody. Specifically, the invention is based upon the results of the first ever human safety and efficacy study of an activatable antibody. A dose escalation study was performed to evaluate the safety and efficacy of PL07-2001-C5H9v2 as a monotherapy or in combination with ipilimumab PL07-2001-C5H9v2 is protease activated anti-PDL1 antibody. PL07-2001-C5H9v2 is activated by tumor associated proteases and has been shown to be inactive in circulation.

Patients, with metastatic, or advanced unresectable solid tumors or lymphoma were intravenously administered 0.03 mg/kg-30 mg/kg PL07-2001-C5H9v2 every three weeks. Among patients with evaluable data (n=19), target lesions decreased from baseline in 8 patients (42%) Target lesions decreased from baseline at dose levels ≥3 mg/kg in 6/10 patients (60%).

The disease control rates was 45% for patients in all patients dosed between 0.03 to 30 mg/kg PL07-2001-C5H9v2. For patients dosed with at least 10 mg/kg, disease control rates were over 66%. Surprisingly, pharmacokinetic (PK) analysis demonstrated that the PL07-2001-C5H9v2 circulates in plasma primarily in the unactivated form and the PK is only minimally reduced by targeted mediated drug disposition.

The activatable anti-PDL1 antibodies described herein overcome a limitation of antibody therapeutics, particularly antibody therapeutics that are known to be toxic to at least some degree in vivo. Target-mediated toxicity constitutes a major limitation for the development of therapeutic antibodies. The activatable anti-PDL1 antibodies provided herein are designed to address the toxicity associated with the inhibition of the target in normal tissues by traditional therapeutic antibodies. Importantly, these activatable anti-PDL1 antibodies remain masked until proteolytically activated at the site of disease.

Activatable Anti-PDL1 Antibodies

The activatable antibodies used in the compositions and methods of the disclosure were generated and characterized using the methods disclosed in PCT Publication No. WO 2016/149201, the contents of which are incorporated by reference herein in their entirety.

The activatable anti-PDL1 antibodies include an antibody that specifically binds PDL1 coupled to a masking moiety (MM), such that coupling of the MM reduces the ability of the antibody or antigen-binding fragment thereof to bind PDL1. The MM is coupled via a sequence that includes a substrate for a protease, for example, a protease that is co-localized with PDL1 at a treatment site in a subject.

In some embodiments, the activatable antibodies include an antibody (AB) that is modified by an MM and also includes one or more cleavable moieties (CM). Such activatable antibodies exhibit activatable/switchable binding, to the AB's target. Activatable antibodies generally include an antibody or antibody fragment (AB), modified by or coupled to a masking moiety (MM) and a modifiable or cleavable moiety (CM). In some embodiments, the CM contains an amino acid sequence that serves as a substrate for at least one protease. In preferred embodiments the AB has two heavy chains and two light chains.

The elements of the activatable antibodies are arranged so that the MM and CM are positioned such that in a cleaved (or relatively active) state and in the presence of a target, the AB binds a target while the activatable antibody is in an uncleaved (or relatively inactive) state in the presence of the target, specific binding of the AB to its target is reduced or inhibited. The specific binding of the AB to its target can be reduced due to the inhibition or masking of the AB's ability to specifically bind its target by the MM.

Activatable antibodies can be provided in a variety of structural configurations. Exemplary formulae for activatable antibodies are provided below. It is specifically contemplated that the N- to C-terminal order of the AB, MM and CM may be reversed within an activatable antibody. It should be noted that although MM and CM are indicated as distinct components in the formulae below, in all exemplary embodiments (including formulae) disclosed herein it is contemplated that the amino acid sequences of the MM and the CM could overlap, e.g., such that the CM is completely or partially contained within the MM.

For example, activatable antibodies can be represented by the following formula (in order from an amino (N) terminal region to carboxyl (C) terminal region:

(MM)-(CM)-(AB)

(AB)-(CM)-(MM)

where MM is a masking moiety, CM is a cleavable moiety, and AB is an antibody. In addition, the formulae above provide for additional amino acid sequences that may be positioned N-terminal or C-terminal to the activatable antibodies elements.

In many embodiments it may be desirable to insert one or more linkers, e.g., flexible linkers, into the activatable antibody construct so as to provide for flexibility at one or more of the MM-CM junction, the CM-AB junction, or both. For example, the AB, MM, and/or CM may not contain a sufficient number of residues (e.g., Gly, Ser, Asp, Asn, especially Gly and Ser, particularly Gly) to provide the desired flexibility. As such, the switchable phenotype of such activatable antibody constructs may benefit from introduction of one or more amino acids to provide for a flexible linker. In addition, as described below, where the activatable antibody is provided as a conformationally constrained construct, a flexible linker can be operably inserted to facilitate formation and maintenance of a cyclic structure in the uncleaved activatable antibody.

For example, in certain embodiments an activatable antibody comprises one of the following formulae (where the formula below represent an amino acid sequence in either N- to C-terminal direction or C- to N-terminal direction):

(MM)-L1-(CM)-(AB)

(MM)-(CM)-L2-(AB)

(MM)-L1-(CM)-L2-(AB)

wherein MM, CM, and AB are as defined above; wherein L1 and L2 are each independently and optionally present or absent, are the same or different flexible linkers that include at least 1 flexible amino acid (e.g., Gly). In addition, the formulae above provide for additional amino acid sequences that may be positioned N-terminal or C-terminal to the activatable antibodies elements. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HAS)).

When the AB is modified with a MM and is in the presence of the target specific binding of the AB to its target is reduced or inhibited, as compared to the specific binding of the AB not modified with an MM or the specific binding of the parental AB to the target. When compared to the binding of the AB not modified with an MM or the binding of the parental AB to the target the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

Conversely, the binding affinity of the AB modified with a MM and a CM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM and a CM or of the parental AB towards the target.

As used herein, the term cleaved state refers to the condition of the activatable antibodies following modification of the CM by at least one protease. The term uncleaved state, as used herein, refers to the condition of the activatable antibodies in the absence of cleavage of the CM by a protease. As discussed above, the term "activatable antibodies" is used herein to refer to an activatable antibody in both its uncleaved (native) state, as well as in its cleaved state. It will be apparent to the ordinarily skilled artisan that in some embodiments a cleaved activatable antibody may lack an MM due to cleavage of the CM by protease, resulting in release of at least the MM.

By activatable or switchable is meant that the activatable antibody exhibits a first level of binding to a target when the activatable antibody is in a inhibited, masked or uncleaved state (i.e., a first conformation), and a second level of binding to the target in the uninhibited, unmasked and/or cleaved state (i.e., a second conformation), where the second level of target binding is greater than the first level of binding. In general, the access of target to the AB of the activatable antibody is greater in the presence of a cleaving agent capable of cleaving the CM, i.e., a protease, than in the absence of such a cleaving agent. Thus, when the activatable antibody is in the uncleaved state, the AB is inhibited from target binding and can be masked from target binding (i.e., the first conformation is such the AB cannot bind the target), and in the cleaved state the AB is not inhibited or is unmasked to target binding.

The CM and AB of the activatable antibodies are selected so that the AB represents a binding moiety for a given target, and the CM represents a substrate for a protease. In some embodiments, the protease is co-localized with the target at a treatment site in a subject. As used herein, co-localized refers to being at the same site or relatively close nearby. In some embodiments, a protease cleaves a CM yielding an activated antibody that binds to a target located nearby the cleavage site. The activatable antibodies disclosed herein find particular use where, for example, a protease capable of cleaving a site in the CM, i.e., a protease, is present at relatively higher levels in or in close proximity to target-containing tissue of a treatment site or diagnostic site than in tissue of non-treatment sites (for example in healthy tissue). In some embodiments, a CM of the disclosure is also cleaved by one or more other proteases. In some embodiments, it is the one or more other proteases that is co-localized with the target and that is responsible for cleavage of the CM in vivo.

In some embodiments activatable antibodies provide for reduced toxicity and/or adverse side effects that could otherwise result from binding of the AB at non-treatment sites if the AB were not masked or otherwise inhibited from binding to the target.

In general, an activatable antibody can be designed by selecting an AB of interest and constructing the remainder of the activatable antibody so that, when conformationally constrained, the MM provides for masking of the AB or reduction of binding of the AB to its target. Structural design criteria can be to be taken into account to provide for this functional feature.

For specific cleavage by an enzyme, contact between the enzyme and CM is made. When the activatable antibody comprising an AB coupled to a MM and a CM is in the presence of target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but unable to cleave because of other cellular factors or protein modification of the enzyme.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism.

An exemplary activatable antibody includes an antibody (AB) that specifically binds to human PDL1, having a heavy chain variable region having a complementarity determining region 1 (CDRH1) comprising the amino acid sequence of SEQ ID NO:212, a complementarity determining region 2 (CDRH2) having the amino acid sequence of SEQ ID NO:246, and a complementarity determining region 3 (CDRH3) having the amino acid sequence or SEQ ID NO:235; and a light chain variable region having a light chain complementarity determining region 1 (CDRL1) having the amino acid sequence of SEQ ID NO:209, a light chain complementarity determining region 2, (CDRL2) having the amino acid sequence of SEQ ID NO:215, a light chain complementarity determining region 3 (CDRL3) having the amino acid sequence of SEQ ID NO:228; a cleavable moiety (CM) linked to the AB, wherein the CM is a polypeptide that functions as a substrate for a protease; and a masking moiety (MM) linked to the CM. The CM is for example, ISSGLLSGRSDNH, (SEQ ID NO: 377). The MM is for example, GIALCPSHFCQLPQT (SEQ ID NO: 63).

An exemplary activatable anti PDLantibody includes an antibody (AB) that specifically binds to human PDL1. The AB includes two antibody heavy chains each having a heavy chain variable region having a complementarity determining region 1 (CDRH1) having the amino acid sequence of SEQ ID NO:212, a complementarity determining region 2 (CDRH2) having the amino acid sequence of SEQ ID NO:246, and a complementarity determining region 3 (CDRH3) having the amino acid sequence of or SEQ ID NO:235; and two antibody light chains each having a light chain variable region having a light chain complementarity determining region 1 (CDR1L) having the amino acid sequence of SEQ ID NO:209, a light chain complementarity determining region 2 (CDRL2) having the amino acid sequence of SEQ ID NO:215, a light chain complementarity determining region 3 (CDRL3) having the amino acid sequence of SEQ ID NO:228; two masking moiety peptides (MM1s); and two cleavable moiety peptides (CM1s), each CM1 being a substrate for a protease. Each MM1 is linked in an N- to C-terminal direction to a CM1, to form two MM1-CM1 peptides where the carboxyl terminus of each MM1-CM1 peptide is linked to the amino terminus of each AB light chain. The CM is for example, ISSGLLSGRSDNH (SEQ ID NO: 377). The MM is for example, GIALCP-SHFCQLPQT (SEQ ID NO: 63).

In some embodiments the activatable anti-PDL1 antibody has a heavy chain variable regon of SEQ ID NO: 46 and a light chain variable region of SEQ ID NO: 137 (which includes a CM of SEQ ID NO: 377, an a MM of SEQ ID NO: 63, and a VL of SEQ ID NO:58).

In other embodiments the activatable anti-PDL1 antibody has a heavy chain of SEQ ID NO: 432 and a light chain of SEQ ID NO: 428, (which includes a CM of SEQ ID NO: 377, an a MM of SEQ ID NO: 63, a VL of SEQ ID NO:58, and a Kappa constant domain).

A preferred activatable anti-PDL1 antibody's useful in the methods of the invention include PL07-2001-C5H9v2 which includes a heavy chain variable regon of SEQ ID NO: 46 and a light chain variable region of SEQ ID NO: 137. Full length heavy and light chain of PL07-2001-C5H9v2 includes SEQ ID NO; 432 and SEQ ID NO: 428, respectively.

An additional activatable anti-PDL1 antibody useful in the methods of the invention include PL07-2001-C5H9v2-WO which includes a heavy chain variable region regon of SEQ ID NO: 46 and a light chain variable region of SEQ ID NO: 58 Full length heavy and light chain of PL07-2001-C5H9v2-WO includes SEQ ID NO: 432 and SEQ ID NO: 1008, respectively.

PL07-2001-C5H9v2 Heavy Chain Variable Sequence
(SEQ ID NO: 46)
EVQLLESGGGLVQPGGSLRLSCAASGFTFSSYAMSWVRQAPGKGLEWVSS

IWRNGIVTVYADSVKGRFTISRDNSKNTLYLQMNSLRAEDTAVYYCAKWS

AAFDYWGQGTLVTVSS

PL07-2001-C5H9v2 Light Chain Variable Sequence
(SEQ ID NO: 137)
QGQSGSGIALCPSHFCQLPQTGGGSSGGSGGSGGISSGLLSGRSDNHGGS

DIQMTQSPSSLSASVGDRVTITCRASQSISSYLNWYQQKPGKAPKLLIYA

ASSLQSGVPSRFSGSGSGTDFTLTISSLQPEDFATYYCQQDNGYPSTFGG

GTKVEIKR

PL07-2001-C5H9v2-WO Light Chain Variable Sequence
(SEQ ID NO: 138)
GIALCPSHFCQLPQTGGGSSGGSGGSGGISSGLLSGRSDNHGGSDIQMTQ

SPSSLSASVGDRVTITCRASQSISSYLNWYQQKPGKAPKLLIYAASSLQS

GVPSRFSGSGSGTDFTLTISSLQPEDFATYYCQQDNGYPSTFGGGTKVEI

KR

PL07-2001-C5H9v2 Heavy Chain Sequence
(SEQ ID NO: 432)
EVQLLESGGGLVQPGGSLRLSCAASGFTFSSYAMSWVRQAPGKGLEWVSS

IWRNGIVTVYADSVKGRFTISRDNSKNTLYLQMNSLRAEDTAVYYCAKWS

AAFDYWGQGTLVTVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLG

PL07-2001-C5H9v2 Light Chain Sequence
(SEQ ID NO: 428)
QGQSGSGIALCPSHFCQLPQTGGGSSGGSGGSGGISSGLLSGRSDNHGGS

DIQMTQSPSSLSASVGDRVTITCRASQSISSYLNWYQQKPGKAPKLLIYA

ASSLQSGVPSRFSGSGSGTDFTLTISSLQPEDFATYYCQQDNGYPSTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

PL07-2001-C5H9v2-WO Light Chain Sequence (without linker)
(SEQ ID NO: 1008)
GIALCPSHFCQLPQTGGGSSGGSGGSGGISSGLLSGRSDNHGGSDIQMTQ

SPSSLSASVGDRVTITCRASQSISSYLNWYQQKPGKAPKLLIYAASSLQS

GVPSRFSGSGSGTDFTLTISSLQPEDFATYYCQQDNGYPSTFGGGTKVEI

KRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVT

KSFNRGEC

In some embodiments, activatable anti-PDL1 antibody includes an amino acid sequence that is at least 90%, 91%, 92%, 93%, 94%, 95%, 96%, 97%, 98% or 99% identical to an amino acid sequence of SEQ ID NOs: 46, 137, XX, 432, 428 and 1008.

Anti-PDL1 Antibodies

Exemplary anti-PDL1 antibodies useful in the construction of an activatable anti-PDL1 antibody described herein include antibodies C5H9 v2, C5H9, C5B10, C5E10, and G12H9. The VH and VL CDRs of C5H9 v2, C5H9, C5B10, C5E10, and G12H9 are shown below shown in a single row in Table 1

TABLE 1

| AB Name | VL | | | VH | | |
| --- | --- | --- | --- | --- | --- | --- |
| | CDR1 (SEQ ID NO) | CDR2 (SEQ ID NO) | CDR3 (SEQ ID NO) | CDR1 (SEQ ID NO) | CDR2 (SEQ ID NO) | CDR3 (SEQ ID NO) |
| C5H9 | RASQSISSYLN (209) | YASTLQS (227) | DNGYPST (228) | SYAMS (212) | SSIWRNGIVTVYADS (246) | WSAAFDY (235) |
| C5B10 | RASQSISSYLN (209) | YASTLQS (227) | DNGYPST (228) | SYAMS (212) | SSIWRNGIVTVYADS (246) | WSAGYDY (236) |

TABLE 1-continued

| | VL | | | VH | | |
|---|---|---|---|---|---|---|
| AB Name | CDR1 (SEQ ID NO) | CDR2 (SEQ ID NO) | CDR3 (SEQ ID NO) | CDR1 (SEQ ID NO) | CDR2 (SEQ ID NO) | CDR3 (SEQ ID NO) |
| C5E10 | RASQSISSYLN (209) | YASTLQS (227) | DNGYPST (228) | SYAMS (212) | SSIWRNGIVTVYADS (246) | WSKGFDY (237) |
| G12H9 | RASQSISSYLN (209) | YASTLQS (227) | DNGYPST (228) | SYAMS (212) | SSIWYQGLVTVYADS (247) | WSAAFDY (235) |
| C5H9v2 | RASQSISSYLN (209) | AASSLQS (215) | DNGYPST (228) | SYAMS (212) | SSIWRNGIVTVYADS (246) | WSAAFDY (235) |

Variable heavy and light chain amino acid sequences for anti-PDL1 antibodies C5H9 v2, C5H9, C5B10, C5E10, and G12H9 are shown below.

Anti-PDL1 Light Chain Variable Sequence of C5H9v2
(SEQ ID NO: 58)
DIQMTQSPSSLSASVGDRVTITCRASQSISSYLNWYQQKPGKAPKLLIYA

ASSLQSGVPSRFSGSGSGTDFTLTISSLQPEDFATYYCQQDNGYPSTFG

GTKVEIKR

Anti-PDL1 Heavy Chain Variable Sequence of C5H9
and C5H9v2
(SEQ ID NO: 46)
EVQLLESGGGLVQPGGSLRLSCAASGFTFSSYAMSWVRQAPGKGLEWVSS

IWRNGIVTVYADSVKGRFTISRDNSKNTLYLQMNSLRAEDTAVYYCAKWS

AAFDYWGQGTLVTVSS

Anti-PDL1 Light Chain Variable Sequence of C5H9,
C5B10, C5E10 and G12H9
(SEQ ID NO: 12)
DIQMTQSPSSLSASVGDRVTITCRASQSISSYLNWYQQKPGKAPKLLIYY

ASTLQSGVPSRFSGSGSGTDFTLTISSLQPEDFATYYCQQDNGYPSTFGQ

GTKVEIKR

Anti-PDL1 Heavy Chain Variable Sequence C5B10
(SEQ ID NO: 48)
EVQLLESGGGLVQPGGSLRLSCAASGFTFSSYAMSWVRQAPGKGLEWVSS

IWRNGIVTVYADSVKGRFTISRDNSKNTLYLQMNSLRAEDTAVYYCAKWS

AGYDYWGQGTLVTVSS

Anti-PDL1 Heavy Chain Variable Sequence C5E10
(SEQ ID NO: 50)
EVQLLESGGGLVQPGGSLRLSCAASGFTFSSYAMSWVRQAPGKGLEWVSS

IWRNGIVTVYADSVKGRFTISRDNSKNTLYLQMNSLRAEDTAVYYCAKWS

KGFDYWGQGTLVTVSS

Anti-PDL1 Heavy Chain Variable Sequence G12H9
(SEQ ID NO: 52)
EVQLLESGGGLVQPGGSLRLSCAASGFTFSSYAMetSWVRQAPGKGLEWV SSIWYQGLVTVYADSVKGRFTISRDNSKNTLYLQMetNSLRAEDTAVYYC

AKWSAAFDYWGQGTLVTVSS

In some embodiments, anti-PDL1 antibody includes an amino acid sequence that is at least 90%, 91%, 92%, 93%, 94%, 95%, 96%, 97%, 98% or 99% identical to an amino acid sequence of SEQ ID NOs: 58, 46, 12, 48, 50 and 52.

Masking Moieties

The activatable anti-PDL1 antibodies provided herein include a masking moiety (MM). In some embodiments, the masking moiety is an amino acid sequence (i.e. peptide) that is coupled or otherwise attached to the anti-PDL1 antibody and is positioned within the activatable anti-PDL1 antibody construct such that the masking moiety reduces the ability of the anti-PDL1 antibody to specifically bind PDL1. Suitable masking moieties are identified using any of a variety of known techniques. For example, peptide masking moieties are identified using the methods described in PCT Publication No. WO 2009/025846 by Daugherty et al., the contents of which are hereby incorporated by reference in their entirety.

The MM is a polypeptide of about 2 to 40 amino acids in length. Preferably, the MM is a polypeptide of up to about 40 amino acids in length.

In some embodiments, the MM polypeptide sequence is different from that of PDL1. In some embodiments, the MM polypeptide sequence is no more than 50% identical to any PDL1. In some embodiments, the MM polypeptide sequence is no more than 40%, 30%, 25%, 20%, 15%, or 10% identical to PDL1.

Exemplary MM include: YCEVSELFVLPWCMG (SEQ ID NO: 208), SCLMHPHYAHDYCYV (SEQ ID NO: 426), LCEVLMLLQHPWCMG (SEQ ID NO: 59), IACRHFMEQLPFCHH (SEQ ID NO: 60), FGPRCGEAST-CVPYE (SEQ ID NO: 61), ILYCDSWGAGCLTRP (SEQ ID NO: 62), GIALCPSHFCQLPQT (SEQ ID NO: 63), DGPRCFVSGECSPIG (SEQ ID NO: 64), LCYKLDYDD-RSYCHI (SEQ ID NO: 65), PCHPHPYDARPYCNV (SEQ ID NO: 66), PCYWHPFFAYRYCNT (SEQ ID NO: 67), VCYYMDWLGRNWCSS (SEQ ID NO: 68), LCDLFKL-REFPYCMG (SEQ ID NO: 69), YLPCHFVPIGACNNK (SEQ ID NO: 70), IFCHMGVVVPQCANY (SEQ ID NO: 71), ACHPHPYDARPYCNV (SEQ ID NO: 72), PCHPA-PYDARPYCNV (SEQ ID NO: 73), PCHPHAY-DARPYCNV (SEQ ID NO: 74), PCHPHPADARPYCNV (SEQ ID NO: 75), PCHPHPYAARPYCNV (SEQ ID NO: 76), PCHPHPYDAAPYCNV (SEQ ID NO: 77), PCHPHPYDARPACNV (SEQ ID NO: 78), PCHPHPY-DARPYCAV (SEQ ID NO: 79), PCHAHPYDARPYCNV (SEQ ID NO: 80), and PCHPHPYDARAYCNV (SEQ ID NO: 81).

An preferred MM includes GIALCPSHFCQLPQT (SEQ ID NO: 63).

In some embodiments, the MM comprises an amino acid sequence that is at least 90%, 91%, 92%, 93%, 94%, 95%, 96%, 97%, 98% or 99% identical to an amino acid sequence of SEQ ID NOs: 59-81, 208, and 426.

Cleavable Moieties

The activatable anti-PDL1 antibodies provided herein include a cleavable moiety (CM). In some embodiments, the cleavable moiety includes an amino acid sequence that is a substrate for a protease, usually an extracellular protease. Suitable substrates are identified using any of a variety of known techniques. For example, peptide substrates are identified using the methods described in U.S. Pat. No. 7,666,817 by Daugherty et al.; in U.S. Pat. No. 8,563,269 by Stagliano et al.; and in PCT Publication No. WO 2014/026136 by La Porte et al., the contents of each of which are hereby incorporated by reference in their entirety. (See also Boulware et al. "Evolutionary optimization of peptide substrates for proteases that exhibit rapid hydrolysis kinetics." Biotechnol Bioeng. 106.3 (2010): 339-46).

In some embodiments, the protease that cleaves the CM is active, e.g., up-regulated, in diseased tissue, and the protease cleaves the CM in the activatable antibody when the activatable antibody is exposed to the protease.

In some embodiments, the protease is co-localized with PDL1 in a tissue, and the protease cleaves the CM in the activatable antibody when the activatable antibody is exposed to the protease.

In some embodiments, the protease is present at relatively higher levels in or in close proximity to target-containing tissue of a treatment site or diagnostic site than in tissue of non-treatment sites (for example in healthy tissue), and the protease cleaves the CM in the activatable antibody when the activatable antibody is exposed to the protease.

Exemplary CMs include: LSGRSDNH, (SEQ ID NO: 341), TGRGPSWV, (SEQ ID NO: 338), PLTGRSGG, (SEQ ID NO: 344), TARGPSFK, (SEQ ID NO: 340), NTLSGRSENHSG, (SEQ ID NO: 435), NTLSGRSGNHGS, (SEQ ID NO: 436), TSTSGRSANPRG, (SEQ ID NO: 437), TSGRSANP, (SEQ ID NO: 438), VHMPLGFLGP, (SEQ ID NO: 352), AVGLLAPP, (SEQ ID NO: 372), AQNLLGMV, (SEQ ID NO: 360), QNQALRMA, (SEQ ID NO: 359), LAAPLGLL, (SEQ ID NO: 371), STFPFGMF, (SEQ ID NO: 361), ISSGLLSS, (SEQ ID NO: 364), PAGLWLDP, (SEQ ID NO: 374), VAGRSMRP, (SEQ ID NO: 439), VVPEGRRS, (SEQ ID NO: 440), ILPRSPAF, (SEQ ID NO: 441), MVLGRSLL, (SEQ ID NO: 442), QGRAITFI, (SEQ ID NO: 443), SPRSIMLA, (SEQ ID NO: 444), SMLRSMPL, (SEQ ID NO: 445), ISSGLLSGRSDNH, (SEQ ID NO: 377), AVGLLAPPGGLSGRSDNH, (SEQ ID NO: 383), ISSGLLSSGGSGGSLSGRSDNH, (SEQ ID NO: 378), LSGRSGNH, (SEQ ID NO: 883), SGRSANPRG, (SEQ ID NO: 884), LSGRSDDH, (SEQ ID NO: 885), LSGRSDIH, (SEQ ID NO: 886), LSGRSDQH, (SEQ ID NO: 887), LSGRSDTH, (SEQ ID NO: 888), LSGRSDYH, (SEQ ID NO: 889), LSGRSDNP, (SEQ ID NO: 890), LSGRSANP, (SEQ ID NO: 891), LSGRSANI, (SEQ ID NO: 892), LSGRSDNI, (SEQ ID NO: 893), MIAPVAYR, (SEQ ID NO: 894), RPSPMWAY, (SEQ ID NO: 895), WATPRPMR, (SEQ ID NO: 896), FRLLDWQW, (SEQ ID NO: 897), ISSGL, (SEQ ID NO: 898), ISSGLLS, (SEQ ID NO: 899), ISSGLL, (SEQ ID NO: 900), ISSGLLSGRSANPRG, (SEQ ID NO: 901), AVGLLAPPTSGRSANPRG, (SEQ ID NO: 902), AVGLLAPPSGRSANPRG, (SEQ ID NO: 903), ISSGLLSGRSDDH, (SEQ ID NO: 904), ISSGLLSGRSDIH, (SEQ ID NO: 905), ISSGLLSGRSDQH, (SEQ ID NO: 906), ISSGLLSGRSDTH, (SEQ ID NO: 907), ISSGLLSGRSDYH, (SEQ ID NO: 908), ISSGLLSGRSDNP, (SEQ ID NO: 909), ISSGLLSGRSANP, (SEQ ID NO: 910), ISSGLLSGRSANI, (SEQ ID NO: 911), AVGLLAPPGGLSGRSDDH, (SEQ ID NO: 912), AVGLLAPPGGLSGRSDIH, (SEQ ID NO: 913), AVGLLAPPGGLSGRSDQH, (SEQ ID NO: 914), AVGLLAPPGGLSGRSDTH, (SEQ ID NO: 915), AVGLLAPPGGLSGRSDYH, (SEQ ID NO: 916), AVGLLAPPGGLSGRSDNP, (SEQ ID NO: 917), AVGLLAPPGGLSGRSANP, (SEQ ID NO: 918), AVGLLAPPGGLSGRSANI, (SEQ ID NO: 919), ISSGLLSGRSDNI, (SEQ ID NO: 920), AVGLLAPPGGLSGRSDNI, (SEQ ID NO: 921), GLSGRSDNHGGAVGLLAPP (SEQ ID NO: 1009), and GLSGRSDNHGGVHMPLGFLGP (SEQ ID NO: 1010).

A preferred CM includes ISSGLLSGRSDNH, (SEQ ID NO: 377).

Spacers and Linkers

Linkers suitable for use in compositions described herein are generally ones that provide flexibility of the modified AB or the activatable antibodies to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, or 20 amino acids in length.

Exemplary flexible linkers include glycine polymers $(G)_n$, glycine-serine polymers including, for example, $(GS)_n$, $(GSGGS)_n$ (SEQ ID NO: 191) and $(GGGS)_n$ (SEQ ID NO: 192), where n is an integer of at least one, Gly-Gly-Ser-Gly (SEQ ID NO: 193), Gly-Gly-Ser-Gly-Gly (SEQ ID NO: 194), Gly-Ser-Gly-Ser-Gly (SEQ ID NO: 195), Gly-Ser-Gly-Gly-Gly (SEQ ID NO: 196), Gly-Gly-Gly-Ser-Gly (SEQ ID NO: 197), Gly-Ser-Ser-Ser-Gly (SEQ ID NO: 198), and the like. GlycineGlycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). The ordinarily skilled artisan will recognize that design of an activatable antibodies can include linkers that are all or partially flexible, such that the linker can include a flexible linker as well as one or more portions that confer less flexible structure to provide for a desired activatable antibodies structure.

In some embodiments, at least one of L1 or L2 comprises an amino acid sequence selected from the group consisting of $(GS)_n$, $(GGS)_n$, $(GSGGS)_n$ (SEQ ID NO: 191) and $(GGGS)_n$ (SEQ ID NO: 192), where n is an integer of at least one.

In some embodiments, at least one of L1 or L2 comprises an amino acid sequence selected from the group consisting of GGSG (SEQ ID NO: 193), GGSGG (SEQ ID NO: 194), GSGSG (SEQ ID NO: 195), GSGGG (SEQ ID NO: 196), GGGSG (SEQ ID NO: 197), and GSSSG (SEQ ID NO: 198).

In some embodiments, L1 comprises the amino acid sequence GSSGGSGGSGGSG (SEQ ID NO: 199), GSSGGSGGSGG (SEQ ID NO: 200), GSSGGSGGSGGS (SEQ ID NO: 201), GSSGGSGGSGGSGGGS (SEQ ID NO: 202), GSSGGSGGSG (SEQ ID NO: 203), or GSSGGSGGSGS (SEQ ID NO: 204).

In some embodiments, L2 comprises the amino acid sequence GSS, GGS, GGGS (SEQ ID NO: 205), GSSGT (SEQ ID NO: 206) or GSSG (SEQ ID NO: 207).

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer is joined directly to the MM of the activatable antibody in the structural arrangement from N-terminus to C-terminus of spacer-MM-CM-AB. An example of a spacer joined directly to the N-terminus of MM of the activatable antibody is for example QGQSGS (SEQ ID NO: 923); GQSGS (SEQ ID NO: 1192); QSGS (SEQ ID NO: 1193); SGS (SEQ ID NO: 1194); GS (SEQ ID NO: 1195); S; QGQSGQG (SEQ ID NO: 924); GQSGQG (SEQ ID NO: 395); QSGQG (SEQ ID NO: 925); SGQG (SEQ ID NO: 926); GQG (SEQ ID NO: 927); QG (SEQ ID NO: 928); G; QGQSGQ (SEQ ID NO: 1196); GQSGQ (SEQ ID NO: 1197); QSGQ (SEQ ID NO: 1198); SGQ; GQ (SEQ ID NO: 1199); and Q.

A preferred spacer includes QGQSGS (SEQ ID NO: 923).

In some embodiments, the activatable antibody does not include a spacer sequence.

Method of Treatment

The invention provides methods of preventing, delaying the progression of, treating, alleviating a symptom of, or otherwise ameliorating an PDL1 mediated disease in a subject by administering a therapeutically effective amount of activatable anti-PDL1 antibody described herein to a subject in need thereof. The invention provides uses the activatable anti-PDL1 antibody described herein in delaying the progression of, treating, alleviating a symptom of, or otherwise ameliorating an PDL1 mediated disease in a subject by administering a therapeutically effective amount of activatable anti-PDL1 antibody. A therapeutically effective amount is described infra in the section entitled Dosage and Administration.

PDL1 is known to be expressed in a variety of cancers. (See. e.g., Chen et al., "Molecular Pathways: Next-Generation Immunotherapy—Inhibiting Programmed Death-Ligand 1 and Programmed Death-1," Clin. Can. Res., vol. 18: 6580-6587 (2012), the contents of which are hereby incorporated by reference in their entirety).

Cancers suitable for delaying the progression of, treating, alleviating a symptom of in accordance to the methods of the invention include for example, but are not limited to is anal squamous cell carcinoma, basal cell carcinoma, bladder cancer, bone cancer, bowel carcinoma, breast cancer, carcinoid, castration-resistant prostate cancer (CRPC), cervical carcinoma, colorectal cancer (CRC), colon cancer cutaneous squamous cell carcinoma, endometrial cancer, esophageal cancer, gastric carcinoma, gastroesophageal junction cancer, glioblastoma/mixed glioma, glioma, head and neck cancer, hepatocellular carcinoma, hematologic malignancy, liver cancer, lung cancer, melanoma, Merkel cell carcinoma, multiple myeloma, nasopharyngeal cancer, osteosarcoma, ovarian cancer, pancreatic cancer, peritoneal carcinoma, undifferentiated pleomorphic sarcoma, prostate cancer, rectal carcinoma, renal cancer, sarcoma, salivary gland carcinoma, squamous cell carcinoma, stomach cancer, testicular cancer, thymic carcinoma, thymic epithelial tumor, thymoma, thyroid cancer, urogenital cancer, urothelial cancer, uterine carcinoma, or uterine sarcoma.

In some embodiments, the cancer is a High Tumor Mutational Burden (hTMB) cancer.

In other embodiments breast cancer is triple negative breast cancer or estrogen receptor positive breast cancer. The hematologic malignancy is a lymphoma, a leukemia or multiple myeloma. Lymphoma include a B-cell lymphoma, a T-cell lymphoma, Hodgkin's lymphoma, or an EBV lymphoma, primary mediastinal B-cell lymphoma. In some embodiments, the Hodgkin lymphoma is post allo-HSCT.

The bowel carcinoma is for example small bowel carcinoma or small bowel adenocarcinoma.

A head and neck cancer includes for example a head and neck squamous cell carcinoma. The esophageal cancer is for example esophageal carcinoma.

The colon cancer is for example is colon adenocarcinoma,

The lung cancer is for example, non-small cell lung cancer (NSCLC) or small cell lung cancer.

The NSCLC is non-squamous NSCLC or squamous NSCLC.

The prostate cancer is for example small cell neuroendocrine prostate cancer.

In some embodimenst the cancer is a carcinoma such as for example, squamous cell carcinoma.

In other embodiments the cancer is renal cancer such as renal cell carcinoma or renal sarcoma Cancers particularly suitable in the practice of the methods and uses of the invention include undifferentiated pleomorphic sarcoma, small bowel adenocarcinoma, Merkel cell carcinoma, thymic carcinoma, anal squamous cell carcinoma, cutaneous squamous cell carcinoma and triple negative breast cancer.

In some embodiments, the cancer is gastric cancer or gastroesophageal junction cancer.

In some embodiments, the gastric cancer or gastroesophageal cancer is an advanced unresectable cancer with a Siewert classification of II/III for those with a significant esophageal component.

In some embodiments, the cancer is a thymoma or thymic cancer. The thymic cancer is a thymicepithelial tumor.

In some embodiments, the cancer is a melanoma. In some embodiments, the cancer is an ocular melanoma.

B-cell lymphoma, T-cell lymphoma, Hodgkin's lymphoma/primary mediastinal B-cell lymphoma, and chronic myelogenous leukemia.

In some embodiments, the cancer is due to a PDL1-expressing tumor.

The cancer is an advanced, unresectable solid tumor or lymphoma. The advanced unresectable tumor is a PDL1-responsive tumor type.

In some embodiments, the subject has an unresectable solid tumor with no further standard of care available. In some embodiments, the subject has a lymphoma with no further standard of care available. In some embodiments, the subject is immunotherapy naïve. In some embodiments, PDL1/PD1 inhibitor therapy is not approved for the subject's cancer.

In some embodiments, the PDL1 status of the subject and/or tumor is unknown. In some embodiments, the subject and/or tumor is PDL1 positive (PDL1+), e.g., the subject has a tumor proportion score of at least 1% membranous staining.

An activatable anti-PDL1 antibody used in any of the embodiments of these methods and uses can be administered at any stage of the disease. For example, such an activatable anti-PDL1 antibody can be administered to a patient suffering cancer of any stage, from early to metastatic. In some embodiments, the cancer comprises advanced or recurrent solid tumors or lymphomas. In some embodiments, the subject has an unresectable solid tumor.

The invention also provides methods of treating cancer patients with an autoimmune or inflammatory disease by administering a therapeutically effective amount of an activatable anti-PDL1 antibody described herein to a subject in need thereof. In some embodiments, the autoimmune disease is colitis, RA, pancreatitis, diabetes, or pneumonitis.

In some embodiments, the subject is a mammal, such as a human, non-human primate, companion animal (e.g., cat, dog, horse), farm animal, work animal, or zoo animal. In some embodiments, the subject is a human. In some embodiments, the subject is a companion animal. In some embodiments, the subject is an animal in the care of a veterinarian. Preferably, the subject is a human.

In various embodiments the subjects exhibits one or more of the following characteristics: is PD-1/PDL1 inhibitor-naïve, is CTLA-4 inhibitor-naïve, is BRAF$^{V600E}$ mutation positive, is BRAF inhibitor-naïve, or is immunotherapy naïve.
is PDL1 positive, is PDL1 unknown or has been previously treated with a PD1/PDL1 inhibitor.

In some embodiments the subject has no further standard of care available.

In other embodimenst the subject has been previously treated with a PD-1/PDL1 inhibitor, and the treatment with the PD-1/PDL1 inhibitor was discontinued for reasons other than toxicity.

The method of any one of the preceding claims, wherein the subject is immunotherapy naïve.

The activatable anti-PDL1 antibody and therapeutic formulations thereof are administered to a subject suffering from or susceptible to a disease or disorder associated with aberrant PDL1 expression and/or activity. A subject suffering from or susceptible to a disease or disorder associated with aberrant PDL1 expression and/or activity is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

Administration of an activatable anti-PDL1 antibody to a patient suffering from a disease or disorder associated with aberrant PDL1 expression and/or activity is considered successful if any of a variety of laboratory or clinical objectives is achieved. For example, administration of an activatable anti-PDL1 antibody to a patient suffering from a disease or disorder associated with aberrant PDL1 expression and/or activity is considered successful if one or more of the symptoms associated with the disease or disorder is alleviated, reduced, inhibited or does not progress to a further, i.e., worse, state. Administration of an activatable anti-PDL1 antibody to a patient suffering from a disease or disorder associated with aberrant PDL1 expression and/or activity is considered successful if the disease or disorder enters remission or does not progress to a further, i.e., worse, state.

Dosage and Administration

The cancer therapy provided herein, containing an activatable anti-PDL1 antibody, is administered in an amount sufficient to exert a therapeutically useful effect. Typically, the active agents are administered in an amount that does not result in undesirable side effects of the patient being treated, or that minimizes or reduces the observed side effects.

It is within the level of one of skill in the art to determine the precise amounts of active agents, including activatable anti-PDL1 antibodies to be administered to a subject. For example, such agents and uses for treating solid tumors and lymphomas, are well-known in the art. Thus, dosages of such agents can be chosen based on standard dosing regimens for that agent under a given route of administration.

It is understood that the precise dosage and duration of treatment is a function of the tissue or tumor being treated and may be determined empirically using known testing protocols or by extrapolation from in vivo or in vitro test data and/or can be determined from known dosing regimens of the particular agent. It is to be noted that concentrations and dosage values may also vary with the age of the individual treated, the weight of the individual, the route of administration and/or the extent or severity of the disease and other factors that are within the level of a skilled medical practitioner to consider. Generally, dosage regimens are chosen to limit toxicity. It should be noted that the attending physician would know how to and when to terminate, interrupt or adjust therapy to lower dosage due to toxicity, or bone marrow, liver or kidney or other tissue dysfunctions. Conversely, the attending physician would also know how to and when to adjust treatment to higher levels if the clinical response is not adequate (precluding toxic side effects). It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope thereof.

For example, activatable anti-PDL1 antibodies, is administered in a therapeutically effective amount to decrease the tumor volume.

The amount of an activatable anti-PDL1 antibodies is administered for the treatment of a disease or condition, can be determined by standard clinical techniques. In addition, in vitro assays and animal models can be employed to help identify optimal dosage ranges. The precise dosage, which can be determined empirically, can depend on the route of administration, the type of disease to be treated and the seriousness of the disease.

The activatable anti-PDL1 antibodies provided herein are administered intravenously. For intravenous administration, the conjugate can be administered by push or bolus, by infusion, or via a combination thereof. The infusion time can be about 1 minute to three hours, such as about 1 minute to about two hours, or about 1 minute to about 60 minutes, or at least 10 minutes, 40 minutes, or 60 minutes.

The dosage amount is between 0.03 mg/kg and 30 mg/kg. In other embodiments, the dosage amount is between 0.3 mg/kg and 30 mg/kg. In further embodiments, the dosage amount is between 3 mg/kg and 30 mg/kg; 3 mg/kg and 20 mg/kg; 3 mg/kg and 15 mg/kg, or 3 mg/kg and 10 mg/kg. In some embodiments, the dosage amount is between 5 mg/kg and 30 mg/kg; 5 mg/kg and 30 mg/kg; 5 mg/kg and 20 mg/kg; 5 mg/kg and 15 mg/kg; or 5 mg/kg and 10 mg/kg. In other embodiments, the dosage amount is between 10 mg/kg and 30 mg/kg; 10 mg/kg and 20 mg/kg; or 10 mg/kg and 15 mg/kg.

For example, the dosage amount is 0.03 mg/kg, 0.10 mg/kg, 0.3 mg/kg, 1.0 mg/kg, 3.0 mg/kg, 10.0 mg/kg, or 30.0 mg/kg. The dosage amount is 1 mg/kg, 3 mg/kg, 6 mg/kg, or 15.0 mg/kg. Preferably, the dosage amount is 10 mg/kg.

The activatable anti-PDL1 antibodies provided herein are administered at a fixed dose A fixed dosage is based for example upon a 65 kg human, a 70 kg human, a 75 kg human or an 80 kg human and the mg/kg dosages described herein.

For example, when the fixed dose is bases upon an 80 kg human and the desired mg/kg doses is 10 mg/kg then the fixed dose is 800 mg.

A fixed dosage is between 240 mg and 2400 mg. exemplary fixed dosages include 240 mg, 480 mg, 800 mg, 1200 mg and 2400 mg.

The frequency and timing of administration, and the dosage amounts, can be administered periodically over a cycle of administration to maintain a continuous and/or long term effect of the active agents for a desired length of time. The provided compositions of activatable anti-PDL1 antibodies can be administered hourly, daily, weekly, bi-weekly, monthly, yearly or once. The length of time of the cycle of administration can be empirically determined, and is dependent on the disease to be treated, the severity of the disease, the particular patient, and other considerations within the level of skill of the treating physician. The length of time of treatment with a combination therapy provided herein can be one week, two weeks, one months, several months, one year, several years or more.

The frequency of administration of the activatable anti-PDL1 antibodies is between once a day and every 28 day; between once a day and once a month, between once a week and once a month; between once a week and once every two months.

For example, the frequency of administration of the activatable anti-PDL1 antibodies is once a day, every other day, twice weekly, once weekly, once every 2 weeks, once every 3 weeks, once every 4 weeks, once every 5 weeks, once every six weeks, once every seven weeks, once every eight weeks. Put another way the frequency of administration of the activatable anti-PDL1 antibodies is once a day, every other day, twice weekly, once every 7 days, once every 14 days, once every 21 days, once every 28 days once every 35 days, once every 42 days, once every 49 days, once every 56 days. The dosages can be divided into a plurality of cycles of administration during the course of treatment. For example, the activatable anti-PDL1 antibodies can be administered at the frequency over a period of about a month, 2 months, 3 months, 4 months, 5 months, 6 months, a year or more. The frequency of administration can be the same throughout the period of the cycle or can differ. For example, an exemplary dosage frequency is two times a week at least for a first week of a cycle of administration. After the first week, the frequency can continue at twice a week, can increase to more than twice a week, or can be reduced to no more than once a week. It is within the level of a skilled person to determine the particular dosage frequency and cycle of administration based on the particular dosage being administered, the disease or condition being treated, the severity of the disease or condition, the age of the subject and other similar factors.

If disease symptoms persist in the absence of discontinued treatment, treatment can be continued for an additional length of time. Over the course of treatment, evidence of disease and/or treatment-related toxicity or side effects can be monitored.

The cycle of administration of the activatable anti-PDL1 antibodies can be tailored to add periods of discontinued treatment in order to provide a rest period from exposure to the agents. The length of time for the discontinuation of treatment can be for a predetermined time or can be empirically determined depending on how the patient is responding or depending on observed side effects. For example, the treatment can be discontinued for one week, two weeks, three weeks, one month or several months. Generally, the period of discontinued treatment is built into a cycle of dosing regimen for a patient.

An exemplary dosing regimen is a treatment cycle or cycle of administration of 14 days. The activatable anti-PDL1 antibodies disclosed herein, is administered on day 1, followed by 13 days without dosing. It is within the level of one of skill in the art to determine the precise cycle of administration and dosing schedule.

As noted above, the cycle of administration can be for any desired length of time. Hence, the 14-day cycle of administration can be repeated for any length of time. It is within the level of skill of the treating physician to adopt a cycle of administration and dosing regimen that meets the needs of the patient depending on personal considerations specific to the patient and disease to be treated.

In some embodiments, activatable anti-PDL1 antibodies described herein are used as sole active agents, i.e., monotherapy. Alternatively the activatable anti-PDL1 antibodies described herein are used in conjunction with one or more additional agents or a combination of additional agents, i.e. combination therapy or co-therapy Suitable additional agents include current pharmaceutical and/or surgical therapies for an intended application, such as, for example, cancer. For example, the activatable anti-PDL1 antibodies can be used in conjunction with an additional chemotherapeutic anti-neoplastic agent or radiation.

In some embodiments, activatable anti-PDL1 antibody is administered before and/or during and/or after treatment in combination with one or more additional agent (s) (e.g., combination therapy)

Non-limiting examples, of additional agents include a chemotherapeutic agent, radiation, a checkpoint inhibitor, a kinase inhibitor, an anti-inflammatory agent, an immunosuppressive agent, a T cell agonist, a NK cell agonist, an agent targeting inhibitors in the tumor microenvironment agent effects regulatory T cell depletion an anti-angiogenic agent, agent targeting inhibitors in the tumor microenvironment, a proteosome inhibitor, an anti-metabolite, an anti-microtubule agent, a topoisomerase inhibitor, a vaccine, an oncovirus, a DC-activating agent a cytotoxic antibiotic, and/or any other nucleic acid damaging agent.

In some embodiments, the additional agent(s) is a tumor-targeted antibody designed to kill the tumor via ADCC or via direct conjugation to a toxin (e.g., an antibody drug conjugate (ADC). In some embodiments, the additional agent(s) stimulates co-stimulatory molecules. In some embodiments, the additional agent(s) is an adoptive T cell therapeutic agent that effects adoptive T cell transfer.

In some embodiments, the agent inhibits adenosine A2aR. In some embodiments, the agent inhibits arginase. In some embodiments, the agent inhibits CD39. In some embodiments, the agent inhibits CD73. In some embodiments, the agent inhibits CD47.

In some embodiments the additional agent chemotherapeutic agent. Chemotherapeutic agents include for example an alkylating agents, taxanes Alkylating agents include for example, platinum-based chemotherapy, such as carboplatin or cisplatin, oxaliplatin, Taxanes include for example, docetaxel, paclitaxel, Abraxane®). (i.e., albumin-conjugated paclitaxel). Other chemotherapeutic agents include, doxorubicin, irinotecan, gemcitabine and any chemotherapeutic agents know to those skilled in the art.

A tumor microenvironment inhibitor includes for example an IDO inhibitor, an α-CSF1R inhibitor, an α-CCR4 inhibitor, TGF-beta blockade, a myeloid-derived suppressor cell, or a T-regulatory cell.

In some embodiments, the agonist is selected from the group consisting of Ox40, GITR, CD137, ICOS, CD27, and HVEM.

In some embodiments, the DC-activating agent includes, by way of non-limiting example, a toll-like receptor (TLR) agonist and/or α-CD40.

A checkpoint inhibitor inhibits (e.g. blocks) immune checkpoint proteins. Immune checkpoints include for example, CTLA-4, LAG-3, PD1 (also referred to as PD-1), PDL1, TIGIT, TIM-3, B7H4, and Vista.

Kinase inhibitors inhibits kinases such as B-RAFi, MEKi, and Btk.

Exemplary kinase inhibitors include pazopanib, osimertinib, crizotinib. sorafenib or erlotinib A B-RAFi inhibitor includes for example, vemurafenib. A Btk inhibitor includes for example, ibrutinib. Inhibitor MEKi kinase inhibitors include for example, trametinib, cobimetinib or selumetinib.

In some embodiments, the additional agent is an immune modulating agent, such as lenolidominde or IL-2.

In some embodiments, the additional agent is a proteosome inhibitor, such as bortezomib or carfilzomib.

In some embodiments, the additional agent is an agent considered standard of care by those skilled in the art In some embodiments, the additional agent is a targeted agent, such as another antibody, e.g., a monoclonal antibody (e.g., ipilimumab or bevacizumab), a bispecific antibody, or a multispecific antibody.

Additional agents are administered simultaneously or at different times during a treatment regimen. For example, the activatable anti-PDL1 antibody is administered concurrently with the addition agent, prior to the administration of the additional agent, t or subsequent to the administration of the additional agent, or in an alternating fashion. The additional agent is administered in single dose or in multiple dose.

In some embodiments, the additional agent is a targeted agent, such as another antibody, e.g., a monoclonal antibody (e.g., bevacizumab), a bispecific antibody, or a multispecific antibody. In some embodiments, the additional agent is a proteosome inhibitor, such as bortezomib or carfilzomib. In some embodiments, the additional agent is an immune modulating agent, such as lenolidominde or IL-2. In some embodiments, the additional agent is radiation. In some embodiments, the additional agent is an agent considered standard of care by those skilled in the art. In some embodiments, the additional agent is a chemotherapeutic agent well known to those skilled in the art.

In some embodiments, the additional agent is another antibody or antigen-binding fragment thereof, another conjugated antibody or antigen-binding fragment thereof, another activatable antibody or antigen-binding fragment thereof and/or another conjugated activatable antibody or antigen-binding fragment thereof. In some embodiments the additional agent is another antibody or antigen-binding fragment thereof, another conjugated antibody or antigen-binding fragment thereof, another activatable antibody or antigen-binding fragment thereof and/or another conjugated activatable antibody or antigen-binding fragment thereof against the same target as the first antibody or antigen-binding fragment thereof, the first conjugated antibody or antigen-binding fragment thereof, activatable antibody or antigen-binding fragment thereof and/or a conjugated activatable antibody or antigen-binding fragment thereof, e.g., against PDL1. In some embodiments the additional agent is another antibody or antigen-binding fragment thereof, another conjugated antibody or antigen-binding fragment thereof, another activatable antibody or antigen-binding fragment thereof and/or another conjugated activatable antibody or antigen-binding fragment thereof against a target different than the target of the first antibody or antigen-binding fragment thereof, the first conjugated antibody or antigen-binding fragment thereof, activatable antibody or antigen-binding fragment thereof and/or a conjugated activatable antibody or antigen-binding fragment thereof (i.e., target other than PDL1). In some embodiments, the additional agent is a multispecific antibody, such as a bispecific antibody. In some embodiments, the additional agent is a multispecific activatable antibody, such as a bispecific activatable antibody.

In some embodiments that additional agent is ipilimumab, a CTLA4-binding fragment of ipilimumab, and/or an ipilimumab activatable antibody.

| CD51 | CYR61 | hGH |

As a non-limiting example, the additional agent is or is derived from an antibody listed in Table 23.

TABLE 22

Exemplary sources for Additional Agenst

| Antibody Trade Name (antibody name) | Target |
|---|---|
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| (Ocrelizumab) | CD20 |
| Arzerra ™ (ofatumumab) | CD20 |
| Gazyva ™ (Obinutuzumab) | CD20 |
| Zenapax ™ (daclizumab) | CD25 |
| Adcetris ™ (brentuximab vedotin) | CD30 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Kadcyla ™ (trastuzumab emtansine) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |
| ICR62 | EGFR |
| mAb 528 | EGFR |
| CH806 | EGFR |
| MDX-447 | EGFR/CD64 |
| (edrecolomab) | EpCAM |

TABLE 22-continued

Exemplary sources for Additional Agenst

| Antibody Trade Name (antibody name) | Target |
|---|---|
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
|  | Notch, e.g., Notch 1 |
|  | Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |
| Opdivo ® (nivolumab) | PD1 |
| Keytruda ® (pembrolizumab) | PD1 |
| pidilizumab | PD1 |
| MEDI0680 | PD1 |
| PDR001 | PD1 |
| REGN2810 | PD1 |
| BGB-A317 | PD1 |
| BI-754091 | PD1 |
| JNJ-63723283 | PD1 |
| MGA012 | PD1 |
| TSR042 | PD1 |
| AGEN2034 | PD1 |
| INCSHR-1210 | PD1 |
| JS001 | PD1 |
| Imfinzi ™ (durvalumab) | PD-L1 |
| Tecentriq ® (atezolizumab) | PD-L1 |
| Bavencio ® (avelumab) | PD-L1 |
| FAZ053 | PD-L1 |
| LY-3300054 | PD-L1 |
| KN035 | PD-L1 |

Additional agents are administered simultaneously or at different times during a treatment regimen. For example, the activatable anti-PDL1 antibody is administered concurrently with the addition agent, prior to the administration of the additional agent, tor subsequent to the administration of the additional agent, or in an alternating fashion. The additional agent is administered in single dose or in multiple dose.

In some embodiments, activatable anti-PDL1 antibody of the disclosure is used in combination with an inhibitor of CTLA-4. In some embodiments, activatable anti-PDL1 antibody of the disclosure is used in combination with an anti-CTLA-4 antibody, such as for example ipilimumab.

The inhibitor of CTLA-4 such as ipilimumab is administered at a dose between 1 mg/kg to 20 mg/kg, between 3 mg/kg to 15 mg/kg, between 3 mg/kg to 10 mg/kg. For example, inhibitor of CTLA-4 such as ipilimumab is administered at a dosage of 1, mg/kg, 2 mg/kg, 3 mg/kg, 4, mg/kg, 5 mg/kg, 6 mg/kg, 7, mg/kg, 8 mg/kg, 9, mg/kg, or 10 mg/kg.

In various embodimenst the anti-CTLA-4 antibody, e.g., ipilimumab is administered at a fixed dose A fixed dosage is based for example upon a 65 kg human, a 70 kg human, a 75 kg human or an 80 kg human and the mg/kg dosages described herein. For example, when the fixed dose is bases upon an 80 kg human and the desired mg/kg dose is 10 mg/kg then the fixes dose is 800 mg. If desired mg/kg dose is 6 mg/kg then the fixes dose is 480 mg. If desired mg/kg dose is 3 mg/kg then the fixed dose is 240 mg. A fixed dosage of the anti-CTLA-4 antibody, e.g., ipilimumab is between 140 mg and 1000 mg. Exemplary fixed dosages include 240 mg, 480 mg, and 800 mg, In some embodimenst, ipilimumab is administered at a higher dose than is the maximum tolerated dose for a given indication. Alternatively, ipilimumab is administered at a lower dose than its maximum tolerated dose for a given indication.

In other embodimenst, ipilimumab is administered at a higher dose than its recommended dose for a given indication. Alternatively, ipilimumab is administered at a lower dose than recommended dose for a given indication.

In some embodiments, the activatable anti-PDL1 antibody and the CTLA-4 inhibitor, e.g., an anti-CTLA-4 antibody, e.g., ipilimumab, are administered intravenously (IV).

The frequency of administration of the anti-CTLA-4 antibody, e.g., ipilimumab is between once a day and every 28 day; between once a day and once a month, between once a week and once a month; between once a week and once every two months. For example, the frequency of administration of the anti-CTLA-4 antibody, e.g., ipilimumab is once a day, every other day, twice weekly, once weekly, once every 2 weeks, once every 3 weeks, once every 4 weeks, once every 5 weeks, once every six weeks, once every seven weeks, once every eight weeks. Put another way the frequency of administration of the activatable anti-CTLA-4 antibody, e.g., ipilimumab is once a day, every other day, twice weekly, once every 7 days, once every 14 days, once every 21 days, once every 28 days once every 35 days, once every 42 days, once every 49 days, once every 56 days.

The activatable anti-PDL1 antibody and the CTLA-4 inhibitor, e.g., an anti-CTLA-4 antibody, e.g., ipilimumab, are administered IV at a regular interval. The activatable anti-PDL1 antibody and the CTLA-4 inhibitor, e.g., an anti-CTLA-4 antibody, e.g., ipilimumab, are administered IV at the same regular interval. Alternatively, the activatable anti-PDL1 antibody and the CTLA-4 inhibitor, e.g., an anti-CTLA-4 antibody, e.g., ipilimumab, are administered IV at different regular intervals.

In some embodiments, the frequency of administration of the activatable anti-PDL1 antibodies is between once a day and every 28 day; between once a day and once a month, between once a week and once a month; between once a week and once every two months and the frequency of administration anti-CTLA-4 antibody, e.g., ipilimumab is every 7 days, every 14 days or every 28 days.

For example, the frequency of administration of the activatable anti-PDL1 antibodies is once a day, every other day, twice weekly, once weekly, once every 2 weeks, once every 3 weeks, once every 4 weeks, once every 5 weeks, once every six weeks, once every seven weeks, once every eight weeks the frequency of administration anti-CTLA-4 antibody, e.g., ipilimumab is every 7 days, every 14 days or every 28 days.

Alternatively, the frequency of administration of the activatable anti-PDL1 antibodies is once a day, every other day, twice weekly, once every 7 days, once every 14 days, once every 21 days, once every 28 days once every 35 days, once every 42 days, once every 49 days, once every 56 days. the frequency of administration anti-CTLA-4 antibody, e.g., ipilimumab is every 7 days, every 14 days or every 28 days.

For example, in some embodiments, the activatable anti-PDL1 antibody and the CTLA-4 inhibitor, e.g., an anti-CTLA-4 antibody, e.g., ipilimumab, are administered IV every 21 days for multiple doses.

For example, in some embodiments, the activatable anti-PDL1 antibody and the CTLA-4 inhibitor, e.g., an anti-CTLA-4 antibody, e.g., ipilimumab, are administered IV every 14 days for multiple doses.

In some embodiments, activatable anti-PDL1 antibody the CTLA-4 inhibitor, e.g., an anti-CTLA-4 antibody, e.g., ipilimumab, are administered IV every 21 days for at least two or more doses, e.g., at least four or more doses. In some embodiments, activatable anti-PDL1 antibody and the CTLA-4 inhibitor, e.g., an anti-CTLA-4 antibody, e.g., ipilimumab, are administered IV every 21 days for four doses.

In some embodiments, the anti-PDL1 antibody, conjugated anti-PDL1 antibody, activatable anti-PDL1 antibody and/or conjugated activatable anti-PDL1 antibody of the disclosure and the CTLA-4 inhibitor, e.g., an anti-CTLA-4 antibody, e.g., ipilimumab, are administered IV every 21 days for at least two or more doses, e.g., at least four doses, followed by administration of the activatable anti-PDL1 antibody as a monotherapy for a desired period of time In some embodiments, the anti-PDL1 antibody, conjugated anti-PDL1 antibody, activatable anti-PDL1 antibody and/or conjugated activatable anti-PDL1 antibody of the disclosure is administered IV at a dosage or 0.3 mg/kg, 1.0 mg/kg, 3.0 mg/kg, 10.0 mg/kg, and 30.0 mg/kg, and the CTLA-4 inhibitor, e.g., an anti-CTLA-4 antibody, e.g., ipilimumab, is administered IV at a dose of 3 mg/kg. In some embodiments, activatable anti-PDL1 antibody is administered IV at a dose 10.0 mg/kg, and, 6 mg/kg. or 10 mg/kg 10a dosage or, 6 mg/kg or 10 mg/kg In some embodiments, the activatable anti-PDL1 antibody and the CTLA-4 inhibitor, e.g., an anti-CTLA-4 antibody, e.g., ipilimumab, are administered according to the dosing and/or administration schedule shown in FIG. 1, Part B1 or Part B2 and described in Example 2. In any of these embodiments described herein, an anti-PDL1 activatable antibody of the disclosure is used. In an exemplary embodiment, the activatable anti-PDL1 antibody is PL07-2001-C5H9v2.

For example multiple doses of the activatable antibody and the anti-CTLA-4 antibody are administered over a first period of time, followed by administration of multiple doses of the activatable anti-PDL1 antibody as a monotherapy over a second period of time.

For example, a dose of the activatable antibody and a dose of the anti-CTLA-4 antibody are administered concomitantly as a combination therapy every 21 days for 4 doses, followed by administration of a dose of the activatable anti-PDL1 antibody as a monotherapy every 14 days.

In some embodiments, multiple doses of the activatable anti-PDL1 antibody as a monotherapy is administered over a first period of time, followed by concomitant administration of multiple doses of the activatable anti-PDL1 antibody and the anti-CTLA-4 antibody as a combination therapy over a second period of time.

For example multiple doses of the activatable antibody are administers as a monotherapy over a first period of time and subsequently multiple doses of the activatable antibody and the anti-CTLA-4 antibody as a combination therapy are administered over a second period of time, followed by administering multiple doses of the activatable antibody as a monotherapy over a third period of time.

In some embodimenst the activatable antibody is administered as a monotherapy every 14 days for 4 doses, followed by administration of a dose of activatable antibody and a dose of anti-CTLA-4 antibody as a combination therapy every 21 days, for 4 doses, followed by administration of a dose an activatable antibody as a monotherapy every 14 days.

In some embodiments, activatable anti-PDL1 antibody is used in combination with a B-RAF inhibitor. In some embodiments, activatable anti-PDL1 antibody of the disclosure is used in combination with vemurafenib In some embodiments, t activatable anti-PDL1 antibody is administered intravenously (IV), and the B-RAF inhibitor, e.g., vemurafenib, is administered by mouth (PO). In some embodiments, the activatable anti-PDL1 antibody is administered IV, and multiple doses, e.g., two or more doses, of the B-RAF inhibitor, e.g., vemurafenib, are administered PO daily. In some embodiments, activatable anti-PDL1 antibody is administered IV, and two doses of the B-RAF inhibitor, e.g., vemurafenib, are administered PO daily. In some embodiments, activatable anti-PDL1 antibody is administered IV every 14 days, and two doses of the B-RAF inhibitor, e.g., vemurafenib, are administered PO daily.

In some embodiments, the B-RAF inhibitor, e.g., vemurafenib, is administered PO at a dose of 960 mg-. In some embodiments, the B-RAF inhibitor, e.g., vemurafenib, is administered twice daily PO at a dose of 960 mg.

In some embodiments, the BB-RAF inhibitor, e.g., vemurafenib, is administered PO at a dose of 875 mg-. In some embodiments, the B-RAF inhibitor, e.g., vemurafenib, is administered twice daily PO at a dose of 875 mg In some embodiments, activatable anti-PDL1 antibody is administered IV at a dosage of 1.0 mg/kg, 3.0 mg/kg, 10.0 mg/kg, and 30.0 mg/kg, and the B-RAF inhibitor, e.g., vemurafenib, is administered PO at a dose of 960 mg. other, anti-PDL1 In other embodiments, activatable anti-PDL1 antibody is administered IV at a dosage of 1.0 mg/kg, 3.0 mg/kg, 10.0 mg/kg, and 30.0 mg/kg, and the BB-RAF inhibitor, e.g., vemurafenib, is administered PO at a dose of 875 mg.

In some embodiments, activatable anti-PDL1 antibody is administered IV at a dosage of 10.0 mg/kg, and the B-RAF inhibitor, e.g., vemurafenib, is administered PO at a dose of 960 mg.

In other embodiments, activatable anti-PDL1 antibody is administered IV at a dosage of 10.0 mg/kg and the B-RAF inhibitor, e.g., vemurafenib, is administered PO at a dose of 875 mg.

a dosage of other, anti-PDL1 administered IV at a dosage of 10.0 mg/kg and the B-RAF inhibitor, e.g., vemurafenib, administered PO at a dose of 875 mg In some embodiments, activatable anti-PDL1 antibody and the B-RAF inhibitor, e.g., vemurafenib, are administered according to the dosing and/or administration schedule shown in FIG. 1, Part C and described in Example 1.

Activatable Anti-PDL1 Antibody-Drug Conjugates

The compositions and methods provided herein enable the attachment of one or more agents to one or more cysteine residues in the AB without compromising the activity (e.g., the masking, activating or binding activity) of the activatable anti-PDL1 antibody. In some embodiments, the compositions and methods provided herein enable the attachment of one or more agents to one or more cysteine residues in the AB without reducing or otherwise disturbing one or more disulfide bonds within the MM. The compositions and methods provided herein produce an activatable anti-PDL1 antibody that is conjugated to one or more agents, e.g., any of a variety of therapeutic, diagnostic and/or prophylactic agents, for example, in some embodiments, without any of the agent(s) being conjugated to the MM of the activatable anti-PDL1 antibody. The compositions and methods provided herein produce conjugated activatable anti-PDL1 antibodies in which the MM retains the ability to effectively and efficiently mask the AB of the activatable antibody in an uncleaved state. The compositions and methods provided herein produce conjugated activatable anti-PDL1 antibodies in which the activatable antibody is still activated, i.e., cleaved, in the presence of a protease that can cleave the CM.

In some embodiments, the activatable antibodies described herein also include an agent conjugated to the activatable antibody. In some embodiments, the conjugated agent is a therapeutic agent, such as an anti-inflammatory and/or an antineoplastic agent. In such embodiments, the agent is conjugated to a carbohydrate moiety of the activatable antibody, for example, in some embodiments, where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate).

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

The disclosure also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, dolastatins and derivatives thereof (e.g. auristatin E, AFP, MMAF, MMAE, MMAD, DMAF, DMAE). For example, the agent is monomethyl auristatin E (MMAE) or monomethyl auristatin D (MMAD). In some embodiments, the agent is an agent selected from the group listed in Table 11. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is linked to the AB using a maleimide caproyl-valine-citrulline linker or a maleimide PEG-valine-citrulline linker. In some embodiments, the agent is linked to the AB using a maleimide caproyl-valine-citrulline linker. In some embodiments, the agent is linked to the AB using a maleimide PEG-valine-citrulline linker In some embodiments, the agent is monomethyl auristatin D (MMAD) linked to the AB using a maleimide PEG-valine-citrulline-para-aminobenzyloxycarbonyl linker, and this linker payload construct is referred to herein as "vc-MMAD." In some embodiments, the agent is monomethyl auristatin E (MMAE) linked to the AB using a maleimide PEG-valine-citrulline-para-aminobenzyloxycarbonyl linker, and this linker payload construct is referred to herein as "vc-MMAE." The structures of vc-MMAD and vc-MMAE are shown below:

vc-MMAD:

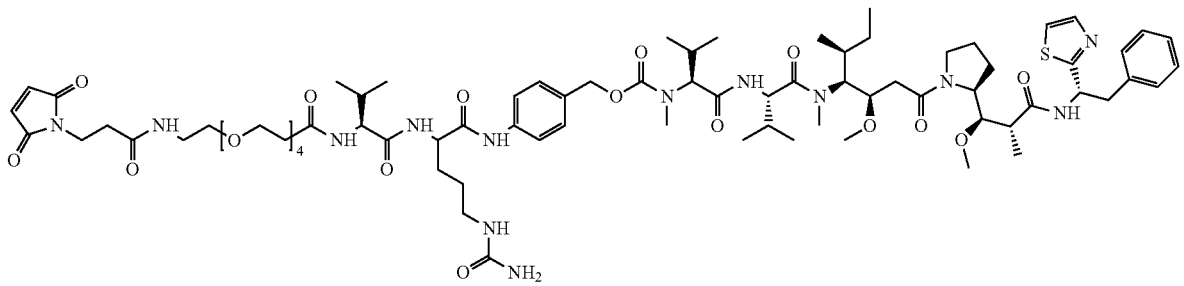

vc-MMAE:

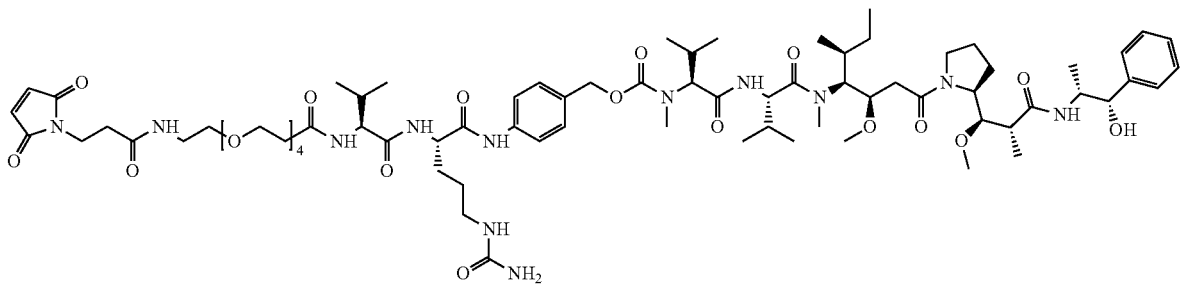

The disclosure also provides conjugated activatable antibodies that include an activatable antibody linked to monomethyl auristatin D (MMAD) payload, wherein the activatable antibody includes an antibody or an antigen binding fragment thereof (AB) that specifically binds to a target, a masking moiety (MM) that inhibits the binding of the AB of the activatable antibody in an uncleaved state to the target, and cleavable moiety (CM) coupled to the AB, and the CM is a polypeptide that functions as a substrate for at least one MMP protease.

In some embodiments, the MMAD-conjugated activatable antibody can be conjugated using any of several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB.

In some embodiments, the polyethylene glycol (PEG) component of a linker of the present disclosure is formed from 2 ethylene glycol monomers, 3 ethylene glycol monomers, 4 ethylene glycol monomers, 5 ethylene glycol monomers, 6 ethylene glycol monomers, 7 ethylene glycol monomers 8 ethylene glycol monomers, 9 ethylene glycol monomers, or at least 10 ethylene glycol monomers. In some embodiments of the present disclosure, the PEG component is a branched polymer. In some embodiments of the present disclosure, the PEG component is an unbranched polymer. In some embodiments, the PEG polymer component is functionalized with an amino group or derivative thereof, a carboxyl group or derivative thereof, or both an amino group or derivative thereof and a carboxyl group or derivative thereof.

In some embodiments, the PEG component of a linker of the present disclosure is an amino-tetra-ethylene glycol-carboxyl group or derivative thereof. In some embodiments, the PEG component of a linker of the present disclosure is an amino-tri-ethylene glycol-carboxyl group or derivative thereof. In some embodiments, the PEG component of a linker of the present disclosure is an amino-di-ethylene glycol-carboxyl group or derivative thereof. In some embodiments, an amino derivative is the formation of an amide bond between the amino group and a carboxyl group to which it is conjugated. In some embodiments, a carboxyl derivative is the formation of an amide bond between the carboxyl group and an amino group to which it is conjugated. In some embodiments, a carboxyl derivative is the formation of an ester bond between the carboxyl group and an hydroxyl group to which it is conjugated.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. In some embodiments, the isotope is zirconium.

Those of ordinary skill in the art will recognize that a large variety of possible moieties can be coupled to the resultant activatable antibodies of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Pharmaceutical Compositions

The antibodies, conjugated antibodies, activatable antibodies and/or conjugated activatable antibodies of the disclosure (also referred to herein as "active compounds"), and derivatives, fragments, analogs and homologs thereof, can be incorporated into pharmaceutical compositions suitable for administration. Such compositions typically comprise the antibody, the conjugated antibody, activatable antibody and/or conjugated activatable antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Definitions

Unless otherwise defined, scientific and technical terms used in connection with the present disclosure shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, domain antibody, single chain, Fab, and F(ab')₂ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 µM; in some embodiments, ≤100 nM and in some embodiments, ≤10 nM.

As used herein, the terms "specific binding," "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to the target, when the binding constant ($K_d$) is ≤1 µM, in some embodiments ≤100 nM, in some embodiments ≤10 nM, and in some embodiments ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the disclosure include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Green, Eds., Sinauer Associates, Sunderland, Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present disclosure, providing that the variations in the amino acid sequence maintain at least 75%, in some embodiments, at least 80%, 90%, 95%, and in some embodiments, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative.

Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Suitable amino acid substitutions are those that: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to the target, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

The terms subject and patient are used interchangeably herein.

Antibodies and/or activatable antibodies of the disclosure specifically bind a given target, e.g., a human target protein such as human PDL1. Also included in the disclosure are antibodies and/or activatable antibodies that bind to the same epitope as the antibodies and/or activatable antibodies described herein. Also included in the disclosure are antibodies and/or antibodies activatable antibodies that compete with an anti-PDL1 antibody and/or an anti-PDL1 activatable antibody described herein for binding to PDL1, e.g., human PDL1. Also included in the disclosure are antibodies and/or antibodies activatable antibodies that cross-compete with an anti-PDL1 antibody and/or an anti-PDL1 activatable antibody described herein for binding to PDL1, e.g., human PDL1.

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to the target. If the monoclonal antibody being tested competes with the monoclonal antibody of the disclosure, as shown by a decrease in binding by the monoclonal antibody of the disclosure, then the two monoclonal antibodies bind to the same, or a closely related, epitope. An alternative method for determining whether a monoclonal antibody has the specificity of a monoclonal antibody of the disclosure is to pre-incubate the monoclonal antibody of the disclosure with the target and then add the monoclonal antibody being tested to determine if the monoclonal antibody being tested is inhibited in its ability to bind the target. If the monoclonal antibody being tested is inhibited then, in all likelihood, it has the same, or functionally equivalent, epitopic specificity as the monoclonal antibody of the disclosure.

The invention will be further described in the following examples, which do not limit the scope of the invention described in the claims.

EXAMPLES

Example 1. Assessment of Tolerability of Anti-PDL1 Antibodies in Solid Tumors and Lymphomas This Example evaluates the safety, tolerability, pharmacokinetics (PK), pharmacodynamics (PD), and preliminary antitumor activity of one of more doses, e.g., a single dose or multiple doses, of an anti-PDL1 activatable antibody as a monotherapy or in combination with ipilimumab (also known as Yervoy®), an anti-CTLA-4 antibody, or vemurafenib (also known as Zelboraf®), a B-Raf enzyme inhibitor, in patients with advanced, unresectable solid tumors or lymphoma.

This Example used the anti-PDL1 activatable antibody referred to herein as anti-PDL1 activatable antibody PL07-2001-C5H9v2, which comprises the following heavy and light chain variable region sequences:

```
PL07-2001-C5H9v2 Heavy Chain Variable Sequence
                                   (SEQ ID NO: 46)
EVQLLESGGGLVQPGGSLRLSCAASGFTFSSYAMSWVRQAPGKGLEWVSS

IWRNGIVTVYADSVKGRFTISRDNSKNTLYLQMNSLRAEDTAVYYCAKWS

AAFDYWGQGTLVTVSS

PL07-2001-C5H9v2 Light Chain Variable Sequence
                                   (SEQ ID NO: 137)
QGQSGSGIALCPSHFCQLPQTGGGSSGGSGGSGGISSGLLSGRSDNHGGS

DIQMTQSPSSLSASVGDRVTITCRASQSISSYLNWYQQKPGKAPKLLIYA

ASSLQSGVPSRFSGSGSGTDFTLTISSLQPEDFATYYCQQDNGYPSTFGG

GTKVEIKR
```

Anti-PDL1 activatable antibody PL07-2001-C5H9v2 comprises the following heavy and light chain sequences:

```
PL07-2001-C5H9v2 Heavy Chain Sequence
                                   (SEQ ID NO: 432)
EVQLLESGGGLVQPGGSLRLSCAASGFTFSSYAMSWVRQAPGKGLEWVSS

IWRNGIVTVYADSVKGRFTISRDNSKNTLYLQMNSLRAEDTAVYYCAKWS

AAFDYWGQGTLVTVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMIS

-continued
RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLG

PL07-2001-C5H9v2 Light Chain Sequence
                                   (SEQ ID NO: 428)
QGQSGSGIALCPSHFCQLPQTGGGSSGGSGGSGGISSGLLSGRSDNHGGS

DIQMTQSPSSLSASVGDRVTITCRASQSISSYLNWYQQKPGKAPKLLIYA

ASSLQSGVPSRFSGSGSGTDFTLTISSLQPEDFATYYCQQDNGYPSTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

It is known that tumors can evade host immunity by expression of programmed death ligand 1 (PD-L1), a ligand that negatively regulates programmed cell death 1 (PD-1), an inhibitory receptor expressed on activated T cells (Herbst R S et al., Nature. vol. 515: 563-67 (2014)). Antibodies targeting PD-L1 have shown activity against a variety of cancers and are being tested in combination with other immunotherapies in an effort to improve response rates and durability of response (Iwai Y et al., J Biomed Sci., vol. 24:26 (2017). However, significant, life-threatening immune-related toxicities (irAEs) are known toxicities of antibodies that block the PD1/PDL1 axis, especially when used in a wide variety of combinations with other immunotherapies, including with ipilimumab, (Wolchok J D et al., N Engl J Med., vol. 369:122-33 (2013); Larkin J et al., N Engl J Med., vol. 373:23-34 (2015), vemurafenib, cobimetinib, vemurafenib/cobimetinib, pazopanib, or osimertinib (Ahn M J et al., Expert Opin Drug Saf, vol. 16:465-469 (2017); Hwu P et al., Ann Oncol, vol. 27:379-400 (2016)).

More than 90% of tumor samples from 200 patients with a variety of malignancies demonstrated activation of the PL07-2001-C5H9v2 activatable antibody in in situ studies (see PCT International Publication Number WO/2014/107599, published 10 Jul. 2014, by Vasiljeva O, et al. for representative assay techniques), a finding that corroborates the presence of tumor microenvironment proteases in the overwhelming majority of tumors necessary to ensure activation of the activatable antibody in vivo. In addition, preclinical results have demonstrated equivalent efficacy for a mouse surrogate of the PL07-2001-C5H9v2 activatable antibody compared with the mouse surrogate parental antibody while minimizing induction of systemic autoimmunity in diabetes-susceptible non-obese diabetic mice (Wong C. et al., Presented at CRI-CIMT-EATI-AACR; 16 Sep. 2015; New York, N.Y.). The mouse surrogate of the PL07-2001-C5H9v2 activatable antibody also exhibited reduced peripheral binding to circulating T cells in tumor-bearing mice compared with the parental antibody (Wong C. et al., ibid.).

Figure 1B:
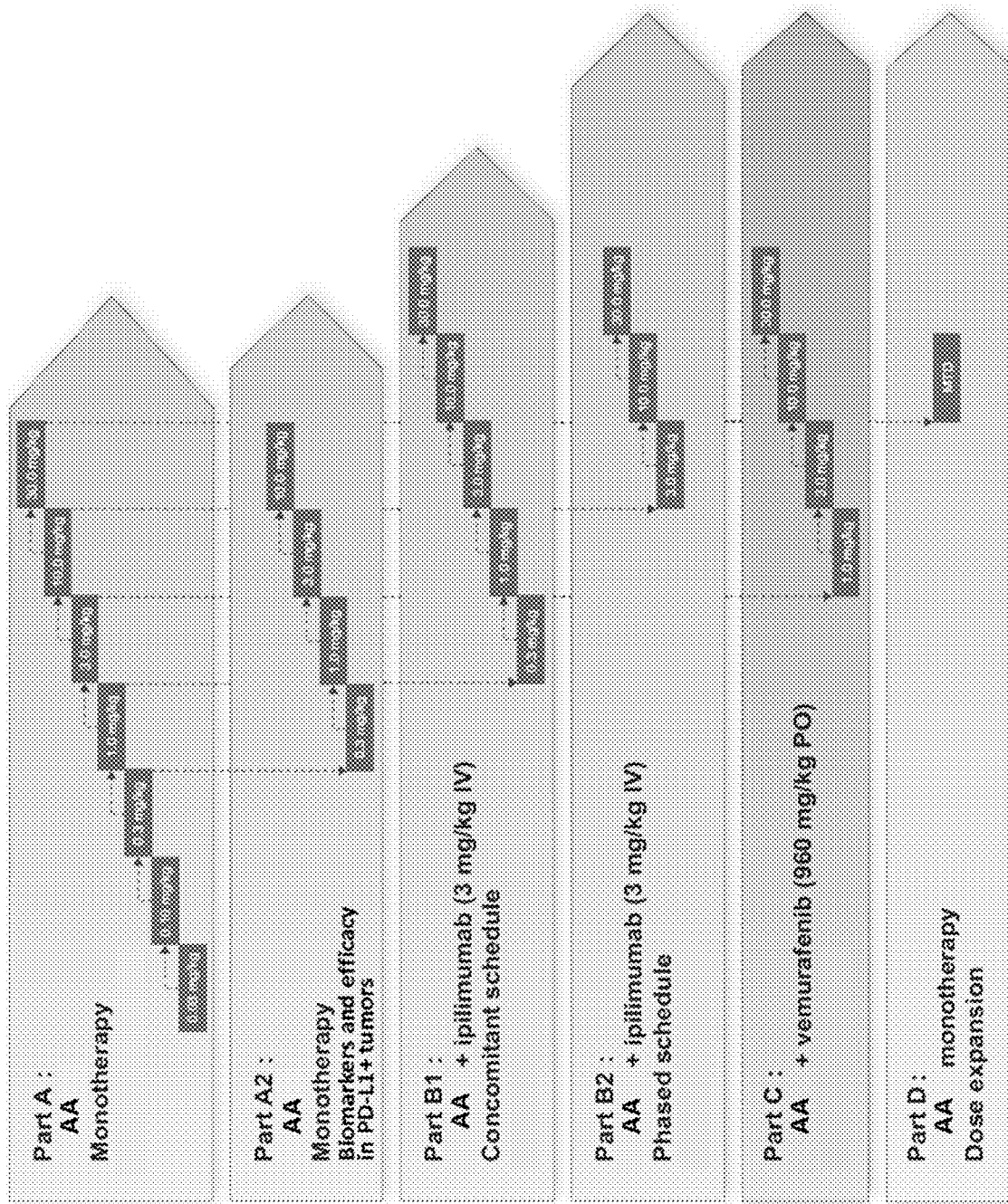
FIG. 1B is a schematic representation of a study design for the study in Example 2, where "AA" represents the anti-PDL1 activatable antibody referred to herein as PL07-2001-05H9v2, which comprises the heavy chain sequence of SEQ ID NO: 432 and the light chain sequence of SEQ ID NO: 428. As compared to FIG. 1A, this schematic representation includes a further optional Part A2 in the study design.

The study described herein is an open-label, multicenter, dose-escalation, phase 1/2 study that is conducted in multiple parts as shown in FIGS. 1A and 1B, where "AA" represents the anti-PDL1 PL07-2001-C5H9v2 activatable antibody.

The study includes dose escalation groups receiving activatable antibodies: monotherapy groups (Part A and A2), one combination therapy with ipilimumab group but two distinct schedules (Parts B1 and B2), one combination therapy with vemurafenib group (Part C), and one monotherapy group in a dose expansion phase (FIG. 1A does not include Part A2; FIG. 1B includes Part A2). Within each part, dose escalation followed a 3+3 design. Not all subjects in the study were necessarily enrolled in Part A2, but for those who are, in some embodiments, the enrollment in Part A2 requires successful completion of the monotherapy dose level in Part A. For those subjects who enroll in Part A2, this Part A2 refines the selection of the MTD/maximum achieved dose by assessing the relationship between dose/exposure with safety and efficacy and with the levels of activated PL07-2001-C5H9v2 in the tumor microenvironment and in plasma in patients with PD-L1+ tumors. Initiation of cohort enrollment in Parts B1, B2, and C requires successful completion of the subsequent monotherapy dose level tested in at least Part A. Enrollment for Part D, the expansion phase, is initiated after dose escalation for Part A is complete and the maximum tolerated dose (MTD) has been determined. Treatment continues for up to 2 years or until disease progression is confirmed or toxicity becomes unacceptable.

In Part A, the PL07-2001-C5H9v2 activatable antibody monotherapy was administered at the indicated dose (i.e., 0.03, 0.1, 0.3, 1, 3, 10, 30 mg/kg) IV every 14 days. For those subjects that enroll in Part A2, Part A2, PL07-2001-C5H9v2 activatable antibody monotherapy is administered at the indicated dose IV every 14 days to study biomarkers and efficacy in PD-L1+ tumors. In Part B1, the concomitant schedule was PL07-2001-C5H9v2 activatable antibody at the indicated dose plus ipilimumab at 3 mg/kg, administered IV every 21 days for 4 doses, followed by PL07-2001-C5H9v2 activatable antibody monotherapy administered IV every 14 days. In Part B2, the phased schedule is PL07-2001-C5H9v2 activatable antibody monotherapy administered IV every 14 days for 4 doses, followed by PL07-2001-C5H9v2 activatable antibody at the indicated dose plus ipilimumab administered IV every 21 days for 4 doses, followed by PL07-2001-C5H9v2 activatable antibody monotherapy administered IV every 14 days. In Part C, PL07-2001-C5H9v2 activatable antibody at the indicated dose was administered IV every 14 days plus vemurafenib at 960 mg/kg PO administered twice daily. In Part D, PL07-2001-C5H9v2 activatable antibody is administered at the MTD (determined from Part A) IV every 14 days. If 30 mg/kg PL07-2001-05H9v2 activatable antibody plus 3 mg/kg ipilimumab is judged to be safe, escalation of PL07-2001-C5H9v2 activatable antibody with 10 mg/kg ipilimumab can be initiated, starting with 10 mg/kg PL07-2001-C5H9v2 activatable antibody and proceeding, as tolerated, to 30 mg/kg PL07-2001-C5H9v2 activatable antibody. If no MTD is established for the combination of 3 mg/kg ipilimumab, the 10 mg/kg and 30 mg/kg dose levels of PL07-2001-C5H9v2 activatable antibody can be evaluated in combination with 10 mg/kg ipilimumab.

In FIGS. 1A and 1B, IV represents intravenous administration, PO represents oral administration, and MTD refers to the maximum tolerated dose level.

The PL07-2001-C5H9v2 activatable antibody in Part A was dosed as follows: a first cohort was administered 0.03 mg/kg, a second cohort was administered 0.10 mg/kg, a third cohort was administered 0.3 mg/kg, a fourth cohort was administered 1.0 mg/kg, a fifth cohort was administered 3.0 mg/kg, a sixth cohort was administered at 10.0 mg/kg, and a seventh cohort was administered at 30.0 mg/kg.

For those subjects that enroll in part A2, the PL07-2001-C5H9v2 activatable antibody in Part A2 is dosed as follows: a first cohort is administered 0.3 mg/kg, a second cohort is administered 1.0 mg/kg, a third cohort is administered 3.0 mg/kg, and a fourth cohort is administered 10.0 mg/kg.

Subjects in Part B1 were dosed as follows: ipilimumab is administered 3 mg/kg IV and the PL07-2001-C5H9v2 activatable antibody was dosed such that a first cohort was administered 0.3 mg/kg, a second cohort was administered at 1.0 mg/kg, a third cohort was administered at 3.0 mg/kg, a fourth cohort was administered at 10.0 mg/kg, and a fifth cohort is administered at 30.0 mg/kg.

Subjects in Part B2 are dosed as follows: ipilimumab is administered 3 mg/kg IV and the PL07-2001-C5H9v2 activatable antibody is dosed such that a first cohort is administered at 3.0 mg/kg, a second cohort is administered at 10.0 mg/kg, and a third cohort is administered at 30.0 mg/kg, a fourth cohort is administered at 10.0 mg/kg, and a fifth cohort is administered at 30.0 mg/kg.

Subjects in Part C are dosed as follows: vermurafenib is delivered 960 mg/kg PO and PL07-2001-C5H9v2 activatable antibody is dosed such that a first cohort is administered 1.0 mg/kg, a second cohort is administered at 3.0 mg/kg, and a third cohort is administered at 10.0 mg/kg, and a fourth cohort is administered 30.0 mg/kg.

Subjects in Part D are dosed as follows: the PL07-2001-C5H9v2 activatable antibody is administered at the MTD.

Within each part of the study, dose escalation of the administered anti-PDL1 activatable antibody follows a 3+3 design, which is a rule-based design in which the lowest dose level is allocated to the first cohort, the dose is adaptively escalated or de-escalated based on observed dose-limiting toxicities (DLTs), and the adaptive escalation or de-escalation is repeated until the maximum tolerated dose (MTD) is achieved. In Part A, one subject each is enrolled in the 0.03, 0.1, and 0.3 mg/kg dosing cohorts, and subsequent dose levels will follow the 3+3 design.

In this study, enrollment in Part A2 as depicted in FIG. 1B requires successful completion of the monotherapy dose level in Part A. Part A2 will enroll at least an additional six patients with PD-L1+ cancer at each indicated dose, including a minimum of 2 subjects per cohort with thymoma, thymic carcinoma, or a thymic epithelial tumor. Part A2 will refine the MTD/maximum achieved dose (MAD), to evaluate the relationship between dose/exposure and safety, efficacy and pharmacodynamics biomarkers, and the levels of activated antibody in the tumor microenvironment and in plasma.

In this study, initiation of cohort enrollment in Parts B1, B2, and C of FIG. 1A or 1B requires successful completion of the subsequent monotherapy dose level tested in at least Part A. Enrollment for Part D is initiated after dose escalation is complete for Part A and the maximum tolerated dose has been determined. Treatment is continued for up to 2 years or until confirmed disease progression or unacceptable toxicity.

In this study when Part A2 is included, up to 175 patients are enrolled in the dose escalation cohorts (1-6 patients per dose cohort in Part A, approximately 6 patients per dose cohort in Part A2, and 3-6 patients per dose cohort in Parts B1, B2, and C). Approximately 20 patients are enrolled for the dose expansion cohort (Part D). If Part A2 is not included, up to 150 patients are enrolled as set forth immediately above, omitting Part A2. The key eligibility criteria for enrolled patients is shown in the Table A below.

TABLE A

| | Key eligibility criteria. |
|---|---|
| All parts | Age ≥18 years<br>ECOG performance status 0-1 |
| Part A | Advanced, unresectable solid tumor or lymphoma with no further standard of care available<br>Immunotherapy naïve (including PD-1/PD-L1 and CTLA-4 inhibitor therapy)<br>Immunotherapy unavailable for patient's disease |
| Part A2 (Optional) | Same requirements as for Part A, and must be PD-L1+ (tumor proportion score at least 1% membranous staining)<br>Must agree to participate in biomarker analysis and have a tumor site that is safe to biopsy |
| Part B1 | Advanced, unresectable solid tumor or lymphoma with no further standard of care available<br>Immunotherapy naïve<br>Immunotherapy unavailable for patient's disease |
| Part B2 | Advanced, unresectable solid tumor or lymphoma with no further standard of care available<br>Previously treated with a PD-1/PD-L1 inhibitor (discontinued for reasons other than toxicity) |
| Part C | CTLA-4 inhibitor-naïve<br>Advanced, unresectable melanoma<br>BRAF$^{V600E}$ mutation positive<br>BRAF inhibitor-naïve<br>PD-1/PD-L1 inhibitor-naïve and/or immunotherapy naïve<br>Immunotherapy naïve<br>Immunotherapy unavailable for patient's disease |
| Part D | Advanced, unresectable PDL1-responsive tumor types<br>Measurable disease<br>PD-L1 positive or unknown status (not known to be PD-L1 negative)<br>Immunotherapy naïve<br>Immunotherapy unavailable for patient's disease |
| Exclusion Criteria that may apply in certain embodiments | Prior therapy with a chimeric antigen receptor (CAR) T-cell containing regimen.<br>History of severe allergic or anaphylactic reactions to human monoclonal antibody therapy or known hypersensitivity to any Probody therapeutic.<br>Active or history of uveal, mucosal, or ocular melanoma. Human immunodeficiency virus (HIV) or acquired immune deficiency syndrome (AIDS)-related illness, chronic hepatitis B or C.<br>History of or current active autoimmune diseases, including but not limited to inflammatory bowel diseases, rheumatoid arthritis, autoimmune thyroiditis, autoimmune hepatitis, systemic sclerosis, systemic lupus erythematosus, autoimmune vasculitis, autoimmune neuropathies, or type 1 insulin dependent diabetes mellitus.<br>History of syndrome or medical condition(s) that requires systemic steroids (>10 mg daily prednisone equivalents) or immunosuppressive medications.<br>History of allogeneic tissue/solid organ transplant, prior stem cell or bone marrow transplant.<br>Chemotherapy, biochemotherapy, radiation or immunotherapy or any investigational treatment within 30 days prior to receiving any study drug.<br>Major surgery (requiring general anesthesia) within 3 months or minor surgery (excluding biopsies conducted with local/topical anesthesia) or gamma knife treatment within 14 days (with adequate healing) of administration of any study drug. |

Abbreviations:
CTLA-4, cytotoxic T-lymphocyte-associated antigen 4;
ECOG, Eastern Cooperative Oncology Group;
PD-1, programmed death 1 receptor;
PD-L1, programmed death ligand 1.
In some embodiments, as a cohort assignment occurs, patients with known PD-L1 status are assigned to Part A, but PD-L1 status is not an inclusion/exclusion criterion.

The primary endpoints for this study are: (i) safety and tolerability of the PL07-2001-C5H9v2 activatable antibody alone or in combination with ipilimumab or vemurafenib, and/or (ii) maximum tolerated dose and dose-limiting toxicities of the PL07-2001-C5H9v2 activatable antibody alone or in combination with ipilimumab or vemurafenib.

Secondary endpoints of this study can include any of the following, or any combination thereof: objective response according to Response Evaluation Criteria in Solid Tumors version 1.1 (RECIST v 1.1), immune-related RECIST, or modified Cheson/Lugano Classification for lymphomas; time to response; duration of response; progression-free survival; incidence of anti-drug antibodies; single and multiple dose pharmacokinetic profile of the PL07-2001-C5H9v2 activatable antibody alone, and of PL07-2001-

C5H9v2 activatable antibody in combination with ipilimumab, or vemurafenib; and/or overall survival.

Additional endpoints/objectives of this study can include any one or more of the following, or any combination thereof: potential predictive markers of PL07-2001-C5H9v2 activatable antibody activity; protease activity and degree of PL07-2001-C5H9v2 activatable antibody cleavage in tumor and peripheral blood; and/or immunomodulatory activity of PL07-2001-C5H9v2 activatable antibody in on-treatment biopsies.

The following assessments are exemplary and not intended to be limiting. They are performed, in some embodiments, at each study visit: adverse events, physical examination, vital signs, hematology, serum chemistry, B symptoms (lymphoma patients), Eastern Cooperative Oncology Group (ECOG) performance status, and concomitant medications. Imaging for tumor response assessment are performed every 8 weeks for the first 12 months, then every 12 weeks thereafter. Blood samples for pharmacokinetic, pharmacodynamic, and biomarker analyses are obtained at pre-specified time points. After the last dose of study medication, patients are evaluated every 3 months for disease progression and overall survival until study withdrawal or death. In some embodiments, biopsies are collected. In some embodiments, archival tissue or fresh biopsy samples are provided at baseline. In some embodiments, patients in Part A2 undergo at least one on-treatment tumor biopsy. In some embodiments, patients in Part B2 undergo at least one on-treatment tumor biopsy. In some embodiments, these patients have measurable disease.

Several translational strategies/methods are used to investigate for example, presence of activatable antibody-activating protease activity, activatable antibody activation, e.g., protease-dependent activatable antibody activation, presence of target (PDL1), target engagement, PDL1 inhibition or other PD-1 pathway inhibition, immune response pattern in the tumor, and other biological effects. Such strategies/methods can include any one or more of the following, or any combination thereof: (a) activatable antibody activation in, for example, biopsies or blood samples, e.g., plasma, using, for example, (i) a WES assay, which comprises capillary electrophoresis with immunodetection; see, e.g., ProteinSimple's Simple Western WES brochure, and/or (ii) an assay that detects protease activation of activatable antibodies, such as one of the assays disclosed in WO/2014/107599, ibid.; (b) pharmacodynamic biomarker assessment by, for example, (i) NANOSTRING gene expression panel of, e.g., a biopsy, (ii) IHC, e.g., of a biopsy, to detect immune cell infiltration, and/or (iii) LUMINEX cytokine panel evaluation of, e.g., plasma; and/or (c) PD-L1 expression assessment of, e.g., a biopsy, by, e.g., IHC. In some embodiments, immunoPET imaging will be used.

Figure 2:
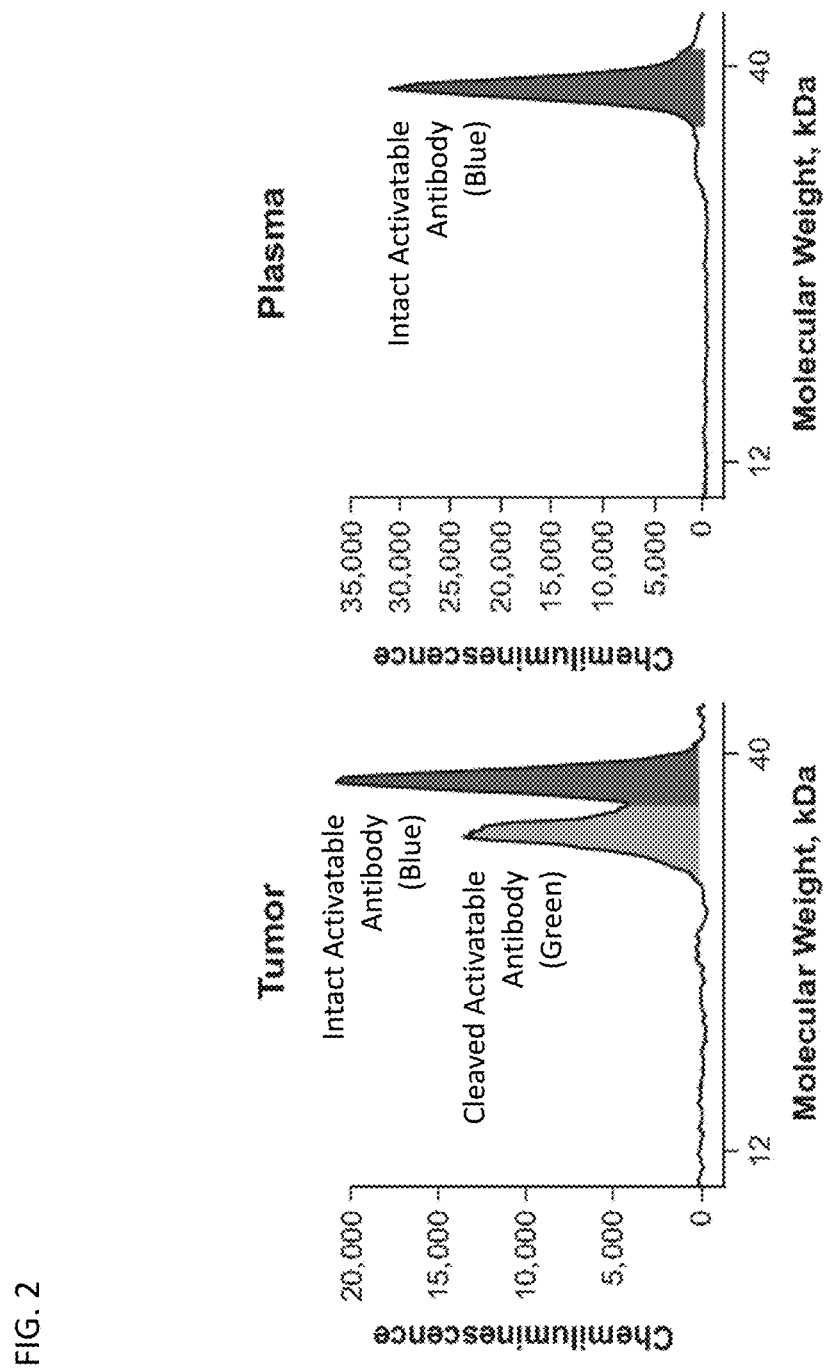
FIG. 2 shows a series of graphs depicting detection of cleaved and intact anti-PD-L1 activatable antibodies in tumor and plasma samples determined using the WES system (ProteinSimple, San Jose, Calif.) under conditions similar to those described in the WES instrumentation manual.

An example of a WES assay comparing the amount of cleaved and intact PL07-2001-C5H9v2 activatable antibody in preclinical tumor and plasma samples is shown in FIG. 2.

In the above-described dose-escalation segment of the trial, the pharmacokinetics (PK) in patients receiving a single dose of PL07-2001-C5H9v2 monotherapy was assessed. The PK samples were collected intensively following the first dose of PL07-2001-C5H9v2, with sparse collection thereafter. Analytes quantified in plasma samples were intact (uncleaved) activatable antibody (i.e., the prodrug form), and the total sum of prodrug/intact and cleaved forms of PL07-2001-C5H9v2 (representing the sum of intact and activated species). Preliminary single-dose PK data was collected for patients enrolled in the dose-escalation segment of the above-described studies receiving a single dose of 0.03-30.0 mg/kg PL07-2001-C5H9v2 as a single agent.

Figure 8A:
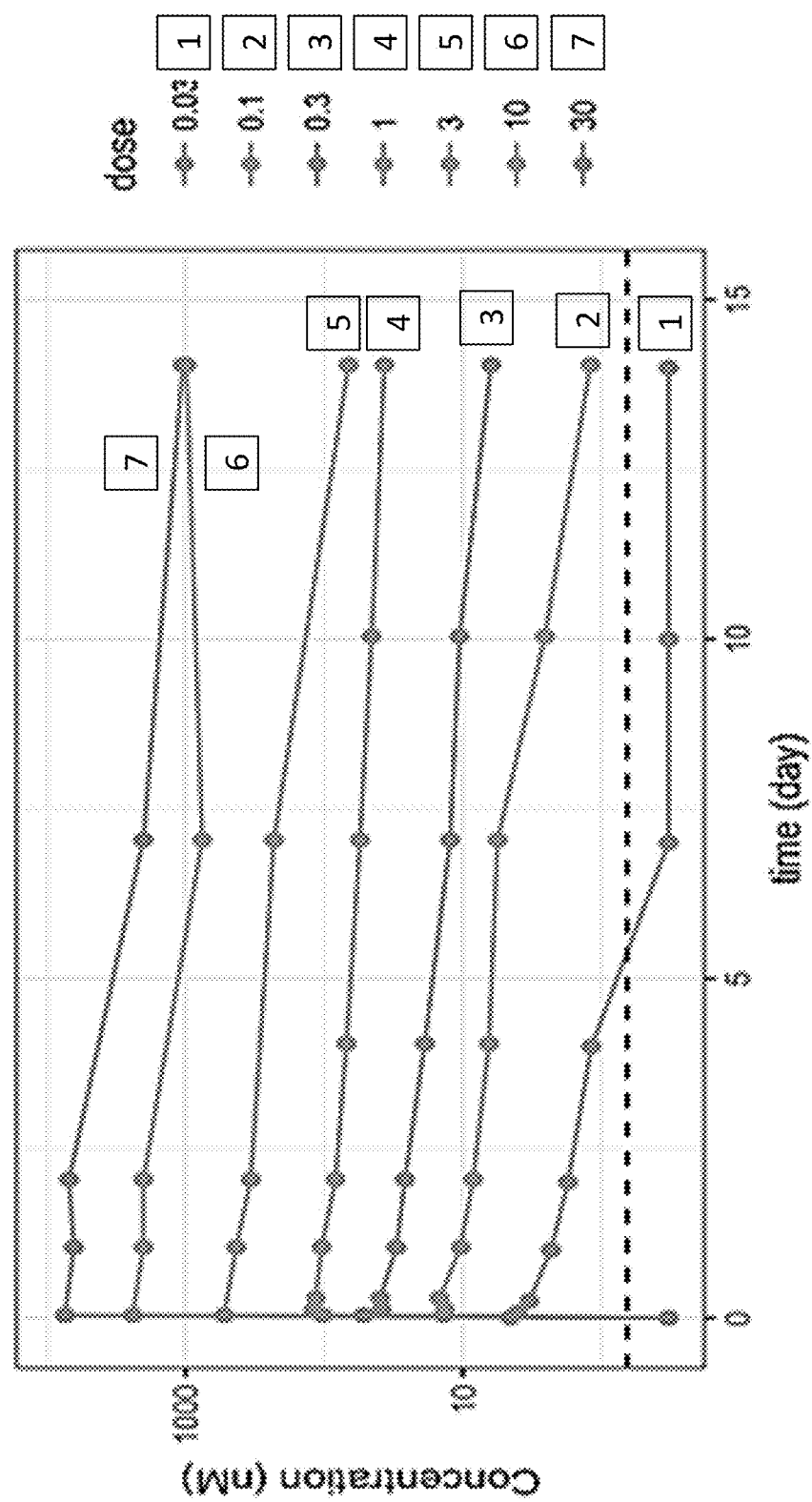
FIGS. 8A and 8B are graphs of median plasma concentration of intact (uncleaved) and total (i.e., intact and cleaved) PL07-2001-C5H9v2 (nM), respectively, versus time (day) following administration of up to 30 mg/Kg q2W to Cohorts A and A2 Cycle 1 Dose 1. The dashed line represents the limit of quantitation (LLOOQ) for the assay, and in this representation, only below LOQ (BLOQ) data are assigned a value of LOQ/2.
Figure 8B:
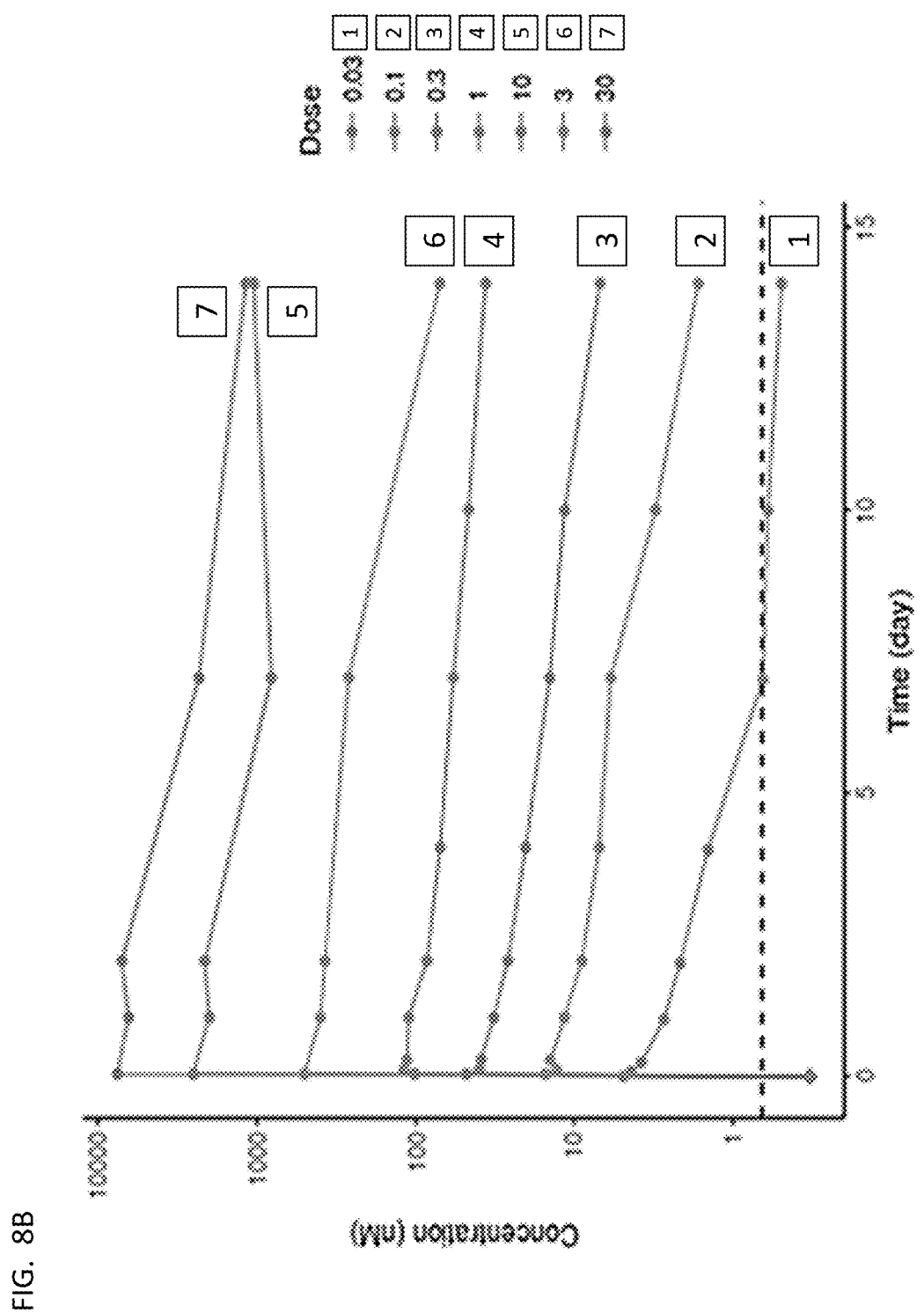

Both intact and total (intact plus activated) PL07-2001-C5H9v2 concentrations were determined in plasma samples using a validated high performance liquid chromatography tandem mass spectrometry (HPLC MS/MS) method with a lower limit of quantification for each analyte of 0.657 nM. Magnetic beads coated with protein A were used to enrich for immunoglobulin (including intact and activated PL07-2001-C5H9v2) in $K_2EDTA$ plasma samples. The bound proteins were digested with trypsin, and two peptide fragments unique to PL07-2001-C5H9v2 were monitored: one peptide from the heavy chain that is present in both the intact and activated forms of PL07-2001-C5H9v2 (for quantitation of total PL07-2001-05H9v2) and one peptide that is present in the intact (activatable form) of PL07-2001-C5H9v2 but not in the activated form of PL07-2001-C5H9v2 (for quantitation of intact PL07-2001-05H9v2). Following the immunocapture and digestion steps, the final extract was analyzed via HPLC with MS/MS detection using positive ion electrospray. The results are shown in FIGS. 8A and 8B, which show the median plasma concentration of intact PL07-2001-05H9v2 (nM) (FIG. 8A) and total PL07-2001-C5H9v2 (i.e., intact and activated (nM), FIG. 8B), respectively, versus time (day) following administration of up to 30 mg/kg q2w for cohorts A and A2 Cycle 1 Dose 1.

Preliminary single-dose PK data suggests that PL07-2001-C5H9v2 circulates predominantly as the intact, prodrug species. There does not appear to be monotonic trending of the estimates of clearance and the volume of distribution across the 0.1 to 30 mg/kg dose levels. A mechanistic PK model suggests target-mediated drug disposition (TMDD) may not be an important contributor to the clearance of intact, protected PL07-2001-C5H9v2 across the dose range evaluated.

With respect to the evaluation of PL07-2001-C5H9v2 as a monotherapy in a dose escalation cohort in patients with advanced, heavily pretreated solid tumors, eligible patients include those who are PD-1, PD-L1, and CTLA-4 inhibitor naïve with immunotherapy (IMT) unavailable as a standard of care for their disease. PL07-2001-C5H9v2 was given every 14 days in cohorts of doses in the range of from 0.03 to 30 mg/kg IV. Twenty two patients with a median age of 65 years (range, 32-81) were enrolled having a median of 3 prior anticancer treatments (range of 1-13).

The following preliminary results were observed: 1 dose-limiting toxicity (DLT) was observed (Grade 3 febrile neutropenia; 3 mg/kg); the maximum tolerated dose (MTD) was not reached. Grade 3-4 treatment-related events were observed in 2 patients, respectively: febrile neutropenia/thrombocytonpenia (3 mg/kg) and elevated AST/ALT (30 mg/kg). Across all dose levels, the best response based on change in target lesions from baseline in 17 evaluable patients included 2 PR (thymoma and PD-L1 negative TNBC), 11 SD, and 4 PD. 7/17 (41%) evaluable patients had target lesions decrease from baseline as per RECIST v1.1. At dose levels ≥3 mg/kg, 5/8 subjects (63%) had target lesions decrease from baseline. Thus, the preliminary data suggests that PL07-2001-C5H9v2 in heavily pretreated patients with IMT-naïve solid tumors where checkpoint blockade is unavailable as SOC for their disease show a manageable safety profile with signals of antitumor activity.

After approximately four months, a further data cut was made after the above results were obtained. As of the date of the later data cutoff, Part A had enrolled 22 patients, including 2 patients still receiving treatment. Twenty patients discontinued treatment for the following reasons: radiological or clinical disease progression (n=16), voluntary withdrawal (n=2), or adverse event (n=2). The subjects had any one of a number of different cancer types, including, for example, uterine carcinoma, esophageal carcinoma, pancreatic carcinoma, castration resistant prostate carcinoma, rectal carcinoma, thymoma or thymic cancers, and triple negative breast cancer. The baseline characteristics for patients treated with PL07-2001-05H9v2 are provided in Table 3

TABLE 3

| Baseline Characteristics for Patients Treated with PL07-2001-C5H9v2 | |
|---|---|
| | All Patients N = 22 |
| Median age, years (range) | 65 (32-81) |
| Sex, n (%) | |
| Female | 13 (59.1) |
| Male | 9 (40.9) |
| Race, n (%) | |
| White | 18 (81.8) |
| African American | 1 (4.5) |
| Not reported/unknown/other | 3 (13.6) |
| Eastern Cooperative Oncology Group (ECOG) performance status score, n (%) | |
| 0 | 9 (40.9) |
| 1 | 13 (59.1) |
| No. of previous cancer treatments, median (range) | 3 (1-13) |

TABLE 3-continued

| Baseline Characteristics for Patients Treated with PL07-2001-C5H9v2 | |
|---|---|
| | All Patients N = 22 |
| Cancer type,[a] n (%) | |
| Uterine carcinoma | 3 (13.6) |
| Esophageal carcinoma | 2 (9.1) |
| Pancreatic carcinoma | 2 (9.1) |
| Castration-resistant prostate cancer | 2 (9.1) |
| Rectal carcinoma | 2 (9.1) |
| Thymoma or thymic cancers | 2 (9.1) |
| Triple-negative breast cancer | 2 (9.1) |
| Other[a] | 7 (31.8) |
| PD-L1 expression status,[b] n (%) | |
| None (<1%) | 10 (45.5) |
| Low (1-49%) | 7 (31.8) |
| High (≥50%) | 2 (9.1) |
| Unknown | 3 (13.6) |

[a]One patient each had breast (estrogen receptor positive (ER+)) carcinoma, cervical carcinoma, colon carcinoma, peritoneal carcinoma, salivary gland carcinoma, head and neck squamous cell carcinoma, and uterine sarcoma.
[b]Assessed with clone 22c3 (Dako PDL-1 IHC 22c3 pharmDx) using archival tissue
[c]Includes 1 patient with incomplete response/nonprogressive disease who did not have measurable disease at baseline.

The mean (range) durations of treatment are provided in Table 4.

TABLE 4

| | Duration of PL07-2001-C5H9v2 Treatment | | | | | | | |
|---|---|---|---|---|---|---|---|---|
| | PL07-2001-C5H9v2 Dose, mg/kg | | | | | | | |
| | 0.03 n = 2 | 0.1 n = 2 | 0.3 n = 2 | 1.0 n = 3 | 3.0 n = 7 | 10.0 n = 3 | 30.0 n = 3 | All Patients N = 22 |
| Treatment duration, mean (range), months | 5.6 (4-7) | 3.5 (1-6) | 1.8 (2-2) | 4.4 (4-6) | 2.5 (0-9) | 5.9 (2-8) | 2.5 (2-4) | 3.5 (0-9) |

Pharmacokinetic Analysis

Preliminary single-agent, single-dose PL07-2001-C5H9v2 pharmacokinetic data suggest that PL07-2001-C5H9v2: (a) circulates predominantly as the intact prodrug species (96% intact at 30 mg/kg); and (b) is likely only minimally influenced by target-mediated drug disposition at low doses. By comparison, the PD-L1 inhibitor atezolizumab appears to exhibit nonlinear PK below the 1 mg/kg dose level. See, R. S. Herbst, et al., "Predictive correlates of response to the anti-PD-L1 antibody MPDL3280A in cancer patients," Nature (2014 Nov. 27) 515(7528): 563-567Tumor response rates among evaluable patients (n=20) are provided in Table 5

TABLE 5

| | Best Tumor Response in Evaluable Patients[a] per RECIST[1] v1.1, n(%) | | | | | | | |
|---|---|---|---|---|---|---|---|---|
| | PL07-2001-C5H9v2 Dose, mg/kg | | | | | | | |
| | 0.03 n = 2 | 0.1 n = 2 | 0.3 n = 2 | 1.0 n = 3 | 3.0 n = 5 | 10.0 n = 3 | 30.0 n = 3 | All Evaluable Patients N = 20 |
| | Best overall response, n (%) | | | | | | | |
| Partial response[b] | 0 | 0 | 0 | 0 | 1 (20.0) | 2 (66.7) | 0 | 3 (15.0) |
| Stable disease | 1 (50.0) | 1 (50.0) | 1 (50.0) | 1 (33.3) | 2 (40.0)[c] | 0 | 2 (66.7) | 8 (40.0) |

TABLE 5-continued

Best Tumor Response in Evaluable Patients[a] per RECIST[1] v1.1, n(%)

PL07-2001-C5H9v2 Dose, mg/kg

| | 0.03<br>n = 2 | 0.1<br>n = 2 | 0.3<br>n = 2 | 1.0<br>n = 3 | 3.0<br>n = 5 | 10.0<br>n = 3 | 30.0<br>n = 3 | All Evaluable<br>Patients<br>N = 20 |
|---|---|---|---|---|---|---|---|---|
| | | | Best overall response, n (%) | | | | | |
| Progressive disease | 1 (50.0) | 1 (50.0) | 1 (50.0) | 2 (66.7) | 1 (20.0) | 1 (33.3) | 0 | 7 (35.0) |
| Not evaluable | 0 | 0 | 0 | 0 | 1 (20.0) | 0 | 1 (33.3) | 2 (10.0) |

[1]RECIST: Response Evaluation Criteria in Solid Tumors.
[a]Evaluable patients are those with an adequate disease assessment at baseline and ≥1 postbaseline tumor assessment.
[b]Includes 2 patients with unconfirmed partial response.
[c]Includes 1 patient with incomplete response/nonprogressive disease who did not have measurable disease at baseline.

Figure 9A:
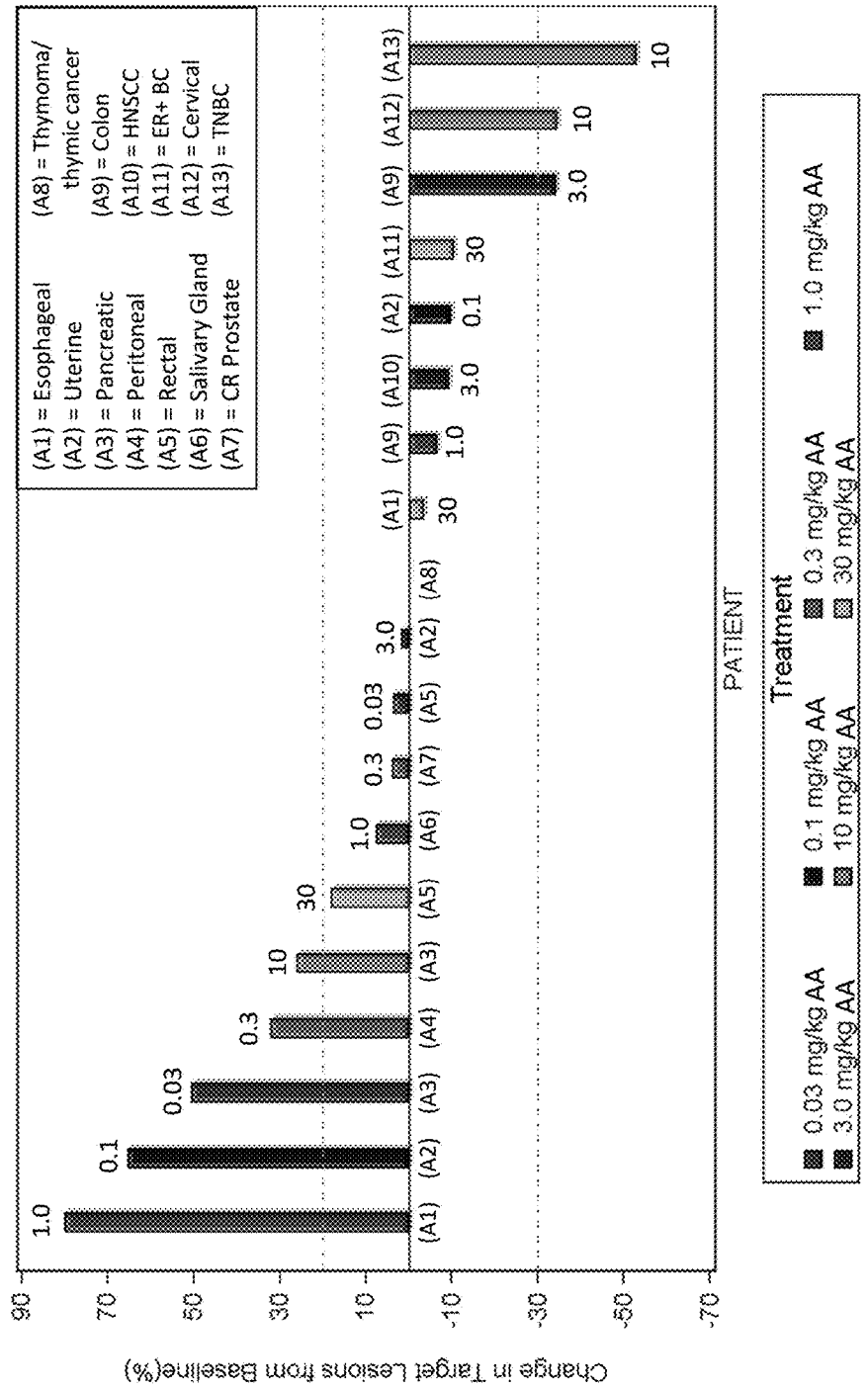
FIG. 9A depicts the best percentage change from baseline in target lesions after administration of PL07-2001-C5H9v2.
Figure 9B:
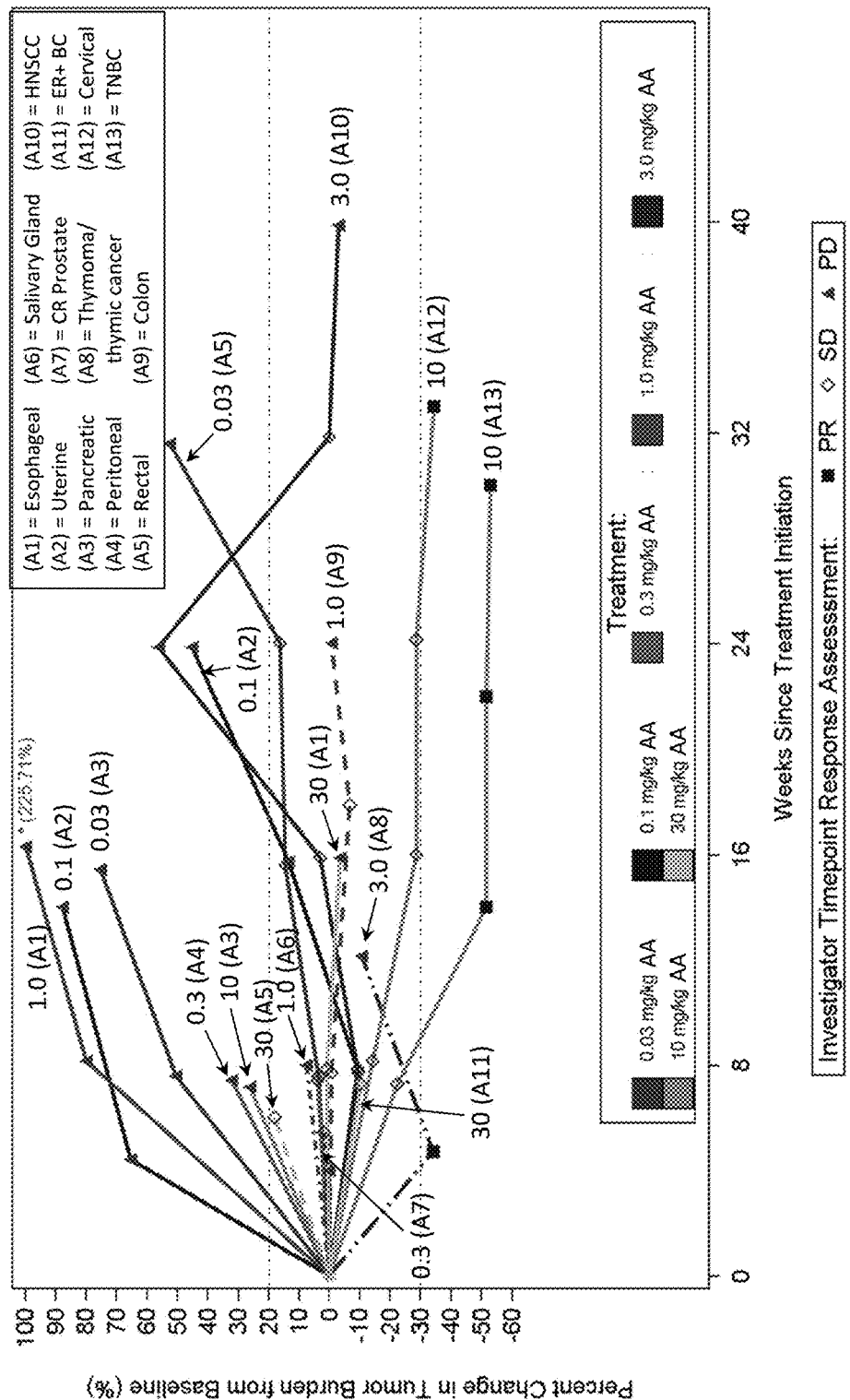
FIG. 9B is a spider plot depicting the change in target lesion (%) vs. time after administration of PL07-2001-C5H9v2. Abbreviations: CR, castration-resistant; ER+BC, estrogen receptor-positive breast cancer; HNSCC, head and neck squamous cell carcinoma; PD, progressive disease; PR, partial response; RECIST, Response Evaluation Criteria in Solid Tumors; SD, stable disease; TNBC, triple-negative breast cancer.

Escalation to 30 mg/kg was completed and maximum tolerated dose (MTD) was not reached. Target lesions decreased from baseline in 8 of 19 patients (42%) with measurable disease at baseline, as shown in FIG. 9A. Target lesions decreased from baseline at dose levels ≥3 mg/kg in 6 of 10 patients (60%). The percentage change in tumor burden over time is presented in FIG. 9B.

Sample Case Studies

Patient A has thymic cancer with high baseline PD-L1 expression and received treatment with PL07-2001-C5H9v2 at a dose of 3 mg/kg. The patient experienced a response to treatment after 2 weeks and had a 48% reduction in mediastinal mass. The patient discontinued treatment because of neutropenia.

Patient B has triple-negative breast cancer with microsatellite-stable low tumor mutation burden (4 mutations/megabase) and negative PD-L1 and received treatment with PL07-2001-C5H9v2 at a dose of 10 mg/kg. Follow-up staging revealed a confirmed partial response. The results are shown in Table 6.

TABLE 6

| Node | Screening<br>Aug. 14, 2017 | C2D56<br>Dec. 5, 2017 | C4D56<br>Mar. 27, 2018 |
|---|---|---|---|
| Right axillary | 30 mm | 12 mm | 9 mm |
| Precarinal lymph | 17 mm | 9 mm | 6 mm |
| Subcutaneous | 25 mm | 14 mm | 19 mm |

Biomarker analysis of tumor biopsy pairs from Patient C (esophogeal cancer; PL07-2001-C5H9v2, 30 mg/kg) demonstrated a 3-fold increase in CD8+ T-cell infiltration after 4 weeks of treatment.

Conclusions

MTD was not determined with doses up to 30 mg/kg. PL07-2001-C5H9v2 is activated in vivo and exerts biological activity as evidenced by: (a) 3 objective responses in 20 evaluable patients (15%), including those with negative PD-L1 expression; (b) a 3-fold increase in CD8+ T-cell infiltration after 4 weeks of treatment. PL07-2001-C5H9v2 exhibited reduced binding in peripheral issue, as suggested by predominant circulation as the intact prodrug species (96% intact at 30 mg/kg); and a favorable safety profile, with only 2 patients experiencing a grade 3 treatment-related AE.

The primary objectives of Part B1 of the study are to assess the safety and tolerability and to determine the maximum tolerated dose (MTD) and the dose-limiting toxicity (DLT) of PL07-2001-C5H9v2 when administered in a concomitant combination schedule with ipilimumab. Secondary objectives are to obtain preliminary evidence of anticancer activity in patients treated with PL07-001-C5H9v2 combined with ipilimumab using response rate (Response Evaluation Criteria in Solid Tumors (RECIST) v 1.1, time to response and duration of response, and progression-free survival. Patients are ≥18 years of age with Eastern Cooperative Oncology Group performance status 0-1. To be included in Part B1, patients (n≤42) are required: (a) to have any metastatic or advanced unresectable solid tumor or lymphoma (excluding thymic epithelial tumor, thymoma, or thymic carcinoma) (measurable or nonmeasurable disease): and (b) to be naïve to immunotherapy, including to PD-1/PD-L1 and CTLA-4 inhibitor therapy, and to have a tumor type not approved for immune checkpoint inhibitors. PL07-2001-C5H9v2 (0.3, 1.0, 3.0, and 10 mg/kg) in combination with ipilimumab (3.0 mg/kg or 10 mg/kg for the highest PL07-2001-C5H9v2 dose level) is administered intravenously every 21 days for 4 cycles, followed by PL07-2001-C5H9v2 monotherapy every 14 days.

Patients with advanced solid tumors received PL07-2001-C5H9v2+ipilimumab in a concomitant schedule (study Part B1). Eligible patients were PD-1, PD-L1, and CTLA-4 inhibitor naïve. Imaging for tumor response assessment is performed every 8 weeks for the first 12 months, then every 12 weeks thereafter. After the last dose of study medication, patients will be evaluated every 3 months for disease progression and overall survival until study withdrawal or death. Archival tissue or fresh biopsy samples are provided at baseline. Serial blood samples for pharmacokinetic (PK) analysis are collected to characterize the PK profile of PL07-2001-C5H9v2, in combination with ipilimumab. Participating patients provide serial blood samples for measurement of exploratory biomarkers of immune modulation.

Planned doses: PL07-2001-C5H9v2 0.3-30 mg/kg intravenously (IV) every 21 days+ipilimumab 3 mg/kg or 10 mg/kg IV every 21 days for 4 cycles, followed by PL07-2001-C5H9v2 monotherapy every 14 days. In preliminary results, Part B1 enrolled 9 patients. Median age was 44 years (range, 28-70); 6 patients (67%) were male. Median number of prior anti-cancer treatments was 4 (range, 2-18). At the time of data cut, 6 patients remained on treatment. Median number of doses of PL07-2001-C5H9v2 (0.3 and 1 mg/kg) and ipilimumab (3 mg/kg) was 2 (range, 2-10) and 2 (range, 2-4), respectively. 1 DLT (grade 3 dyspnea, 0.3 mg/kg PL07-2001-C5H9v2+3 mg/kg ipilimumab) was observed. MTD has not been reached and dose escalation continues. Grade 1-2 treatment-related adverse events (TRAEs) occurred in 6 patients (67%). Four grade 3 TRAEs were experienced by 2 patients (22%) and included colitis, pneumonitis, and AST and ALT increases (0.3 mg/kg PL07-2001-C5H9v2)+3 mg/kg ipilimumab). At the data cutoff date, 1 of 4 evaluable patients showed target lesion reduction of 31% from baseline (0.3 mg/kg PL07-2001-C5H9v2, anal SCC, MSI stable, and intermediate tumor mutation burden). A few days later, this patient had a confirmed PR with 56% reduction in target lesion. Preliminary data suggests that PL07-2001-C5H9v2+ ipilimumab shows a manageable safety profile and signals of antitumor activity.

A further data cut was made after the above preliminary results were obtained. At this later data cut, N=16 individuals received the following doses of PL07-2001-C5H9v2+ ipilimumab, 3.0 mg/kg. 0.3, n=6, 1.0, n=3, 3.0, n=3, 10, n=4. The baseline characteristics are present in Table 7.

TABLE 7

Baseline Characteristics

| | All Patients N = 16 |
|---|---|
| Median age, years (range) | 60 (28-70) |
| Sex, n (%) | |
| Male | 8 (50.0) |
| Female | 8 (50.0) |
| Race, n (%) | |
| White | 12 (81.3) |
| Asian | 1 (6.3) |
| Not reported/unknown/other | 2 (12.5) |
| ECOG performance status, n (%) | |
| 0 | 6 (37.5) |
| 1 | 10 (62.5) |
| No. of previous cancer treatment, median (range) | 3 (1-12) |
| Cancer types,[a] n (%) | |
| Pancreatic carcinoma | 2 (12.5) |
| Other[a] | 14 (87.5) |

[a]One patient each had anal squamous cell carcinoma, breast (ER+) carcinoma, cervix carcinoma, colon carcinoma, gastric cancer, glioblastoma, osteosarcoma, salivary gland carcinoma, cancer of unknown primary origin (CUP), small cell lung cancer, small cell neuroendocrine prostate cancer, testicular carcinoma, triple-negative breast cancer, and head and nene ck squamous cell carcinoma.

At the time of analysis, 4 patients (25.0%) were still receiving treatment. 12 patients discontinued treatment because of disease progression (n=8), symptomatic deterioration (n=3), or death n=1)

The mean (range) durations of treatment are provided in Table 8.

TABLE 8

Duration of PL07-2001-C5H9v2.

| | PL07-2001-C5H9v2 (mg/kg) + Ipilimumab 3.0 mg/kg Dose | | | | |
|---|---|---|---|---|---|
| | 0.3 n = 6 | 1.0 n = 3 | 3.0 n = 3 | 10.0 n = 4 | All Patients N = 16 |
| Time on Treatment, mean (range), months | 3.0 (1-10) | 4.6 (3-6) | 3.4 (1-4) | 1.8 (1-3) | 3.1 (1-10) |

Tumor Response

The best tumor responses are set forth in Table 9.

TABLE 99

Best Tumor Response in Evaluable Patients[a] per RECIST v1.1, n (%)

| | PL07-2001-C5H9v2 (mg/kg) + Ipilimumab (mg/kg) Dose | | | | |
|---|---|---|---|---|---|
| | 0.3 + 3.0 n = 5 | 1.0 + 3.0 n = 3 | 3.0 + 3.0 n = 2 | 10.0 + 3.0 n = 2 | All Evaluable Patients N = 12 |
| Objective response rate[b] | 1 (20.0) | 1 (33.3) | 1 (50.0) | 0 | 3 (25.0) |
| Complete response | 1 (20.0) | 0 | 0 | 0 | 1 (8.3) |
| Partial response | 0 | 1 (33.3) | 1 (50.0) | 0 | 2 (16.7) |
| Stable disease | 0 | 1 (33.3) | 0 | 0 | 1 (8.3) |
| Progressive disease | 4 (80.0) | 1 (33.3) | 1 (50.0) | 2 (100.0) | 8 (66.7) |

[a]Evaluable patients are those with an adequate disease assessment at baseline and ≥1 postbaseline tumor assessment.
[b]Includes patients with unconfirmed response.

Figure 10A:
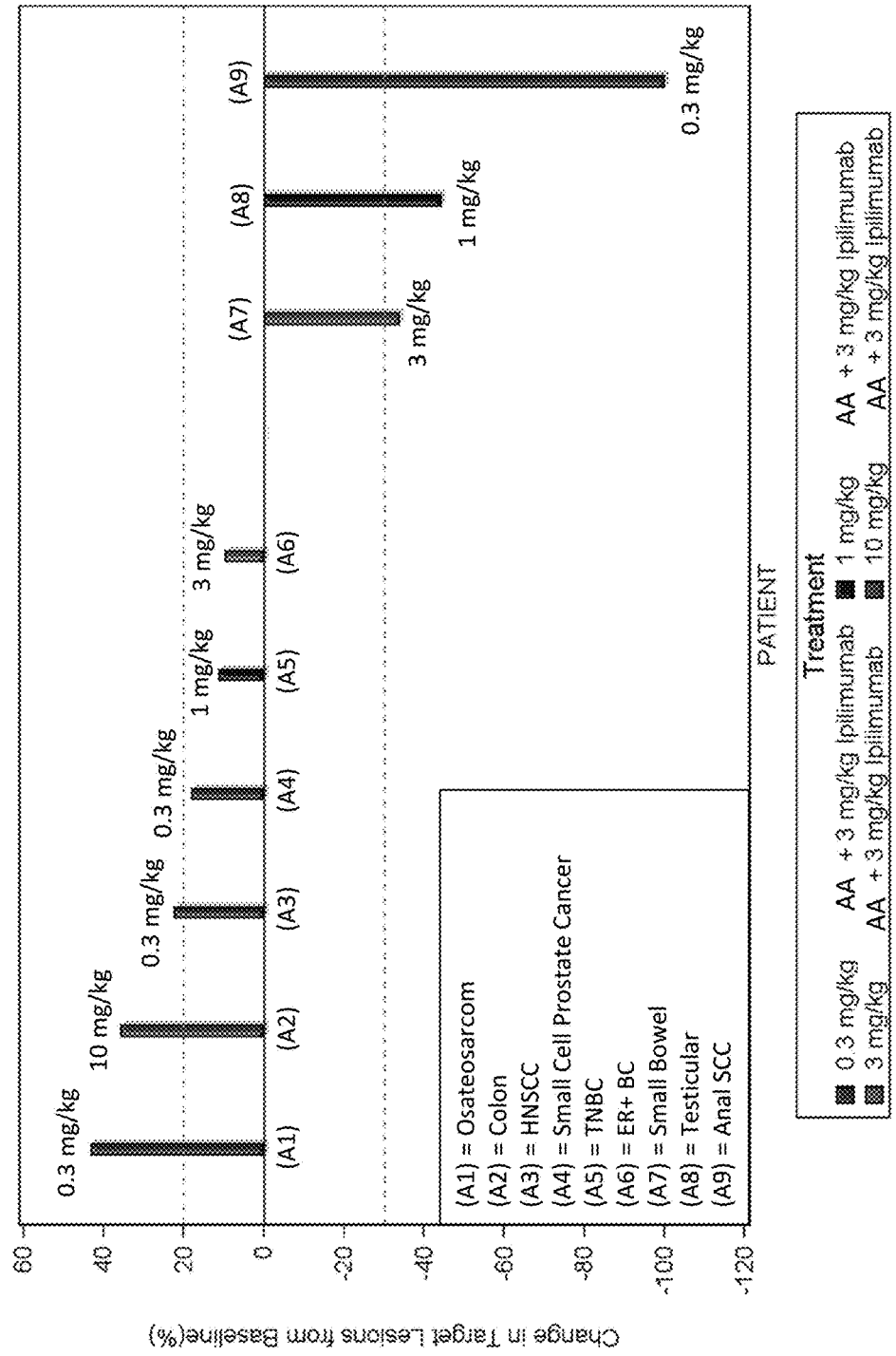
FIG. 10A depicts the best percentage change from baseline in target lesions after administration of the combination of PL07-2001-C5H9v2+ipilimumab.
Figure 10B:
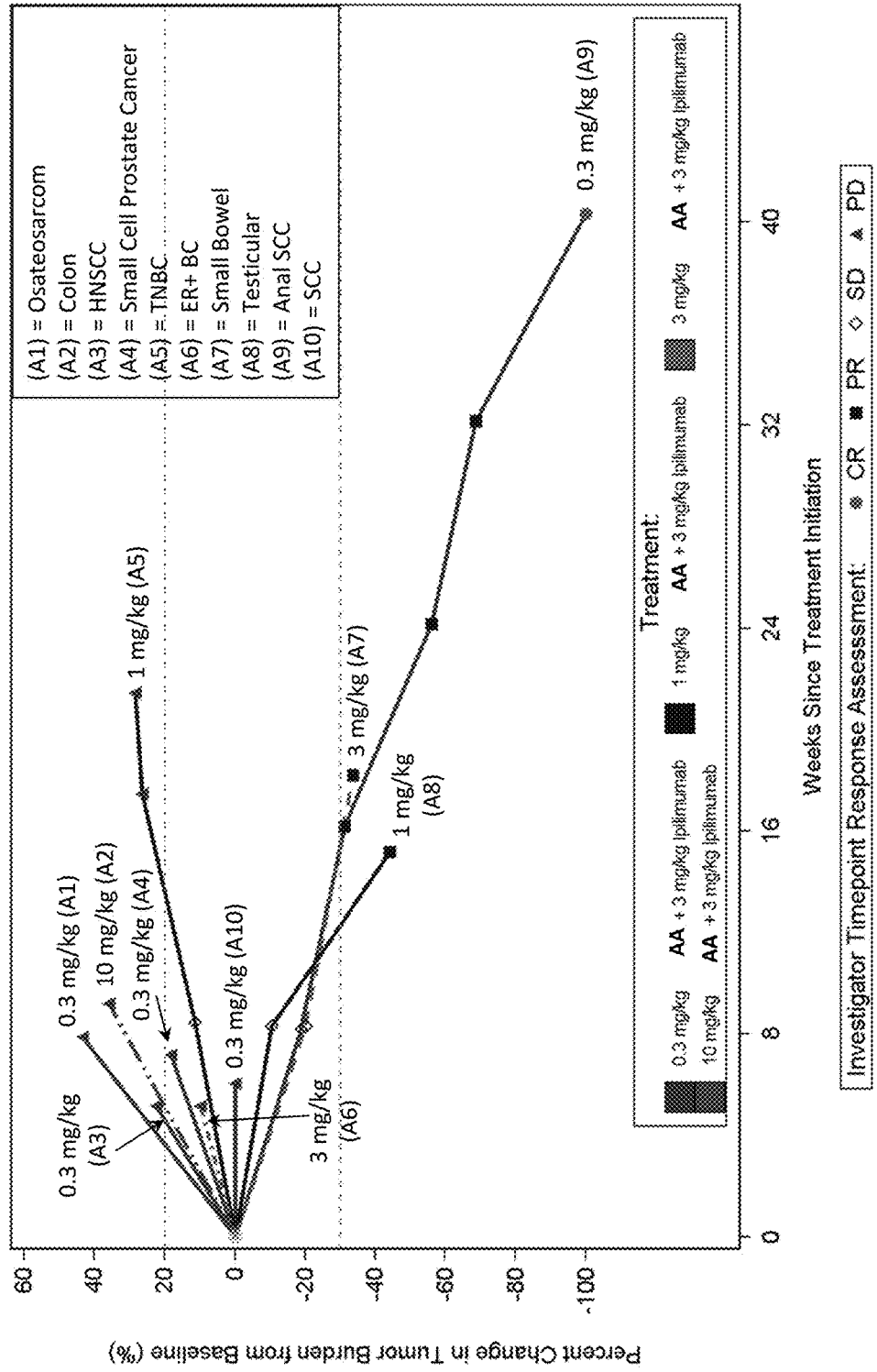
FIG. 10B is a spider plot depicting the change in target lesion (%) vs. time after administration of PL07-2001-C5H9v2. Abbreviations: CR, complete response; ER+BC, estrogen receptor-positive breast cancer; HNSCC, head and neck squamous cell carcinoma; PD, progressive disease; PR, partial response, RECIST, Response Evaluation Criteria in Solid Tumors; SCC, squamous cell carcinoma; SCLC, small cell lung cancer; SD, stable disease; TNBC, triple-negative breast cancer.

Among evaluable patients (n=12), best tumor response was:

(a) Complete response (n=1): anal cell Squamous cell carcinoma (0.3 mg/kg PL07-2001-05H9v2, 3 mg/kg ipilimumab); PD-L1 negative, MSS, low TMB, HPV-pos; and (b) Partial response (n=2): testicular cancer and unknown primary (likely small bowel). Target lesions decreased from baseline in 3 of 10 (30%) patients with measurable disease at baseline as shown in FIG. 10A. The percentage change in tumor burden over time is presented in FIG. 10B.

Sample Case Studies

Patient A has anal squamous cell carcinoma with intermediate tumor mutation burden (9 mutations/megabase), microsatellite-stable, HPV-positive, and PD-L1 status unknown. Patient was treated with PL07-2001-C5H9v2, 0.3 mg/kg+ipilimumab, 3 mg/kg and had unconfirmed complete response at follow-up staging.

Patient B has small bowel carcinoma and negative PD-L1 status. Patient was treated with PL07-2001-C5H9v2, 3 mg/kg+ ipilimumab, 3 mg/kg, and had an unconfirmed partial response at follow-up staging.

Conclusions

Early safety observations in this dose-escalation study of the combination of the anti-PD-L1 activatable antibody, PL07-2001-C5H9v2 and ipilimumab, 3 mg/kg, report a treatment-related AE rate trending below the level reported for other PD-1 pathway inhibitors in combination with ipilimumab. No new safety signals were observed with the combination of the anti-PD-L1 activatable antibody, PL07-2001-C5H9v2+ipilimumab, 3 mg/kg. Preliminary efficacy results show 1 complete response and 2 partial responses (3/12, 25%).

Example 2. Generation of Antibodies that Bind Activated and Intact Anti-PDL1 Activatable Antibodies The studies provided herein were designed to generate and evaluate antibodies that bind anti-PDL1 activatable antibodies of the disclosure.

The studies presented herein used the anti-PDL1 activatable antibody referred to herein as PL07-2001-C5H9v2, which comprises the heavy chain sequence of SEQ ID NO: 432 and the light chain sequence of SEQ ID NO: 428, as shown below.

PL07-2001-C5H9v2 Heavy Chain Amino Acid Sequence
(SEQ ID NO: 432)
EVQLLESGGGLVQPGGSLRLSCAASGFTFSSYAMSWVRQAPGKGLEWVSS

IWRNGIVTVYADSVKGRFTISRDNSKNTLYLQMNSLRAEDTAVYYCAKWS

AAFDYWGQGTLVTVSSASTKGPSVFPLAPCSRSTSESTAALGCLVKDYFP

EPVTVSWNSGALTSGVHTFPAVLQSSGLYSLSSVVTVPSSLGTKTYTCN

VDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLG

PL07-2001-C5H9v2 Light Chain Amino Acid Sequence
(SEQ ID NO: 428)
QGQSGSGIALCPSHFCQLPQTGGGSSGGSGGSGGISSGLLSGRSDNHGGS

DIQMTQSPSSLSASVGDRVTITCRASQSISSYLNWYQQKPGKAPKLLIYA

ASSLQSGVPSRFSGSGSGTDFTLTISSLQPEDFATYYCQQDNGYPSTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Mice were immunized by GenScript Biotech Corporation with peptide antigen CQQDNGYPSTFGGGT (SEQ ID NO: 1203), comprising the VL CDR3 of anti-PDL1 activatable antibody PL07-2001-C5H9v2, that was conjugated to the carrier protein Keyhole Limpet Hemocyanin (KLH) using the procedure shown below in Table 3. Six three-month old (3 Balb/c and 3 C56) mice were immunized according to the protocol listed below. At the time of each injection, the antigen aliquot was thawed and combined with Complete Freund's Adjuvant (CFA) for the first injection or with incomplete Freund's Adjuvant (IFA) for subsequent injections.

TABLE 10

Immunization Schedule

| Procedure | Schedule | Dosage and route |
|---|---|---|
| Pre-Immune Bleed | T = −4 days | |
| Primary immunization | T = 0 days | 50 μg/animal, s.c |
| Boost 1 | T = 14 days | 25 μg/animal, s.c |
| Test Bleed 1 | T = 21 days | |
| Boost 2 | T = 28 days | 25 μg/animal, s.c |
| Test Bleed 2 | T = 35 days | |
| Final Boost | T = 50 ± 7 days | 25 μg/animal, i.v. |
| Cell Fusion | 4 days after final boost | |

Serum titers against the free peptide as well as counter screen antigen (human IgG) were evaluated in test bleeds using a standard ELISA procedure. Leads were evaluated against full length activatable antibody in human plasma by Western blot. The results indicated that all mice had comparable titers against the respective immunogen. Antisera were tested against activatable antibody PL07-2001-C5H9v2 on the Wes™ system (ProteinSimple), and two mice were chosen for cell fusion.

Mouse monoclonal antibodies were generated as follows: Lymphocytes from the two mice were used for hybridoma fusion and plated on forty 96-well plates (400 million lymphocytes per mouse). The plates were kept in tissue culture incubators under standard conditions.

Example 3. Screening of Hybridoma Clones and Antibody Characterization

This Example describes the screening and characterization of hybridoma clones and resultant antibodies generated against anti-PDL1 activatable antibody PL07-2001-C5H9v2.

Figure 3A:
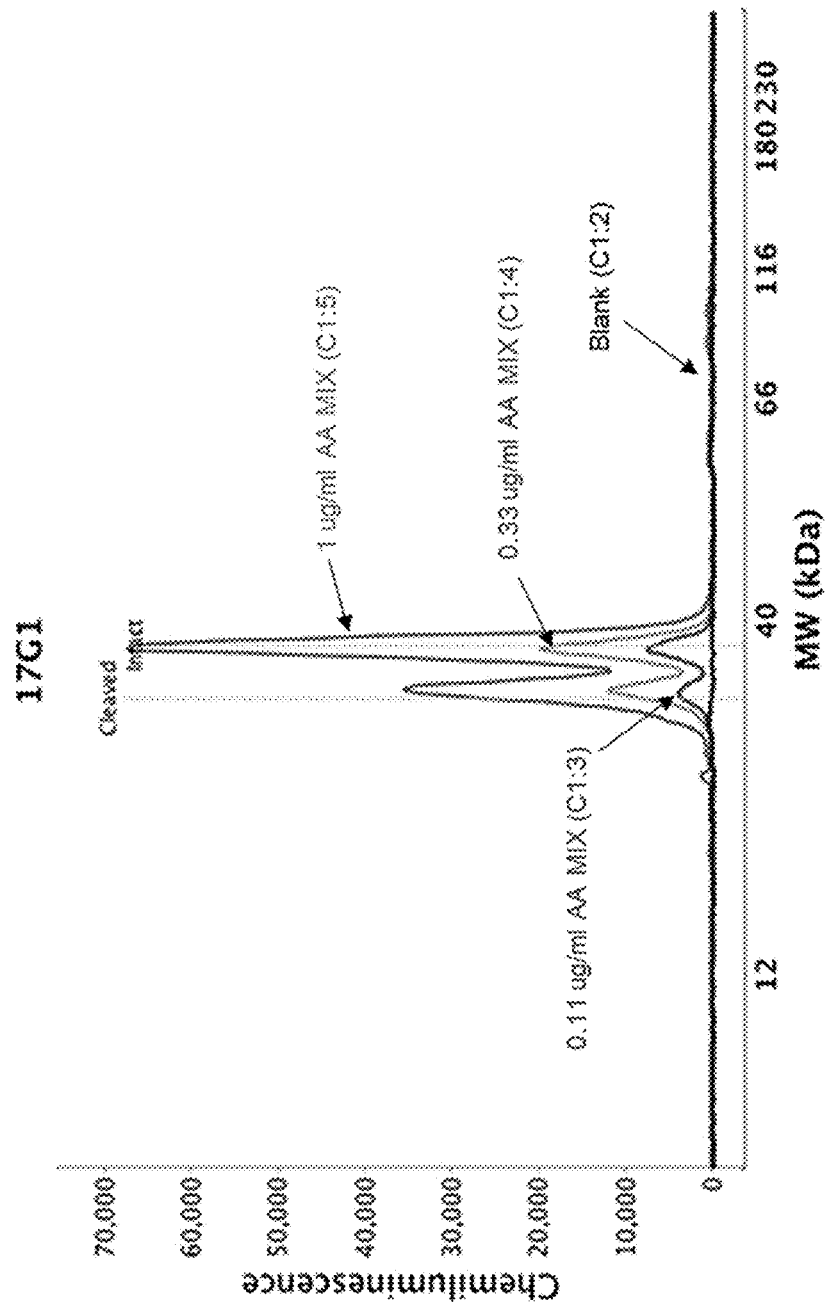
FIGS. 3A and 3B are a series of graphs depicting screening of PL07-2001-05H9v2 anti-idiotypic (anti-id) clones against 37% one-armed activated activatable antibody at 0.11, 0.33 and 1 ug/ml in human plasma at 1:100.
Figure 3B:
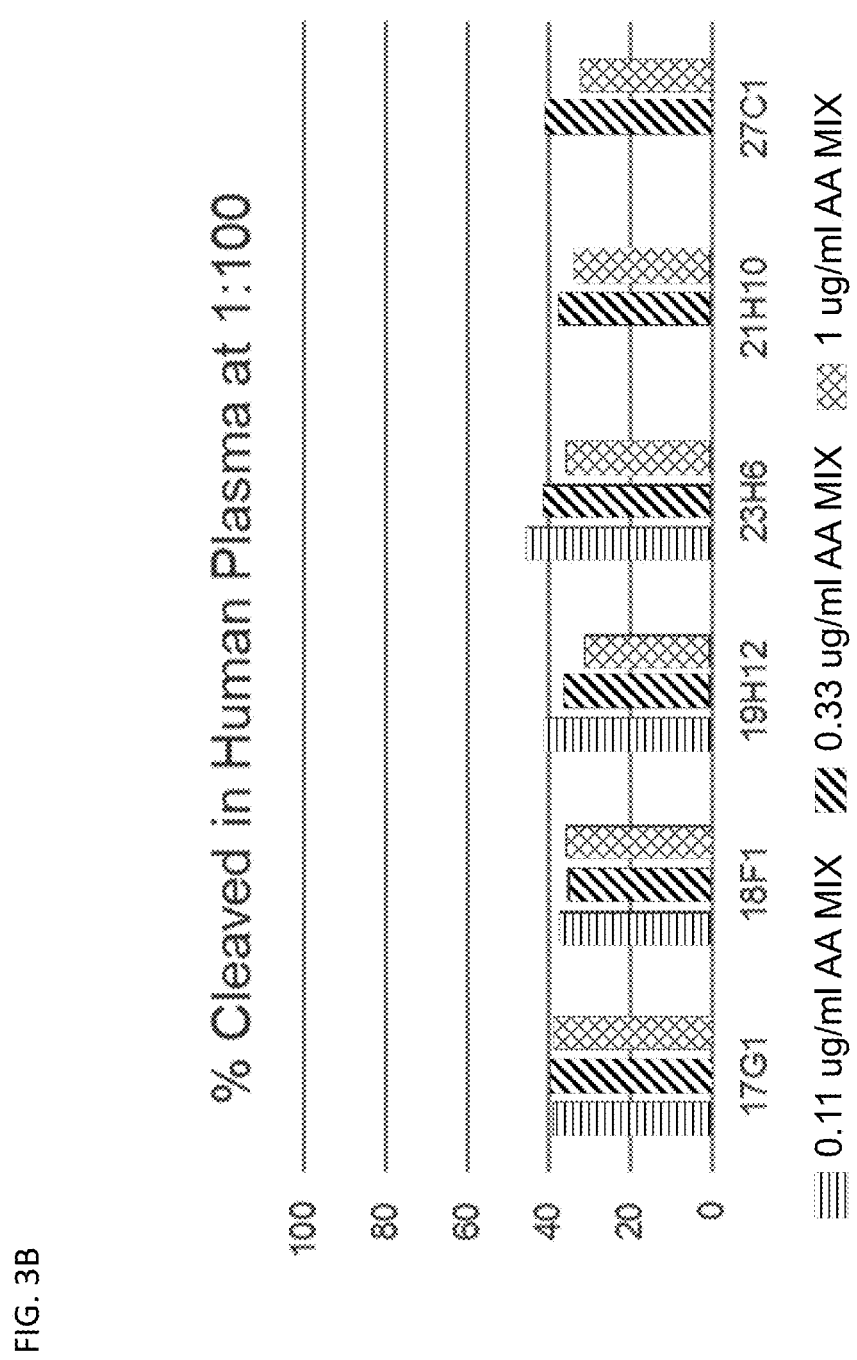

Hybridoma supernatant from parental clones were screened by GenScript against a short peptide containing the VL CDR3 of activatable antibody PL07-2001-C5H9v2 by indirect ELISA. Briefly, GenScript high binding plates were coated with peptide-BSA at 1 ug/mL concentration, 100 uL/well. Supernatant was used without dilution. Anti-serum at 1:1000 dilution was used as positive control. Peroxidase-AffiniPure Goat Anti-Mouse IgG, Fcγ Fragment Specific (minimum cross-reactive with human, bovine or horse serum albumin, also referred to as min X Hu, Bov, Hrs Sr Prot) was used as secondary. Twenty clones with positive signals were further screened against anti-PDL1 antibody C5H9v2, the parental antibody of activatable antibody PL07-2001-C5H9v2, and 5 ug/mL of human IgG. Anti-PDL1 antibody C5H9v2 was coated onto high binding plates at 1 ug/mL concentration, 100 uL/well. Human IgG was coated onto high-binding plates at 5 ug/mL concentration, 100 uL/well. Western blot analysis was also performed on these 20 clones using 200 ng of denatured and reduced anti-PDL1 antibody C5H9v2 as target. As a final screen, supernatants from the 20 clones were also assessed on the Wes system. Briefly, all 20 clones were tested against 1 ug/mL of one-arm activated activatable antibody PL07-2001-C5H9v2 in 0.1× sample buffer and 1 ug/mL of one-arm activated activatable antibody PL07-2001-C5H9v2 in 1:100 human plasma. The top 6 clones as assessed by intensity and specificity of binding to activatable antibody PL07-2001-05H9v2, referred to as 17G1, 18F1, 19H12, and 23H6, 21H10 and 27C1, were further screened against one-arm activated activatable antibody PL07-2001-C5H9v2 at 0.11 and 0.33 ug/mL concentrations in 1:100 human plasma. Results are shown in FIG. 3A and FIG. 3B, which shows screening of activatable antibody PL07-2001-C5H9v2 anti-idiotypic (anti-id) clones against 37% one-arm activated activatable antibody PL07-2001-C5H9v2 at 0.11, 0.33 and 1 ug/ml in human plasma at 1:100. FIG. 3A is an electropherogram showing 17G1 detection of decreasing concentrations of one-arm activated activatable antibody PL07-2001-05H9v2 (1, 0.33, and 0.11 ug/ml). FIG. 3B portrays the relative activation percent for the top 6 clones of one-arm activated activatable antibody PL07-2001-C5H9v2. The relative activation rate is preserved at different concentrations. Clones 21H10 and 27C1 have lower affinity resulting in no data for the 0.11 ug/ml concentration.

Example 4. Binding Specificity of Antibodies that Bind Anti-PDL1 Activatable Antibody This Example describes the ability of antibodies of the disclosure to bind anti-PDL1 activatable antibody PL07-2001-C5H9v2.

Figure 4A:
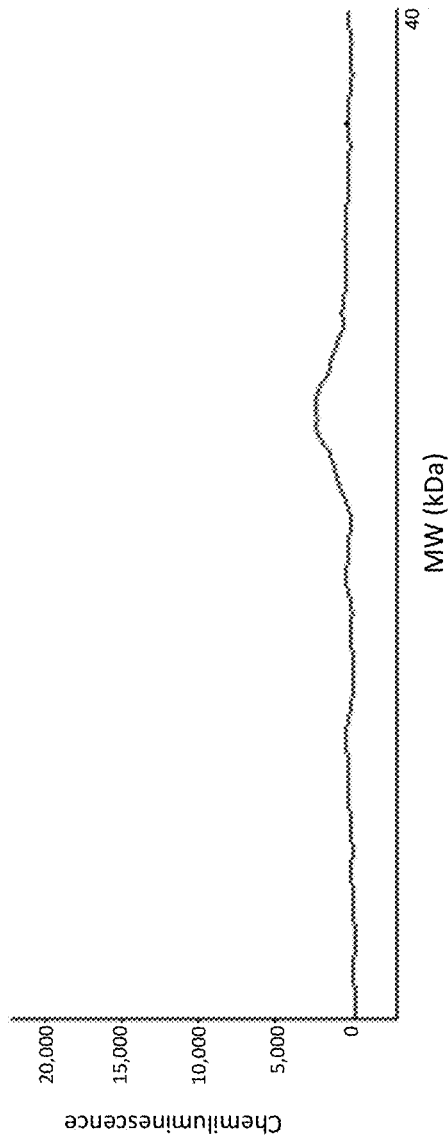
FIGS. 4A, 4B, 4C, and 4D are a series of graphs depicting that the antibody referred to herein as 17G1 has high specificity to the activatable antibody (AA) PL07-2001-05H9v2. 17G1 was assessed on the Wes for specificity by spiking 160 ng/ml of one arm activated PL07-2001-C5H9v2 (activated AA) into either human plasma (FIG. 4C) or lung tumor lysates (FIG. 4D).
Figure 4B:
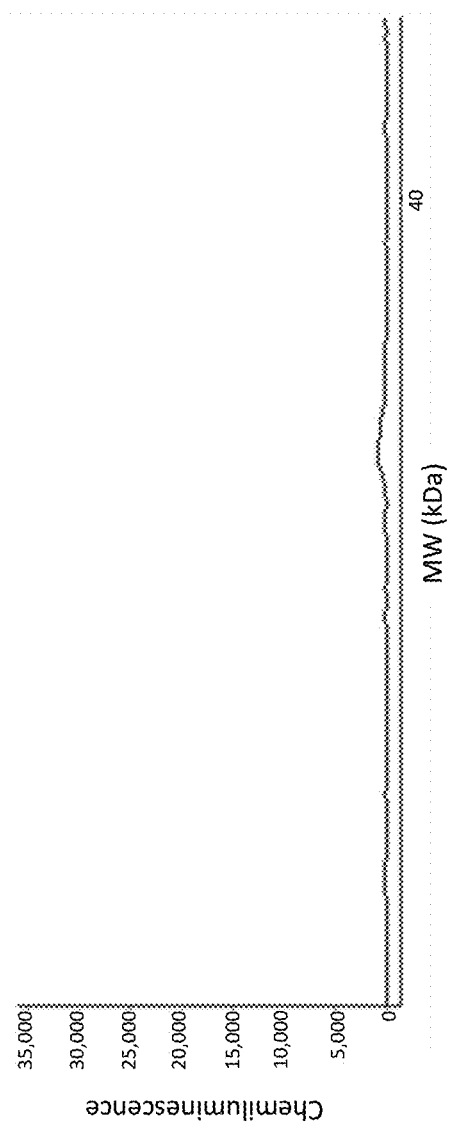
Figure 4C:
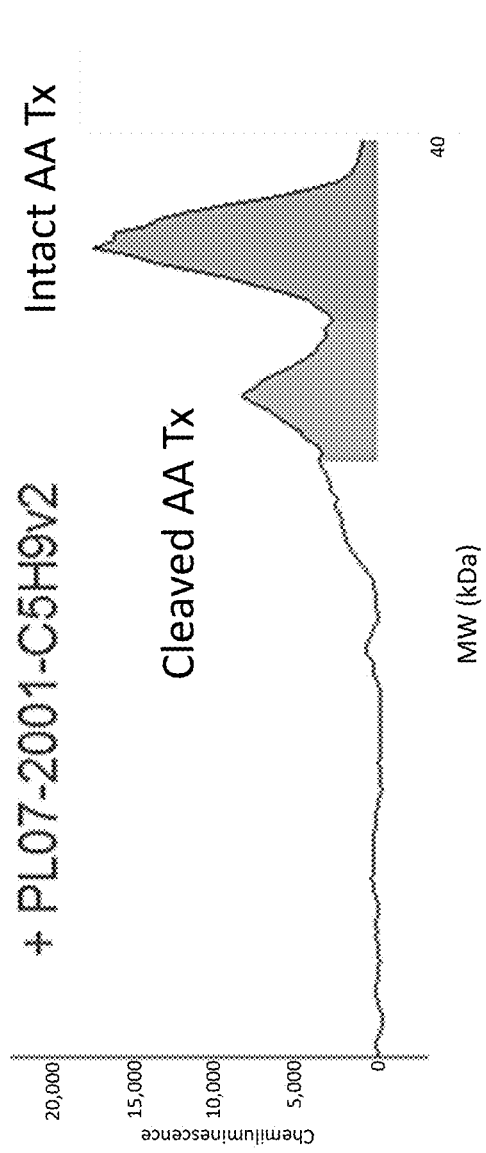
Figure 4D:
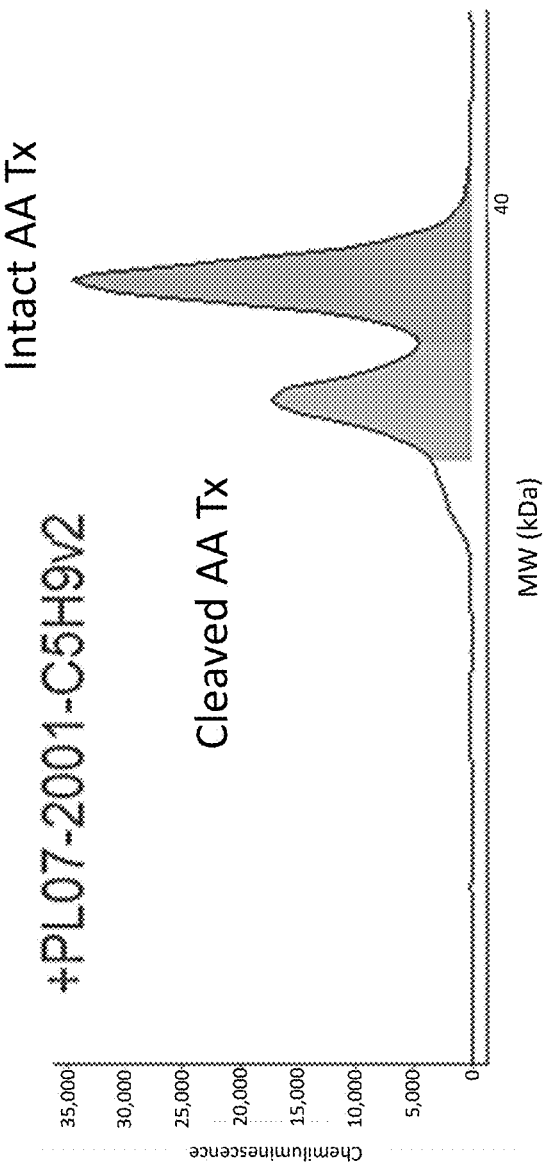

To test for specificity of antibody 17G1 binding to anti-PDL1 activatable antibody PL07-2001-C5H9v2, 160 ng/mL of one-arm activated anti-PDL1 activatable antibody PL07-2001-C5H9v2 were spiked into either human plasma (1 to 100 dilution in PBS) or lung tumor lysate. Briefly, tumor homogenates were prepared in Thermo Scientific Pierce™ IP Lysis Buffer (Catalog #87788) with added Thermo Scientific Halt™ Protease Inhibitor Single Use Cocktail Kit (Catalog #78430) using Barocycler (Pressure Biosciences). Antibody 17G1 was also tested against the same plasma and tumor that were not spiked with one-arm activated anti-PDL1 activatable antibody PL07-2001-C5H9v2. The test samples were then analyzed by the Wes capillary electrophoresis immunoassay-based method, wherein separation was effected by SDS-based electrophoresis (Protein Simple), also referred to as the Wes system. FIGS. 4A-4D demonstrate high binding specificity of antibody 17G1 to anti-PDL1 activatable antibody PL07-2001-C5H9v2 spiked into human plasma (FIG. 4C) and lung tumor lysate samples (FIG. 4D). FIGS. 4A and 4B demonstrate background binding of antibody 17G1 in human plasma and lung tumor lysate samples, respectively, in the absence of anti-PDL1 activatable antibody PL07-2001-C5H9v2.

Example 5. Quantification of Activated and Intact Anti-PDL1 Activatable Antibodies in Biological Samples This Example describes the ability of antibody 17G1 to detect activated and intact anti-PDL1 activatable antibody PL07-2001-C5H9v2 in plasma and xenograft tumor samples of mice administered anti-PDL1 activatable antibody PL07-2001-C5H9v2.

Anti-PDL1 activatable antibody PL07-2001-C5H9v2 is designed to be cleaved (i.e., activated) by a number of serine proteases and matrix metalloproteinases (MMPs) which are generally associated with human tumors (LeBeau et al, Imaging a functional tumorigenic biomarker in the transformed epithelium. Proc Natl Acad Sci 2013; 110: 93-98; Overall & Kleifeld, 2006, Validating Matrix Metalloproteinases as Drug Targets and Anti-Targets for Cancer Therapy. Nature Review Cancer, 6, 227-239), and which have low activity in blood or in normal tissues. To evaluate and measure activatable antibody activation in tumor and plasma samples, samples were analyzed by the Wes system that enables detection of intact and activated anti-PDL1 activatable antibody PL07-2001-C5H9v2 as described herein. Using this system, it was shown that the activatable antibodies remain mostly intact (i.e., inactivated) in circulation, but are activated in mouse xenograft tumors.

In general, the following protocol was used: a mouse xenograft tumor model was developed by SC implantation of $3\times10^6$ MDA-MB-231-luc2-4D3LN cells in 30 uL serum-free medium containing matrigel (1:1) to 7-8 weeks old female nude mice. Body weights and tumor measurements were measured and recorded twice weekly for the duration of the study. After tumors achieved volume of 200-500 mm$^3$, mice were randomized into 3 groups of equivalent average tumor volume and dosed with anti-PDL1 activatable antibody PL07-2001-05H9v2. Four days after treatment, tumor and plasma (heparin) were collected and stored at −80° C. prior to analysis. Tumor homogenates (i.e., lysates) were prepared in Thermo Scientific Pierce™ IP Lysis Buffer (Catalog #87788) with added Thermo Scientific Halt' Protease Inhibitor Single Use Cocktail Kit (Catalog #78430) using Barocycler (Pressure Biosciences). Approximately 0.8 mg/mL of protein lysate in IP lysis buffer with HALT™ protease inhibitor/EDTA and plasma samples diluted 1 in 100 in PBS were analyzed by the Wes system as described herein.

Samples were analyzed using a protocol similar to that described by ProteinSimple in the Simple Western Size Assay Development Guide (http://www.proteinsimple.com/documents/042-889_Rev1_Size_Assay_Development_Guide.pdf), as long as that method enables separation of intact and activated species. In some embodiments, varying any one more of the following using the methods can be used to facilitate separate of intact and activated species: varying, e.g., increasing or decreasing, stacking time, varying, e.g., increasing or decreasing, sample time, and/or varying, e.g., increasing or decreasing, separation time.

In general, one part (e.g., 1 µL) 5× Fluorescent Master Mix (ProteinSimple) was combined with 4 parts (e.g., 4 µL) lysate to be tested in a microcentrifuge tube. A 1 ng to 5 ug range of anti-PDL1 activatable antibody PL07-2001-C5H9v2 was used for antibody screening and characterization. For biological samples comprising tumor tissue, 0.8 mg/mL of protein lysate in IP lysis buffer with HALT protease inhibitor/EDTA was used. Plasma samples were diluted 1 in 100 in PBS. Primary antibodies were used at a concentration of 1.7 ng/mL (diluted in Antibody diluent 2 (ProteinSimple Cat #042-203). Mouse secondary antibody (ProteinSimple) was used neat. Plates with samples prepared according to the Simple Western Size Assay Development Guide were centrifuged for 5 minutes at 2500 rpm (~1000× g) at room temperature before analyzing on the Wes system (ProteinSimple).

Figure 5A:
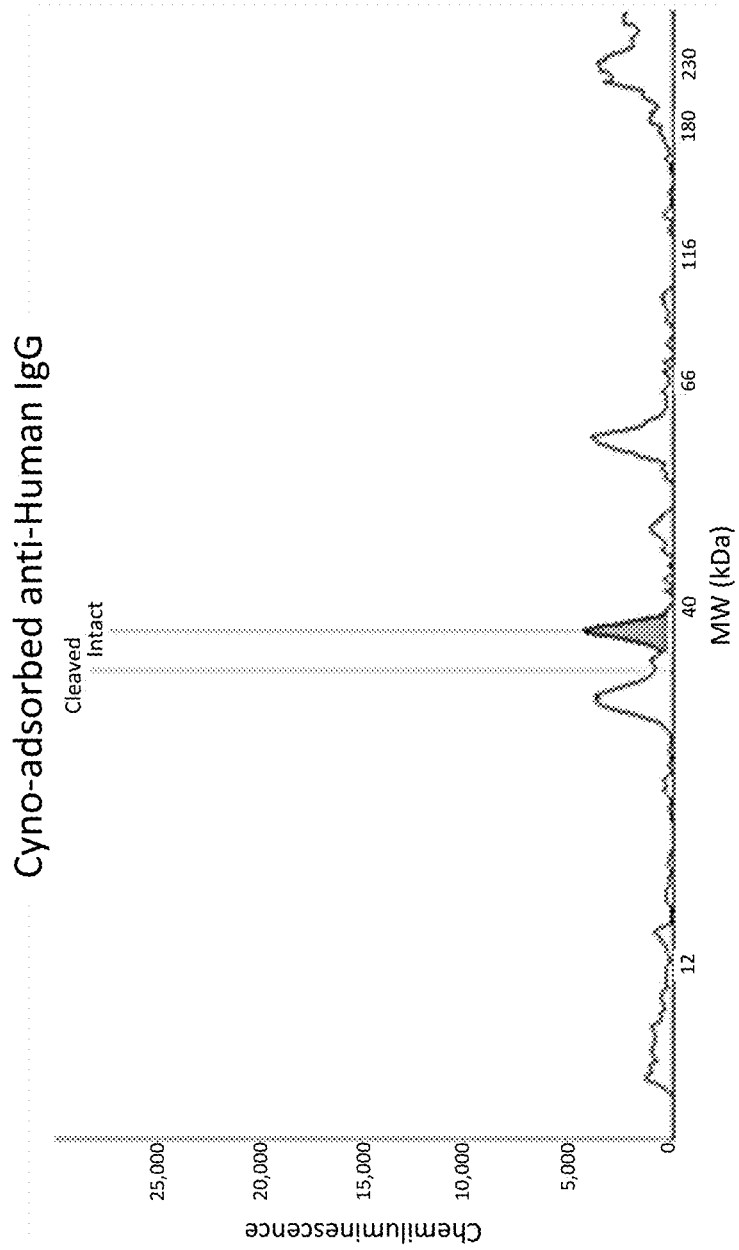
FIGS. 5A and 5B are a series of graphs depicting specific detection of activatable antibody (AA) therapeutics by selective anti-idiotypic antibodies.
Figure 5B:
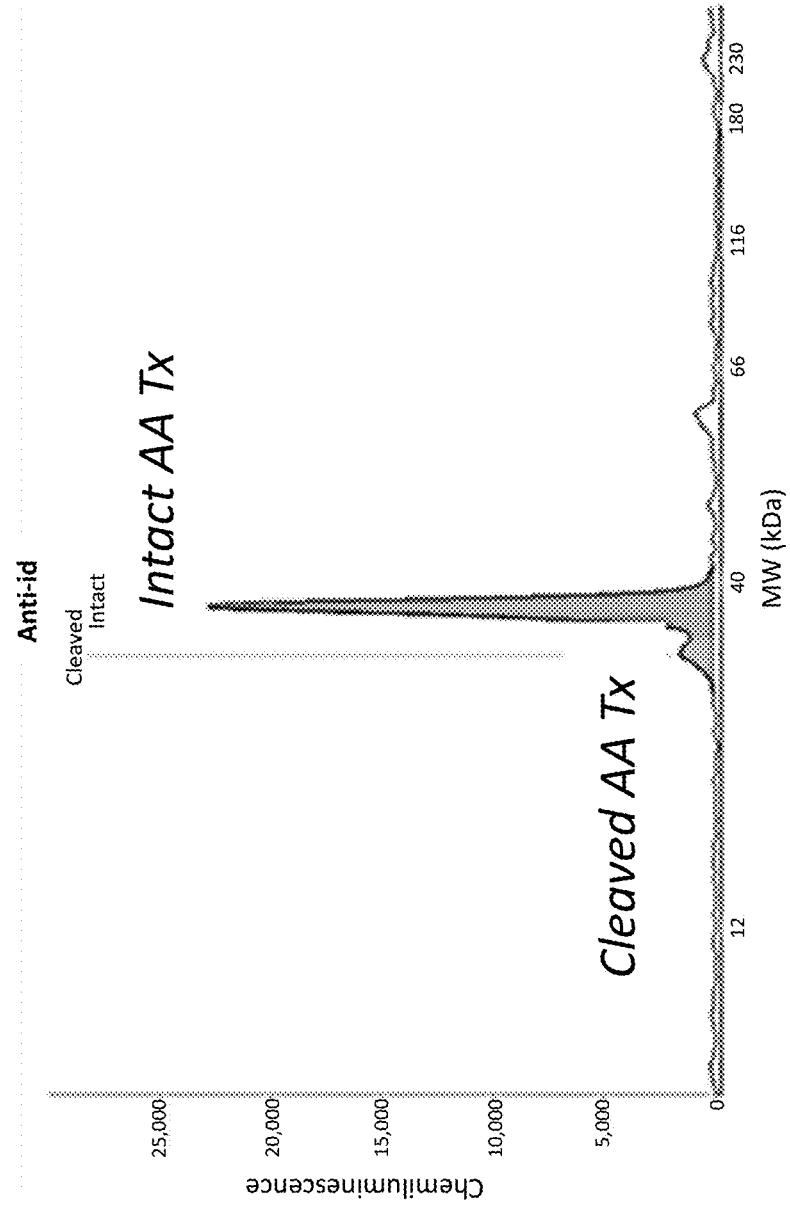

FIGS. 5A and 5B compare specific detection of intact and activated anti-PDL1 activatable antibody PL07-2001-C5H9v2 by anti-idiotypic antibody 17G1 of the disclosure and commercial anti-human IgG A110UK (cynomolgus monkey adsorbed goat anti-human IgG) from American Qualex. Antibody 17G1 of the disclosure was able to detect anti-PDL1 activatable antibody PL07-2001-C5H9v2 in plasma of mice treated with only 0.1 mg/kg of anti-PDL1 activatable antibody PL07-2001-C5H9v2 (FIG. 5B) as compared to the commercial human IgG antibody only being able to minimally detect anti-PDL1 activatable antibody PL07-2001-C5H9v2 in plasma of mice treated with 10 mg/kg anti-PDL1 activatable antibody PL07-2001-C5H9v2 (FIG. 5A).

FIGS. 6A and 6B show preferential activation of anti-PDL1 activatable antibody PL07-2001-C5H9v2 in tumor versus plasma samples. In this study, MDA-MD-231 xenograft mice were treated with 1 mg/kg of anti-PDL1 activatable antibody PL07-2001-05H9v2. Tumor and plasma samples were collected on day 4 (96 hours). Tumor homogenate and plasma samples were analyzed in the Wes system using the 17G1 antibody for detection. Plasma samples exhibited intact anti-PDL1 activatable antibody PL07-2001-C5H9v2 (FIG. 6B) whereas the tumor microenvironment activated at least a portion of the anti-PDL1 activatable antibody PL07-2001-C5H9v2 (FIG. 6A).

Example 6. Quantification of Activated and Intact Anti-PDL1 Activatable Antibodies in Biological Samples This Example demonstrates that the Wes system can be applied to different xenograft tumor types and different dosing concentrations.

Figure 7A:
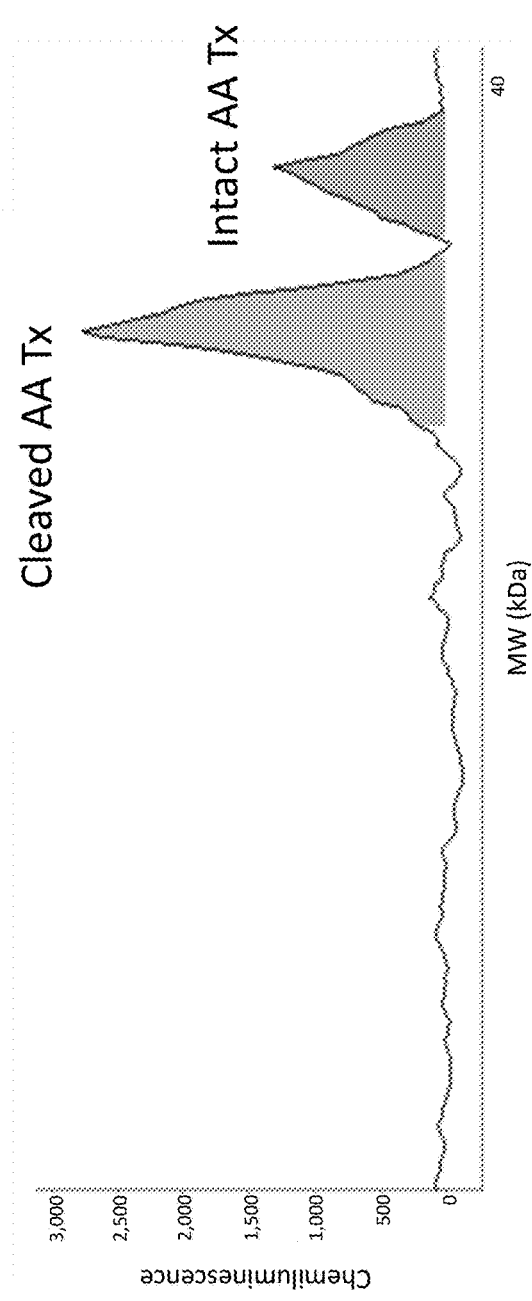
FIGS. 7A and 7B are a series of graphs depicting preferential activation of activatable antibody therapeutics in tumor versus plasma detected in another xenograft tumor model. SAS xenograft mice were treated with 0.1 mg/kg of the anti-PDL1 activatable antibody referred to herein as PL07-2001-C5H9v2.
Figure 7B:
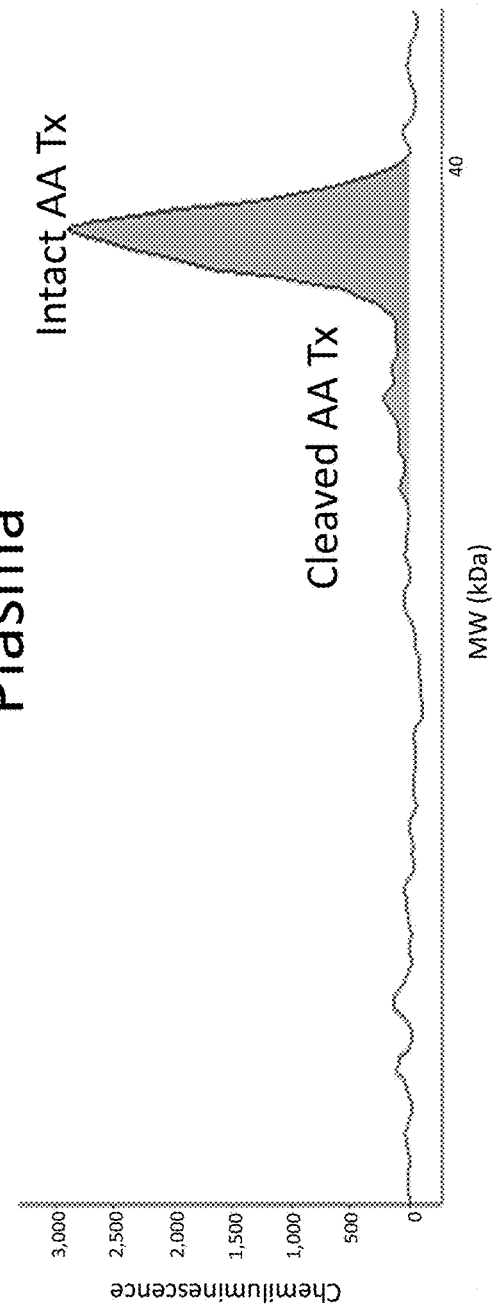

Briefly, a mouse xenograft tumor model was developed by SC implantation of $5\times10^6$ SAS cells in 100 uL serum-free medium to 7-8 week old female nude mice. Body weights and tumor measurements were measured and recorded twice weekly for the duration of the study. After tumors achieved volume of 450-550 mm³, mice were randomized into 3 groups of equivalent average tumor volume and dosed with 0.1 mg/kg of anti-PDL1 activatable antibody PL07-2001-C5H9v2. Four days after treatment, tumor and plasma (heparin) samples were collected and stored at −80° C. prior to analysis. Tumor homogenates (i.e., lysates) were prepared in Thermo Scientific Pierce™ IP Lysis Buffer (Catalog #87788) with added Thermo Scientific Halt™ Protease Inhibitor Single Use Cocktail Kit (Catalog #78430) using Barocycler (Pressure Biosciences). Approximately 0.8 mg/mL of protein lysate in IP lysis buffer with HALT protease inhibitor/EDTA and plasma samples diluted 1 in 250 in PBS were analyzed by the Wes system using the 17G1 antibody for detection. FIGS. 7A and 7B indicate the preferential activation of activatable antibody therapeutics in tumor versus plasma samples.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed:

1. A method of treating, alleviating a symptom of, or delaying the progression of a cancer in a subject, comprising administering intravenously an activatable anti-PDL1 antibody to the subject, wherein the subject is a human and wherein the activatable anti-PDL1 antibody comprises:

a. an antibody (AB) that specifically binds to human PDL1, wherein the AB comprises:

i. a heavy chain variable region comprising a complementarity determining region 1 (CDRH1) comprising the amino acid sequence of SEQ ID NO:212, a complementarity determining region 2 (CDRH2) comprising the amino acid sequence of SEQ ID NO:246, and a complementarity determining region 3 (CDRH3) comprising the amino acid sequence or SEQ ID NO:235; and ii. a light chain variable region comprising a light chain complementarity determining region 1 (CDRL1) comprising the amino acid sequence of SEQ ID NO:209, a light chain complementarity determining region 2, (CDRL2) comprising the amino acid sequence of SEQ ID NO:215, a light chain complementarity determining region 3 (CDRL3) comprising the amino acid sequence of SEQ ID NO:228;
b. a cleavable moiety (CM) linked to the AB, wherein the CM is a polypeptide that functions as a substrate for a protease, wherein the CM comprises the amino acid sequence of SEQ ID NO: 377; and
c. a masking moiety (MM) linked to the AB, wherein the MM comprises the amino acid sequence of SEQ ID NO: 63;
wherein the activatable anti-PDL1 antibody is administered at a dose selected from the group consisting of 6 mg/kg, 15 mg/kg, and 30 mg/kg.

2. A method of treating, alleviating a symptom of, or delaying the progression of a cancer in a subject, comprising administering intravenously an activatable anti-PDL1 antibody to the subject, wherein the subject is a human and wherein the activatable anti-PDL1 antibody comprises:
a. an antibody (AB) that specifically binds to human PDL1, wherein the AB comprises:
i. a heavy chain variable region comprising a complementarity determining region 1 (CDRH1) comprising the amino acid sequence of SEQ ID NO:212, a complementarity determining region 2 (CDRH2) comprising the amino acid sequence of SEQ ID NO:246, and a complementarity determining region 3 (CDRH3) comprising the amino acid sequence or SEQ ID NO:235; and
ii. a light chain variable region comprising a light chain complementarity determining region 1 (CDRL1) comprising the amino acid sequence of SEQ ID NO:209, a light chain complementarity determining region 2, (CDRL2) comprising the amino acid sequence of SEQ ID NO:215, a light chain complementarity determining region 3 (CDRL3) comprising the amino acid sequence of SEQ ID NO:228;
b. a cleavable moiety (CM) linked to the AB, wherein the CM is a polypeptide that functions as a substrate for a protease, wherein the CM comprises the amino acid sequence of SEQ ID NO: 377; and
c. a masking moiety (MM) linked to the AB, wherein the MM comprises the amino acid sequence of SEQ ID NO: 63;
wherein the activatable anti-PDL1 antibody is administered at a fixed dose selected from the group consisting of 800 mg, 1200 mg, and 2400 mg.

3. The method of claim 2, wherein the MM inhibits the binding of the AB to human PDL1 when the activatable anti-PDL1 antibody is in an uncleaved state.

4. The method of claim 2, wherein the AB comprises a heavy chain variable region (VH) comprising the amino acid sequence of SEQ ID NO: 46 and a light chain variable (VL) comprising the amino acid sequence of SEQ ID NO: 58 or SEQ ID NO: 137.

5. The method of claim 2, wherein the activatable anti-PDL1 antibody comprises a light chain comprising the amino acid sequence of SEQ ID NO: 1008 and a heavy chain comprising the amino acid sequence of SEQ ID NO: 432.

6. The method of claim 2, wherein the activatable anti-PDL1 antibody comprises a light chain comprising the amino acid sequence of SEQ ID NO: 428 and a heavy chain comprising the amino acid sequence of SEQ ID NO: 432.

7. The method of claim 1, wherein the dose is 6 mg/kg.
8. The method of claim 1, wherein the dose is 15 mg/kg.
9. The method of claim 1, wherein the dose is 30 mg/kg.
10. The method of claim 2, wherein the fixed dose is 800 mg.
11. The method of claim 2, wherein the fixed dose is 1200 mg.
12. The method of claim 2, wherein the fixed dose is 2400 mg.
13. The method of claim 2, wherein the activatable anti-PDL1 antibody is administered on a schedule of one dose every 7-30 days.
14. The method claim 13, wherein the activatable anti-PDL1 antibody is administered on a schedule of one dose every 14 days.
15. The method claim 13, wherein the activatable anti-PDL1 antibody is administered on a schedule of one dose every 21 days.
16. The method of claim 2, wherein the activatable anti-PDL1 antibody is administrated as a monotherapy.
17. The method of claim 2, wherein the activatable anti-PDL1 antibody is administrated as a component of a combination therapy.
18. The method claim 17, wherein the combination therapy comprises administering a dose of an anti-CTLA-4 antibody or a B-RAF inhibitor.
19. The method of claim 18 wherein the anti-CTLA-4 antibody is ipilimumab.
20. The method of claim 18, wherein the combination therapy comprises administering the dose of the anti-CTLA-4 antibody wherein the anti-CTLA-4 antibody is administered intravenously.
21. The method of claim 18, wherein the anti-CTLA-4 antibody is administered at a dose of 3 mg/kg, 6 mg/kg, or 10 mg/kg.
22. The method of claim 18, wherein the anti-CTLA-4 antibody is administered at a fixed dose of 240 mg, 480 mg or 800 mg.
23. The method of claim 18, wherein the B-RAF inhibitor is vemurafenib.
24. The method of 23 wherein the B-RAF inhibitor is administered orally.
25. The method of claim 18, wherein the B-RAF inhibitor is administered at a dose of 960 mg.
26. The method of claim 18, wherein the B-RAF inhibitor is administered at a dose of 875 mg.
27. The method of claim 18, wherein the administering step comprises administering the activatable anti-PDL1 antibody and the B-RAF inhibitor over a same period of time.
28. The method of claim 18, wherein a dose of the B-RAF inhibitor is administered twice daily.
29. The method of claim 18, wherein at least 4 doses each of the activatable anti-PDL1 antibody and the B-RAF inhibitor are administered.
30. The method of claim 18, wherein the administering step comprises administering multiple doses of the activatable anti-PDL1 antibody and the anti-CTLA-4 antibody over a first period of time, followed by administration of multiple doses of the activatable anti-PDL1 antibody as a monotherapy over a second period of time.
31. The method claim 18, wherein a dose of the activatable anti-PDL1 antibody and a dose of the anti-CTLA-4 antibody are administered concomitantly as a combination therapy every 21 days for 4 doses, followed by administration of a dose of the activatable anti-PDL1 antibody as a monotherapy every 14 days.
32. The method of claim 18, wherein the administering step comprises administering multiple doses of the activatable anti-PDL1 antibody as a monotherapy over a first period of time, followed by concomitant administration of multiple doses of the activatable anti-PDL1 antibody and the anti-CTLA-4 antibody as a combination therapy over a second period of time.

33. The method of claim 18, wherein the administering step comprises (i) administering multiple doses of the activatable anti-PDL1 antibody as a monotherapy over a first period of time, (ii) subsequently administering multiple doses of the activatable anti-PDL1 antibody and the anti-CTLA-4 antibody as a combination therapy over a second period of time, and (iii) subsequently administering multiple doses of the activatable anti-PDL1 antibody as a monotherapy over a third period of time.

34. The method of claim 18, wherein the activatable anti-PDL1 antibody is administered as a monotherapy every 14 days for 4 doses, followed by administration of the activatable anti-PDL1 antibody and the anti-CTLA-4 antibody as a combination therapy every 21 days, for 4 doses, followed by administration of the activatable anti-PDL1 antibody as a monotherapy every 14 days.

35. The method of claim 2, wherein the subject exhibits one or more of the following characteristics:

a. PD-1/PDL1 inhibitor-naïve,
b. CTLA-4 inhibitor-naïve,
c. BRAF$^{V600E}$ mutation positive,
d. BRAF inhibitor-naïve,
e. PDL1 positive,
f. PDL1 unknown, and
g. been previously treated with a PD1/PDL1 inhibitor.

36. The method of claim 2, wherein the subject has no further standard of care available.

37. The method of claim 2, wherein a PD1/PDL1 inhibitor therapy is not approved for the subject's cancer.

38. The method of claim 2, wherein the subject has been previously treated with a PD-1/PDL1 inhibitor, wherein treatment with the PD-1/PDL1 inhibitor was discontinued for reasons other than toxicity, and wherein the subject is CTLA-4 inhibitor-naïve.

39. The method of claim 2, wherein the subject is immunotherapy naïve.

* * * * *